United States Patent
Kim et al.

(10) Patent No.: US 9,673,400 B2
(45) Date of Patent: Jun. 6, 2017

(54) AMINE-BASED COMPOUND AND ORGANIC LIGHT-EMITTING DIODE INCLUDING THE SAME

(71) Applicants: SAMSUNG DISPLAY CO., LTD., Yongin, Gyeonggi-Do (KR); SNU R&DB Foundation, Seoul (KR)

(72) Inventors: Mi-Kyung Kim, Yongin (KR); Chang-Woong Chu, Yongin (KR); Sam-Il Kho, Yongin (KR); Dong-Hyun Kim, Yongin (KR); Kwan-Hee Lee, Yongin (KR); Jong-In Hong, Seoul (KR); Seong-Jin Jeong, Seoul (KR)

(73) Assignees: Samsung Display Co., Ltd., Yongin-si (KR); SNU R&DB Foundation, Seoul (KR)

( * ) Notice: Subject to any disclaimer, the term of this patent is extended or adjusted under 35 U.S.C. 154(b) by 528 days.

(21) Appl. No.: 14/308,664

(22) Filed: Jun. 18, 2014

(65) Prior Publication Data

US 2014/0374717 A1 Dec. 25, 2014

(30) Foreign Application Priority Data

Jun. 19, 2013 (KR) .................. 10-2013-0070487

(51) Int. Cl.
 *H01L 51/00* (2006.01)
 *H01L 51/50* (2006.01)
 (Continued)

(52) U.S. Cl.
 CPC ........ *H01L 51/0055* (2013.01); *C07C 211/54* (2013.01); *C07C 211/61* (2013.01);
 (Continued)

(58) Field of Classification Search
 CPC . C07C 2103/52; C07C 211/54; C07C 211/61; C07C 255/58; C07F 7/0818;
 (Continued)

(56) References Cited

U.S. PATENT DOCUMENTS

2004/0076853 A1* 4/2004 Jarikov ................. C09K 11/06
 428/690
2016/0211454 A1* 7/2016 Kim .................... H01L 51/0054

FOREIGN PATENT DOCUMENTS

JP 2009-215333 A 9/2009
KR 10-2010-0112903 A 10/2010
 (Continued)

*Primary Examiner* — Dawn Garrett
(74) *Attorney, Agent, or Firm* — Lewis Roca Rothgerber Christie LLP

(57) ABSTRACT

An amine-based compound is represented by Formula 1:

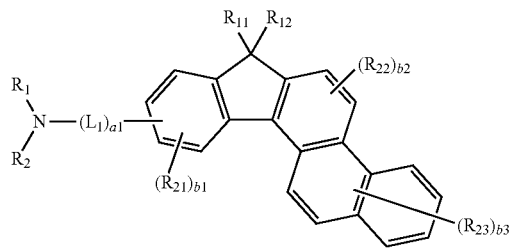

An organic light-emitting diode includes a first electrode, a second electrode, and an organic layer between the first electrode and the second electrode. The organic layer includes an emission layer and the amine-based compound represented by Formula 1. The OLED including the amine-
(Continued)

based compound represented by Formula 1 has good color purity, low driving voltage, high efficiency, high brightness, and/or a long lifetime.

20 Claims, 2 Drawing Sheets

(51) Int. Cl.
    *C07C 255/58*     (2006.01)
    *C07C 211/54*     (2006.01)
    *C07C 211/61*     (2006.01)
    *C07F 7/08*     (2006.01)
    *C09K 11/06*     (2006.01)

(52) U.S. Cl.
    CPC .......... *C07C 255/58* (2013.01); *C07F 7/0818* (2013.01); *C09K 11/06* (2013.01); *H01L 51/006* (2013.01); *C07C 2103/52* (2013.01); *C09K 2211/1011* (2013.01); *C09K 2211/1014* (2013.01); *H01L 51/002* (2013.01); *H01L 51/0058* (2013.01); *H01L 51/0061* (2013.01); *H01L 51/0072* (2013.01); *H01L 51/0077* (2013.01); *H01L 51/5012* (2013.01); *H01L 51/5052* (2013.01); *H01L 2251/308* (2013.01)

(58) Field of Classification Search
    CPC ............ C09K 11/06; C09K 2211/1011; C09K 2211/1014; H01L 2251/308; H01L 51/002; H01L 51/0055; H01L 51/0058; H01L 51/006; H01L 51/0061; H01L 51/0072; H01L 51/0077; H01L 51/501
    See application file for complete search history.

(56) References Cited

FOREIGN PATENT DOCUMENTS

| KR | 10-2012-0052499 A | 5/2012 |
|---|---|---|
| KR | 10-2012-0083203 A | 7/2012 |

* cited by examiner

AMINE-BASED COMPOUND AND ORGANIC LIGHT-EMITTING DIODE INCLUDING THE SAME

CROSS-REFERENCE TO RELATED APPLICATIONS

This application claims priority to and the benefit of Korean Patent Application No. 10-2013-0070487, filed on Jun. 19, 2013, in the Korean Intellectual Property Office, the entire content of which is incorporated herein by reference.

BACKGROUND

1. Technical Field

Embodiments of the present invention relate to an amine-based compound and an organic light-emitting diode including the same.

2. Description of the Related Art

Organic light-emitting diodes (OLEDs) are self-emitting devices having advantages such as wide viewing angles, good contrast, fast response speeds, high brightness, and good driving voltage. Also OLEDs can provide multicolored images.

For example, an OLED may include an anode, a cathode, and an emission layer disposed between the anode and the cathode. A hole transporting region may be included between the anode and the emission layer. An electron transporting region may be included between the emission layer and the cathode. Holes injected from the anode pass through the hole transporting region and move to the emission layer. Electrons injected from the cathode pass through the electron transporting region and move to the emission layer. Carriers, such as the holes or electrons, recombine in the emission layer to generate excitons. When the excitons drop from an excited state to a ground state, light is emitted.

SUMMARY

Embodiments of the present invention are directed toward an amine-based compound and an organic light emitting diode including the amine-based compound.

According to an embodiment of the present invention, an amine-based compound is represented by Formula 1:

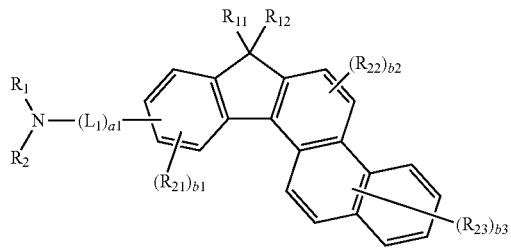

Formula 1

In Formula 1, $L_1$ is selected from a $C_3$-$C_{10}$ cycloalkylene group, a $C_2$-$C_{10}$ heterocycloalkylene group, a $C_3$-$C_{10}$ cycloalkenylene group, a $C_2$-$C_{10}$ heterocycloalkenylene group, a $C_6$-$C_{60}$ arylene group, and a $C_1$-$C_{60}$ heteroarylene group; and a $C_3$-$C_{10}$ cycloalkylene group, a $C_2$-$C_{10}$ heterocycloalkylene group, a $C_3$-$C_{10}$ cycloalkenylene group, a $C_2$-$C_{10}$ heterocycloalkenylene group, a $C_6$-$C_{60}$ arylene group, and a $C_1$-$C_{60}$ heteroarylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and —Si($Q_1$)($Q_2$)($Q_3$) a1 is an integer of 0 to 5, and when a1 is an integer of 2 or more, the two or more $L_1$s are the same or different. $R_1$ and $R_2$ are each independently selected from: a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, and a $C_1$-$C_{60}$ heteroaryl group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, and a $C_1$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and —Si($Q_4$)($Q_5$)($Q_6$); $R_{11}$, $R_{12}$, $R_{21}$, $R_{22}$, and $R_{23}$ are each independently selected from: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a C$_6$-C$_{60}$ arylthio group, a C$_1$-C$_{60}$ heteroaryl group, and —Si(Q$_7$)(Q$_8$)(Q$_9$); wherein Q$_1$ through Q$_9$ are each independently selected from: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, and a C$_1$-C$_{60}$ alkoxy group; and a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, and a C$_1$-C$_{60}$ heteroaryl group; and a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_5$-C$_{60}$ aryl group, a C$_6$-C$_{60}$ aryloxy group, a C$_6$-C$_{60}$ arylthio group, and a C$_1$-C$_{60}$ heteroaryl group; and a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, and a C$_1$-C$_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, and a C$_1$-C$_{60}$ heteroaryl group. b1 is an integer of 1, 2, or 3. b2 is an integer of 1 or 2. b3 is an integer of 1, 2, 3, 4, 5, or 6. When b1, b2, and/or b3 is an integer of 2 or more, the two or more R$_{21}$s, R$_{22}$s, and/or R$_{23}$s are the same or different.

According to another embodiment of the present invention, an organic light-emitting diode includes a first electrode; a second electrode; and an organic layer between the first electrode and the second electrode. The organic layer includes an emission layer and the amine-based compound represented by Formula 1.

BRIEF DESCRIPTION OF THE DRAWINGS

These and/or other aspects of embodiments of the present invention will become apparent by reference to the following detailed description when considered together with the accompanying drawings, in which.

DETAILED DESCRIPTION

Figure 1:
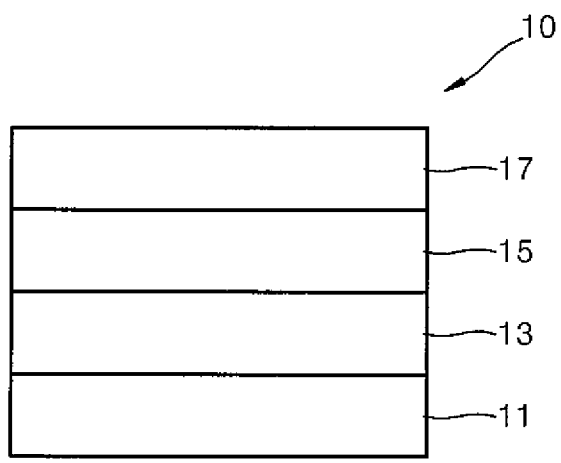
FIG. 1 is a schematic view of an organic light-emitting diode according to an embodiment of the present invention.

In the following detailed description, only certain embodiments of the present invention are shown and described, by way of illustration. As those skilled in the art would recognize, the described embodiments may be modified in different ways, and therefore should not be construed as limiting. Embodiments are also described with reference to the accompanying drawings, in which like reference numerals refer to like elements throughout.

As used herein, the term "and/or," used with a list of elements, includes any and all combinations of one or more of the elements on the list. Expressions such as "at least one of," when preceding a list of elements, modify the entire list of elements and do not modify the individual elements of the list. The use of the term "may" when describing embodiments of the present invention refers to "one or more embodiments of the present invention." In the context of the present application, when a first element is referred to as being "on" a second element, it can be directly on the second element or be indirectly on the second element with one or more intervening elements.

In an embodiment, an amine-based compound is represented by Formula 1:

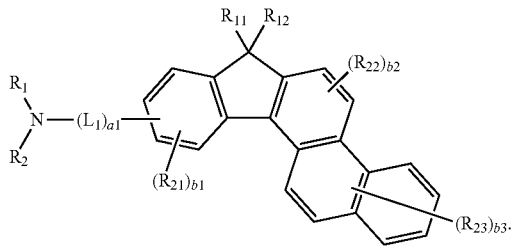

Formula 1

In Formula 1, L$_1$ may be: a C$_3$-C$_{10}$ cycloalkenylene group, a C$_2$-C$_{10}$ heterocycloalkylene group, a C$_3$-C$_{10}$ cycloalkenylene group, a C$_2$-C$_{10}$ heterocycloalkenylene group, a C$_6$-C$_{60}$ arylene group, or a C$_1$-C$_{60}$ heteroarylene group; or a C$_3$-C$_{10}$ cycloalkylene group, a C$_2$-C$_{10}$ heterocycloalkylene group, a C$_3$-C$_{10}$ cycloalkenylene group, a C$_2$-C$_{10}$ heterocycloalkenylene group, a C$_6$-C$_{60}$ arylene group, or a C$_1$-C$_{60}$ heteroarylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, or —Si(Q$_1$)(Q$_2$)(Q$_3$).

According to an embodiment of the present invention, in Formula 1, L$_1$ may be: a phenylene group, a pentalenylene group, an indenylene group, a naphthalene group, an azulenylene group, a heptalenylene group, an indacenylene group, an acenaphthalene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a a triazolylene group, a tetrazolylene group, an oxadiazolylene group, a triazinylene group, a dibenzofuranylene group, a dibenzothiophenylene group, a benzo-carbazolylene group, or a dibenzocarbazolylene group; or a phenylene group, a pentalenylene group, an indenylene group, a naphthalene group, an azulenylene group, a heptalenylene group, an indacenylene group, an acenaphthalene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentapherylenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, or a dibenzocarbazolylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group, but $L_1$ is not limited thereto.

In some embodiments, in Formula 1, $L_1$ may be: a phenylene group, a naphthalene group, a fluorenylene group, a spiro-fluorenylene group, a phenanthrenylene group, an anthracenylene group, a fluoranthrenylene group, a triphenylenylene group, a pyrenylene group, or a chrysenylene group; or a phenylene group, a naphthalene group, a fluorenylene group, a spiro-fluorenylene group, a phenanthrenylene group, an anthracenylene group, a fluoranthrenylene group, a triphenylenylene group, a pyrenylene group, or a chrysenylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group. However, $L_1$ is not limited thereto.

In some embodiments, in Formula 1, $L_1$ may be represented by one of Formulae 2-1 through 2-30:

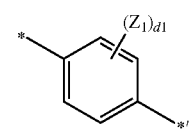

Formula 2-1

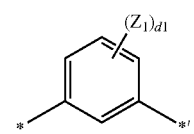

Formula 2-2

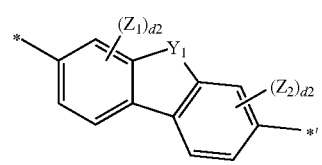

Formula 2-3

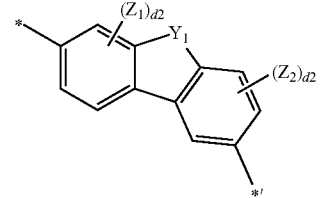

Formula 2-4

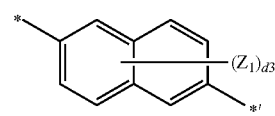

Formula 2-5

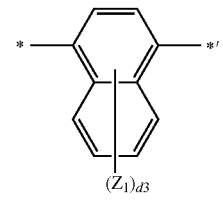

Formula 2-6

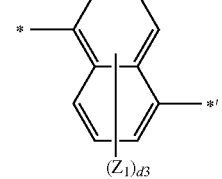

Formula 2-7

-continued
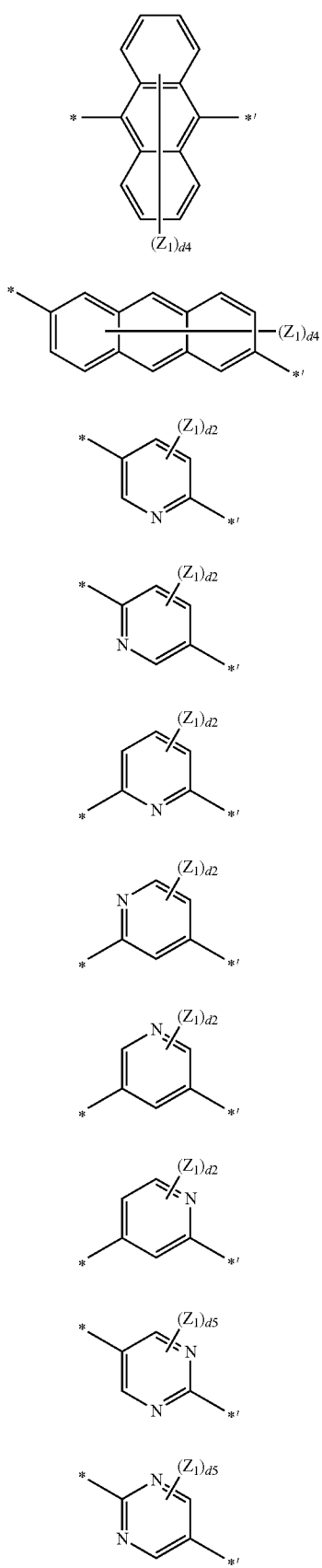
Formula 2-8
Formula 2-9
Formula 2-10
Formula 2-11
Formula 2-12
Formula 2-13
Formula 2-14
Formula 2-15
Formula 2-16
Formula 2-17
-continued
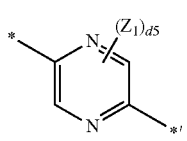
Formula 2-18
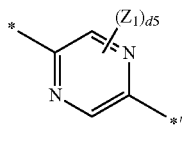
Formula 2-19
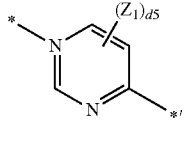
Formula 2-20
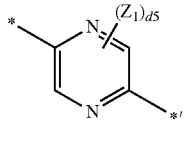
Formula 2-21
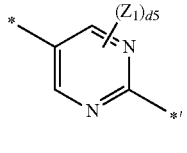
Formula 2-22
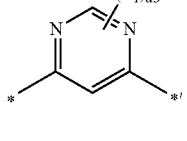
Formula 2-23
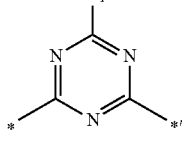
Formula 2-24
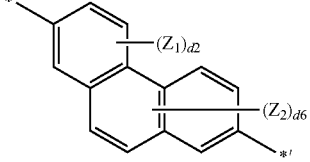
Formula 2-25
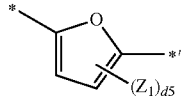
Formula 2-26
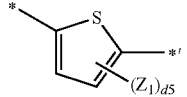
Formula 2-27

Formula 2-28

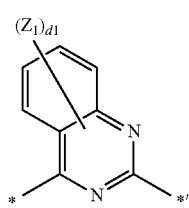

Formula 2-29

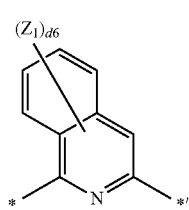

Formula 2-30

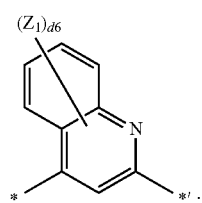

In Formulae 2-1 through 2-30, $Y_1$ may be O, S, S(=O), S(=O)$_2$, C($Z_3$)($Z_4$), N($Z_5$), or Si($Z_6$)($Z_7$); and $Z_1$ through $Z_7$ may each independently be a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, —N($Q_{11}$)($Q_{12}$), or —Si($Q_{13}$)($Q_{14}$)($Q_{15}$) In Formulae 2-1 through 2-30, d1 is an integer of 1 to 4; d2 is an integer of 1 to 3; d3 is an integer of 1 to 6; d4 is an integer of 1 to 8; d5 is an integer of 1 or 2; d6 is an integer of 1 to 5 and when d1, d2, d3, d4, d5, and/or d6 is an integer of 2 or more, the two or more $Z_1$s and/or $Z_2$s are the same or different. In Formulae 2-1 through 2-30, * and *' are each a binding site to the nitrogen (N) atom of Formula 1, to a corresponding atom of Formula 1, or to another $L_1$ For example, in Formulae 2-1 through 2-30, * may be a binding site to the core in Formula 1 or may be a binding site to a neighboring $L_1$. As a further example, in Formulae 2-1 through 2-30, *' may be a binding site to a neighboring $L_1$ or to the nitrogen atom (N) in Formula 1.

In Formulae 2-1 through 2-30, $Z_1$ through $Z_7$ may each independently be a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group. However, $Z_1$ through $Z_7$ are not limited thereto.

In some embodiments, in Formula 1, $L_1$ may be represented by one of Formulae 3-1 through 3-19, but $L_1$ is not limited thereto:

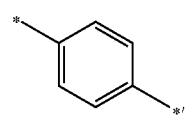

Formula 3-1

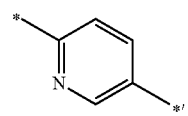

Formula 3-2

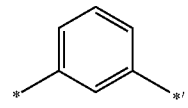

Formula 3-3

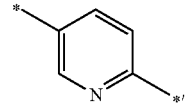

Formula 3-4

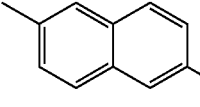

Formula 3-5

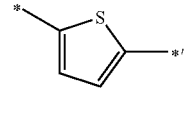

Formula 3-6

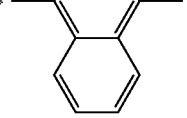

Formula 3-7

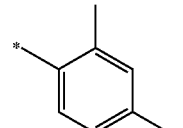

Formula 3-8

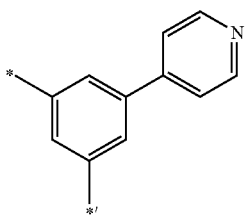

Formula 3-9

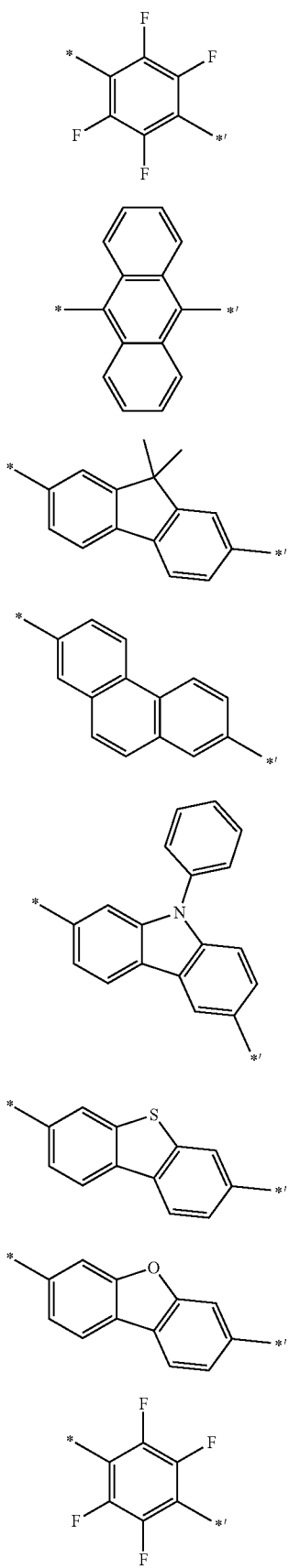

Formula 3-10

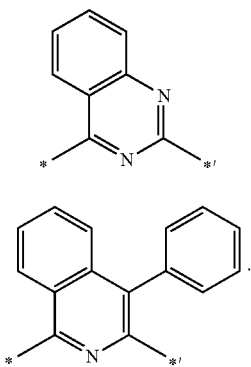

Formula 3-11

Formula 3-12

Formula 3-13

Formula 3-14

Formula 3-15

Formula 3-16

Formula 3-17

Formula 3-18

Formula 3-19

In Formula 1, a1 is the number of $L_1$s, which may be 0, 1, 2, 3, 4, or 5, for example, 0, 1, or 2, or for example, 0 or 1. When a1 is 0, the nitrogen (N) of Formula 1 is directly bonded to the core of Formula 1. When a1 is 2 or greater, the two or more $L_1$s may be identical to or different from each other.

In Formula 1, $R_1$ and $R_2$ may each independently be: a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, or a $C_1$-$C_{60}$ heteroaryl group; or a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, or a $C_1$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_5$-$C_{60}$ aryloxy group, a $C_6$-$C_{60}$ arylthio group, a $C_1$-$C_{60}$ heteroaryl group, or —Si($Q_4$)($Q_5$)($Q_6$).

In Formula 1, $R_{11}$, $R_{12}$, $R_{21}$, $R_{22}$, and $R_{23}$ may each independently be: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group; or a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group; or a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group; or a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, or —$Si(Q_7)(Q_8)(Q_9)$.

According to embodiments of the present disclosure, $Q_1$ through $Q_9$ may each independently be: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group; or a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group; or a $C_3$-$C_{10}$ cycloalkyl group, a $C_2$-$C_{10}$ heterocycloalkyl group, a $C_2$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group; or a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group.

In some embodiments, in Formula 1, $R_1$ and $R_2$ may each independently be: a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, or a dibenzocarbazolyl group; or a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyi group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, or a dibenzocarbazolyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, a quinazolinyl group, or —$Si(Q_4)(Q_5)(Q_6)$. According to embodiments of the present disclosure, $Q_4$ through $Q_6$ may each be independently be a hydrogen atom, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group.

In some embodiments, in Formula 1, $R_{11}$, $R_{12}$, $R_{21}$, $R_{22}$, and $R_{23}$ may each independently be: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a $C_1$-$C_{20}$ alkoxy group; or a $C_1$-$C_{20}$ alkyl group or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, or a dibenzocarbazolyl group; or a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, or a dibenzocarbazolyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, a quinazolinyl group, or —Si($Q_7$)($Q_8$)($Q_9$). According to embodiments of the present disclosure, $Q_7$ through $Q_9$ may each be independently a hydrogen atom, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group.

For example, in Formula 1, $R_1$ and $R_2$ may each independently be a group represented by one of Formulae 4-1 through 4-29. $R_{11}$, $R_{12}$, $R_{21}$, $R_{22}$, and $R_{23}$ may each independently be: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a $C_1$-$C_{20}$ alkoxy group; or a $C_1$-$C_{20}$ alkyl group or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthryl group, a fluorenyl group, a carbazolyl group, a pyridinyl group, a pyrimidinyl group, a triazinyl group, a quinolinyl group, an isoquinolinyl group, or a quinazolinyl group; or a group represented by one of Formulae 4-1 through 4-29. However, $R_1$, $R_2$, $R_{11}$, $R_{12}$, $R_{21}$, $R_{22}$, and $R_{23}$ are not limited thereto:

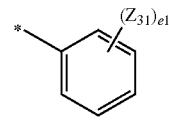

Formula 4-1

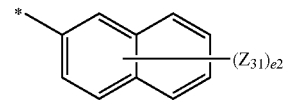

Formula 4-2

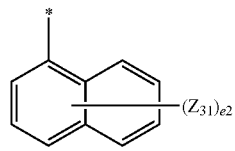

Formual 4-3

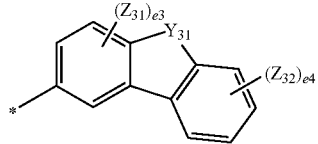

Formula 4-4

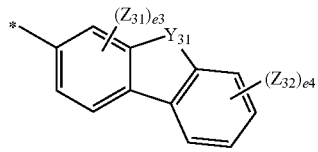

Formula 4-5

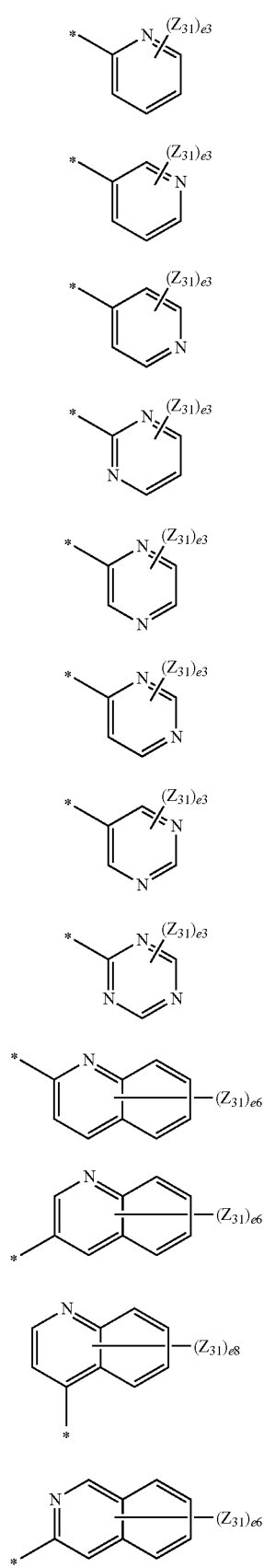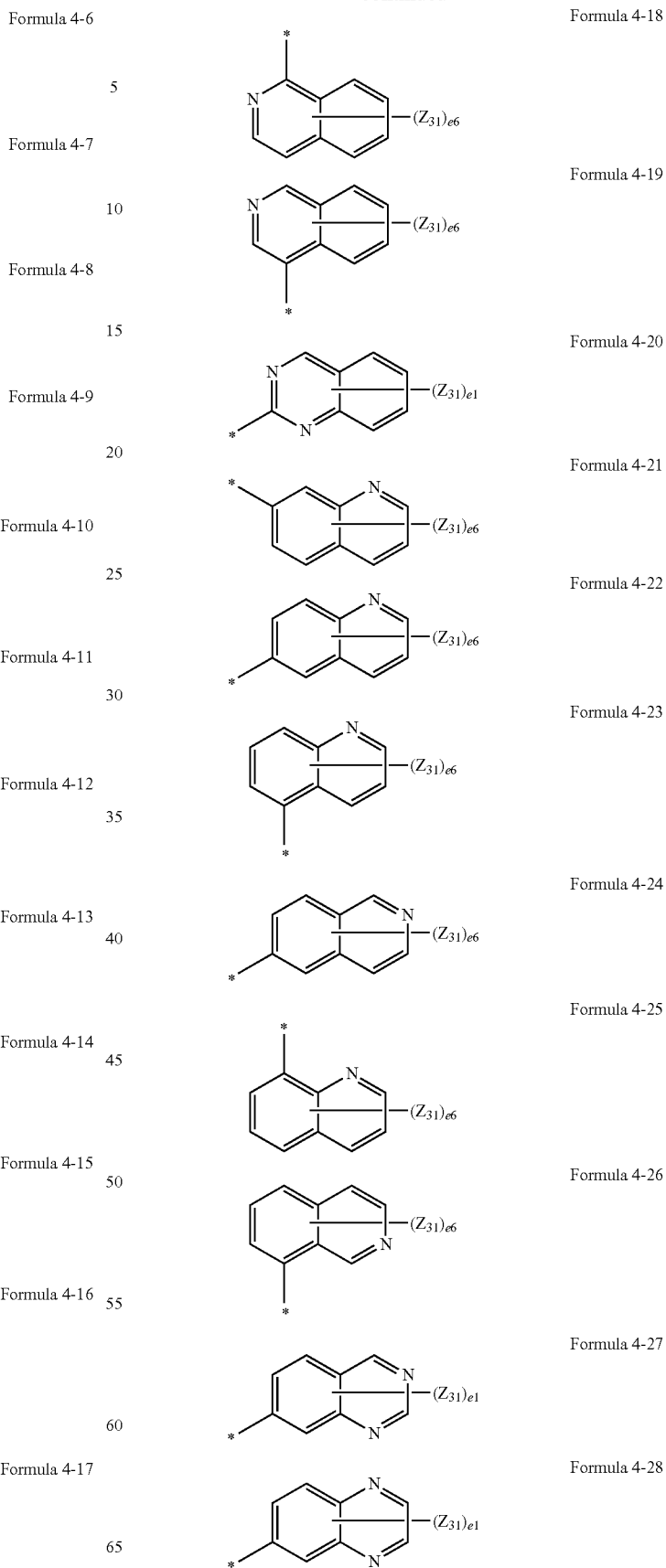

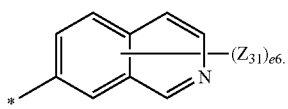

Formula 4-29

In Formulae 4-1 through 4-29, $Y_{31}$ is O, S, $C(Z_{33})(Z_{34})$, $N(Z_{35})$ or $Si(Z_{36})(Z_{37})$. In Formulae 4-1 through 4-29, $Z_{31}$ through $Z_{37}$ are each independently a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, or —Si($Q_{11}$)($Q_{12}$)($Q_{13}$).

According to embodiments of the present disclosure, $Q_{11}$ through $Q_{13}$ are each independently a hydrogen atom, a $C_1$-$C_{60}$ alkyl group, a $C_1$-$C_{20}$ alkoxy group, a $C_6$-$C_{60}$ aryl group, or a $C_1$-$C_{60}$ heteroaryl group.

In Formulae 4-1 through 4-29, e1 is an integer of 1 to 5; e2 is an integer of 1 to 7; e3 is an integer of 1 to 3; e4 is an integer of 1 to 4; e5 is an integer of 1 or 2; e6 is an integer of 1 to 6. In Formulae 4-1 through 4-29, when e1, e2, e3, e4, e5, and/or e6 is an integer of 2 or more, the two or more $Z_{31}$s and/or $Z_{32}$s are the same or different, and * is a binding site to a corresponding atom of Formula 1.

For example, in Formulae 4-1 through 4-29, $Z_{31}$ through $Z_{37}$ may each independently be a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, a quinazolinyl group, or —Si($Q_{11}$)($Q_{12}$)($Q_{13}$).

According to embodiments of the present disclosure, $Q_{11}$ through $Q_{13}$ are each independently a hydrogen atom, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group, but $Z_{31}$ through $Z_{37}$ are not limited thereto.

For example, in Formulae 4-1 through 4-29, e1, e2, e3, e4, e5, and e6 may each independently be 1 or 2.

In some embodiments, in Formula 1, $R_1$ and $R_2$ may each independently be a group represented by one of Formulae 5-1 through 5-21. $R_{11}$, $R_{12}$, $R_{21}$, $R_{22}$, and $R_{23}$ may each independently be: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a $C_1$-$C_{20}$ alkoxy group; or a $C_1$-$C_{20}$ alkyl group or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a pyridinyl group, a pyrimidinyl group, a triazinyl group, a quinolinyl group, an isoquinolinyl group, or a quinazolinyl group; or a group represented by one of Formulae 5-1 through 5-21. However, $R_1$, $R_2$, $R_{11}$, $R_{12}$, $R_{21}$, $R_{22}$, and $R_{23}$ are not limited thereto:

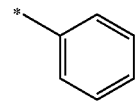

Formula 5-1

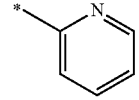

Formula 5-2

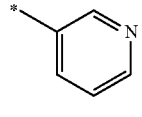

Formula 5-3

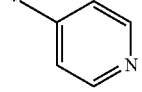

Formula 5-4

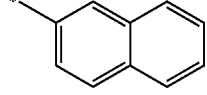

Formula 5-5

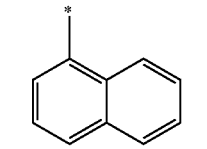

Formula 5-6

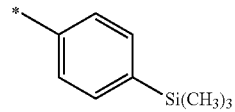

Formula 5-7

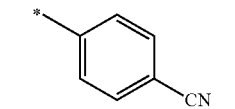

Formula 5-8

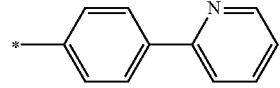

Formula 5-9

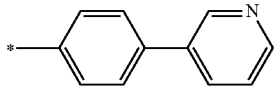

Formula 5-10

In Formula 1, b1 is the number of $R_{21}$s, which may be an integer of 1 to 3. b1 may be 1 or 2, or for example, may be 1. When b1 is 2 or more, the two or more $R_{21}$s may be the same or different.

In Formula 1, b2 is the number of $R_{22}$s, which may be an integer of 1 or 2, for example, b2 may be 1. When b1 is 2, the two $R_{22}$s may be the same or different.

In Formula 1, b3 is the number of $R_{23}$s, which may be an integer of 1 to 6. When b3 is 2 or more, the two or more $R_{23}$s may be the same or different.

In Formula 1, $R_{11}$ and $R_{12}$ may each independently be: a $C_1$-$C_{20}$ alkyl group or a $C_1$-$C_{20}$ alkoxy group; or a $C_1$-$C_{20}$ alkyl group or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group.

In some embodiments, in Formula 1, $R_{11}$ and $R_{12}$ may be identical to each other. For example, in Formula 1, both $R_{11}$ and $R_{12}$ may be a methyl group or a phenyl group.

In Formula 1, all of $R_{21}$, $R_{22}$, and $R_{23}$ may be hydrogen atoms.

The amine-based compound may be represented by Formula 1A:

Formula 1A

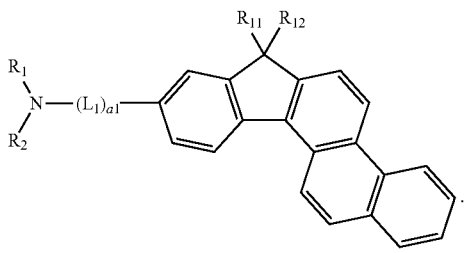

In Formula 1A, $L_1$, a1, $R_1$, $R_2$, $R_{11}$, and $R_{12}$ are the same as those already described in connection with Formula 1.

For example, in Formula 1A, $L_1$ may be represented by one of Formulae 2-1 through 2-30. a1 may be an integer of 0 or 1. $R_1$ and $R_2$ may each independently be represented by one of Formulae 4-1 through 4-29. $R_{11}$ and $R_{12}$ may each independently be: a $C_1$-$C_{20}$ alkyl group or a $C_1$-$C_{20}$ alkoxy group; or a $C_1$-$C_{20}$ alkyl group or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group. However, Formula 1A is not limited thereto.

In some embodiments, in Formula 1A, $L_1$ may be represented by one of Formulae 3-1 through 3-19; a1 may be 0 or 1; $R_1$ and $R_2$ may each independently be represented by one of Formulae 5-1 through 5-21; $R_{11}$ and $R_{12}$ may each independently be a $C_1$-$C_{20}$ alkyl group, a $C_1$-$C_{20}$ alkoxy group, a phenyl group, a naphthyl group, an anthracenyl group, a pyrenyl group, or a phenanthrenyl group. However, Formula 1A is not limited thereto.

In some embodiments, the amine-based compound may be represented by one of Formulae 1A(1) through 1A(6):

Formula 1A(1)

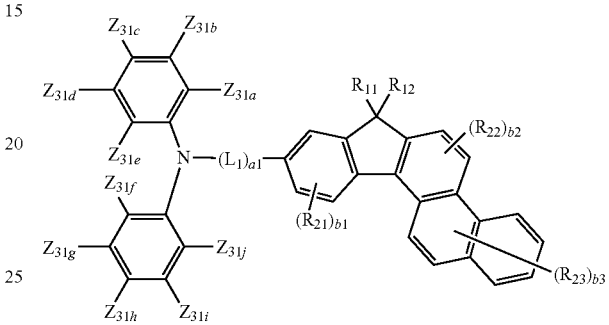

Formula 1A(2)

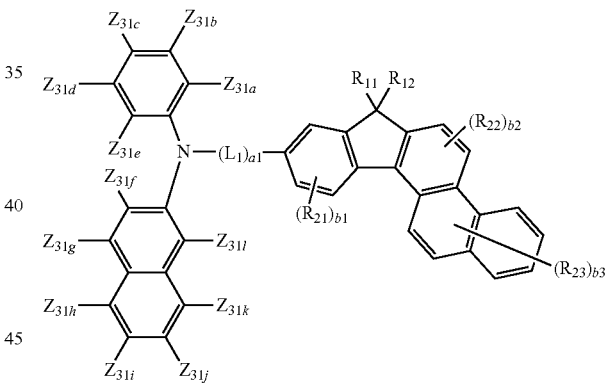

Formula 1A(3)

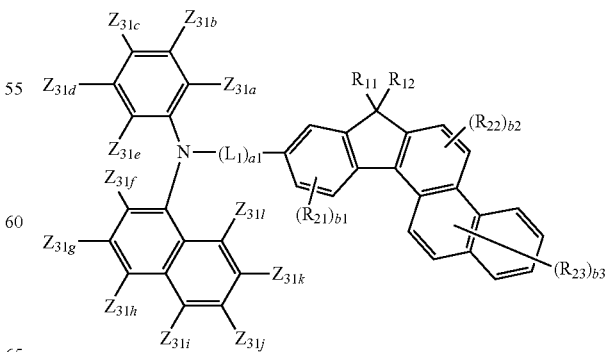

-continued

Formula 1A(4)

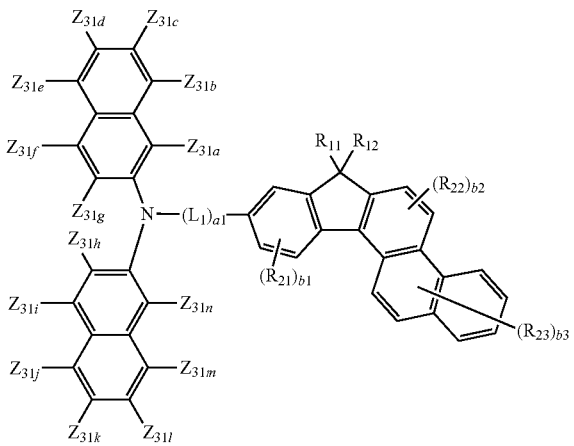

Formula 1A(5)

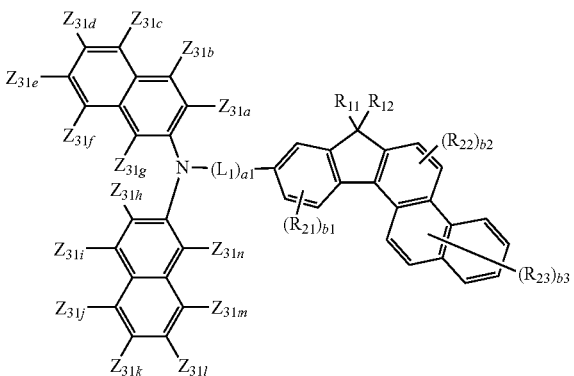

Formula 1A(6)

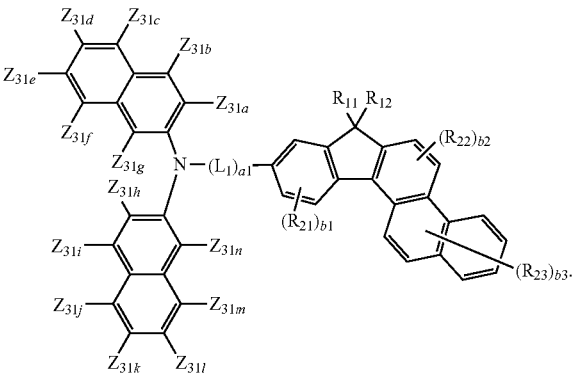

In Formulae 1A(1) through 1A(6), $L_1$, a1, $R_{11}$, $R_{12}$, $R_{21}$, $R_{22}$, $R_{23}$, b1, b2, and b3 are the same as those already described in connection with Formula 1. In Formulae 1A(1) through 1A(6), $Z_{31a}$ through $Z_{31n}$ may each independently be a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and —Si($Q_4$)($Q_5$)($Q_6$), wherein $Q_4$ through $Q_6$ are each independently selected from a hydrogen atom, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, or a $C_1$-$C_{60}$ heteroaryl group.

For example, in Formulae 1A(1) through 1A(6), $L_1$ may be a phenylene group, a naphthalene group, a fluorenylene group, a spiro-fluorenylene group, a phenanthrenylene group, an anthracenylene group, a fluoranthrenylene group, a triphenylenylene group, a pyrenylene group, or a chrysenylene group; or a phenylene group, a naphthalene group, a fluorenylene group, a spiro-fluorenylene group, a phenanthrenylene group, an anthracenylene group, a fluoranthrenylene group, a triphenylenylene group, a pyrenylene group, or a chrysenylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group. a1 may be an integer of 0 or 1.

In Formulae 1A(1) through 1A(6), $R_{11}$ and $R_{12}$ may each independently be: a $C_1$-$C_{20}$ alkyl group or a $C_1$-$C_{20}$ alkoxy group; or a $C_1$-$C_{20}$ alkyl group or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group.

In Formulae 1A(1) through 1A(6), $R_{21}$, $R_{22}$, and $R_{23}$ may each independently be a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a $C_1$-$C_{20}$ alkoxy group; or a $C_1$-$C_{20}$ alkyl group or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group; or a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, or a quinazolinyl group.

In Formulae 1A(1) through 1A(6), b1, b2, and b3 may each independently be 1 or 2, but b1, b2, and b3 are not limited thereto.

The amine-based compound may be one of Compounds 1 through 15:

1

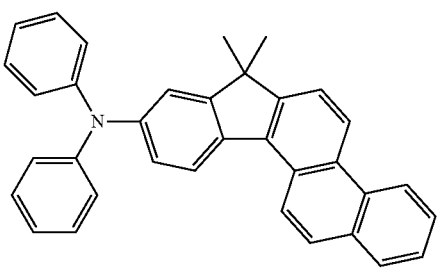

-continued

2

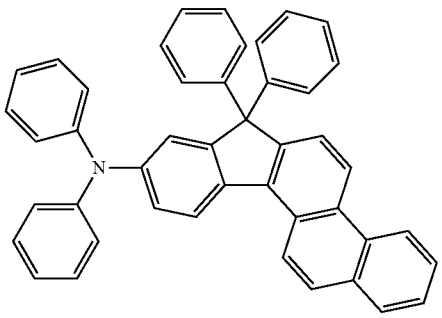

3

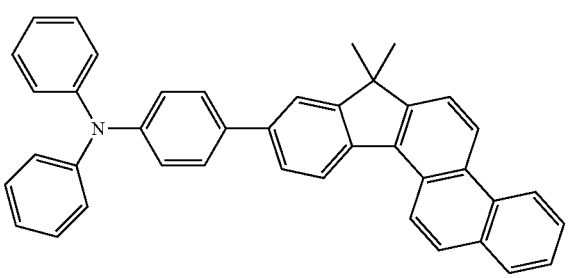

4

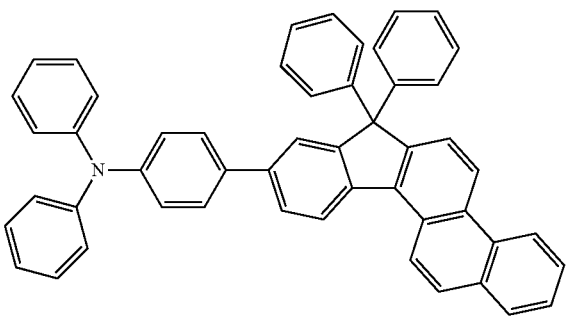

5

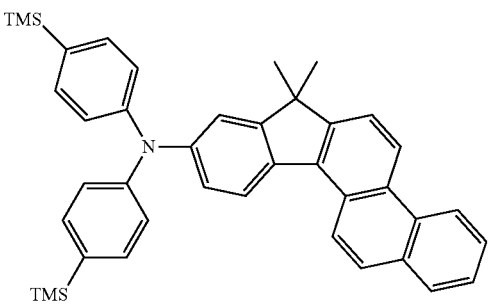

6

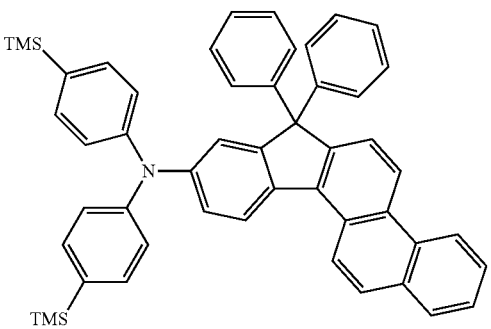

-continued

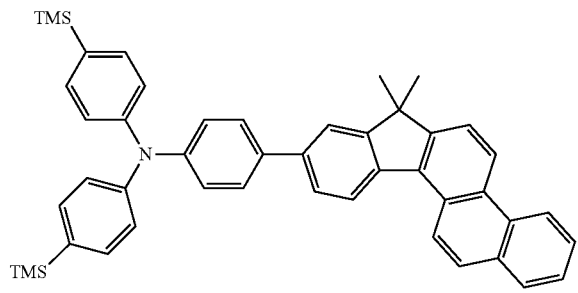
7

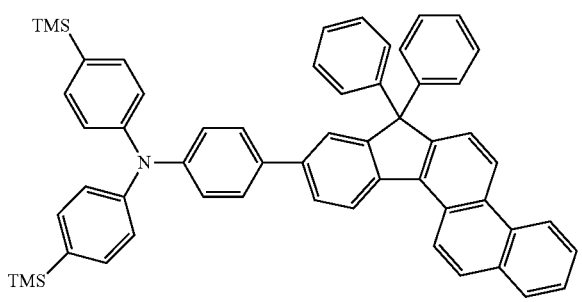
8

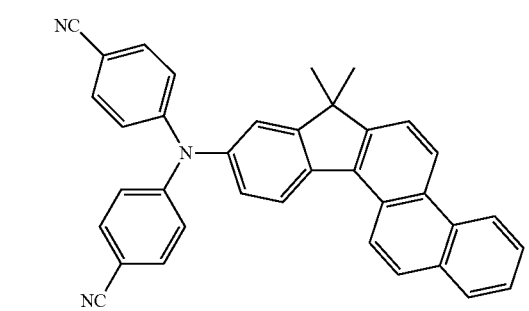
9

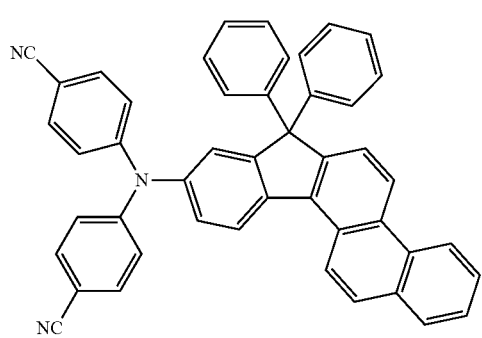
10

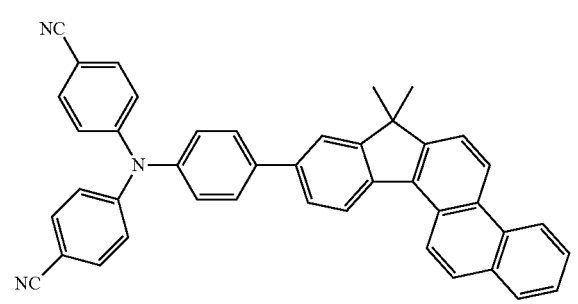
11

-continued

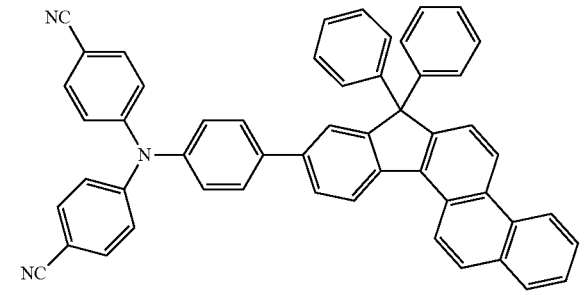
12

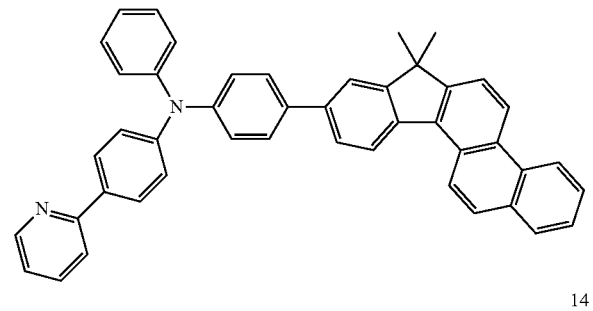
13

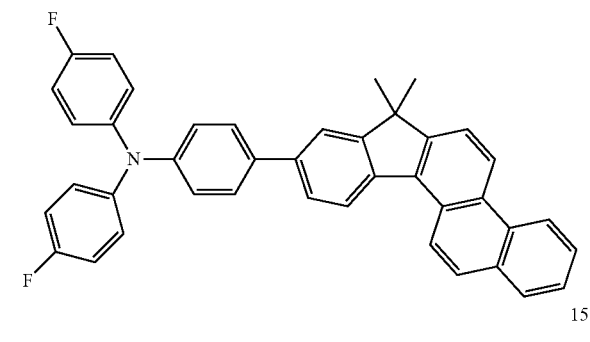
14

15

In some embodiments, in the amine-based compound represented by Formula 1, $-N(R_1)(R_2)$ is only bonded to "a benzo group" of the core in Formula 1, optionally with $-(L_1)_{a1}$ therebetween. In these embodiments, an OLED including the amine-based compound represented by Formula 1 may have good color purity. For example, an organic light-emitting diode (OLED) including the amine-based compound represented by Formula 1 may emit blue light (e.g., blue light that is shifted to a green light region and has a relatively short wavelength).

Also, according to embodiments of the present invention, the amine-based compound represented by Formula 1, includes a core which includes a naphthalene ring condensed with a fluorene ring. According to embodiments of the present invention, the OLED including the amine-based compound represented by Formula 1 may have a low driving voltage and high emission efficiency of short-wavelength (e.g., blue) light.

According to some embodiments, in the amine-based compound represented by Formula 1, —N(R$_1$)(R$_2$) is either directly connected to the core (a1=0) or includes an L$_1$ therebetween (a1≠0). Here, L$_1$ is a divalent cyclic group. That is, according to embodiments, a styryl group is not included in L$_1$ in Formula 1. An amine-based compound including a styryl group may be thermally polymerized during deposition, and a polymer derived from the amine-based compound including the styryl group may be formed. The polymer is included in the layer formed by the deposition of the amine-based compound including a styryl group, and thus layer formation efficiency of the amine-based compound including a styryl group may be deteriorated, and a loss rate of the material used for the formation of the layer increases. However, according to embodiments of the present disclosure, the amine-based compound represented by Formula 1 has high thermal stability, high layer formation efficiency, and a low material loss rate. Thus, the processing cost for manufacturing an OLED including the amine-based compound represented by Formula 1 may be reduced.

Synthesis Examples 1 through 8 (described below) illustrate embodiments of methods of synthesizing amine-based compounds represented by Formula 1.

In some embodiments, the amine-based compound represented by Formula 1 is a suitable dopant for an organic layer (e.g., an emission layer of the organic layer).

According to an embodiment of the present invention, an OLED includes a first electrode; a second electrode; and an organic layer between the first electrode and the second electrode. The organic layer includes an emission layer. The organic layer includes at least one of the amine-based compounds represented by Formula 1.

Therefore, in some embodiments, the OLED including the amine-based compound represented by Formula 1 may have good color purity, low driving voltage, high efficiency, high brightness, and/or a long lifetime.

The amine-based compound represented by Formula 1 may be used between a pair of electrodes of an OLED. For example, the amine-based compound may be included in at least one of the emission layer (EML), a hole transporting region between the EML and the first electrode, and an electron transporting region between the EML and the second electrode. The hole transporting region may include at least one of a hole injection layer (HIL), a hole transport layer (HTL), and/or an electron blocking layer (EBL). The electron transporting region may include at least one of a hole blocking layer (HBL), an electron transport layer (ETL), and/or an electron injection layer (EIL). For example, the amine-based compound represented by Formula 1 may be included in at least one of the emission layer, the hole transporting region, and/or the electron transporting region.

According to embodiments of the present invention, the amine-based compound represented by Formula 1 may be included in the emission layer of the OLED. In these embodiments, the amine-based compound may be a fluorescent dopant. For example, the amine-based compound may be a dopant that emits blue light by a fluorescence mechanism. The EML may further include a host. The host may include any suitable material commonly used as a host. For example, the host may include an anthracene-based compound (e.g., the compound represented by one of Formulae 400 or 401, described below).

According to embodiments of the present invention, the organic layer may include at least one of the amine-based compound of Formula 1. That is, it will be understood that the organic layer may include one of the amine-based compound represented by Formula 1 or at least two different amine-based compounds represented by Formula 1.

For example, the organic layer may include only Compound 1 as the amine-based compound. In this regard, Compound 1 may be included in the EML of the OLED. As a further example, the organic layer may include Compound 1 and Compound 2 as the amine-based compound. In this regard, Compounds 1 and 2 may be included in the same layer (e.g., both Compounds 1 and 2 may be included in the EML) or in different layers.

The first electrode may be an anode, i.e., a hole injection electrode, and the second electrode may be a cathode, i.e., an electron injection electrode. Alternatively, the first electrode may be the cathode, i.e., an electron injection electrode, and the second electrode may be the anode, i.e., a hole injection electrode.

For example, the first electrode may be the anode, and the second electrode may be the cathode. The organic layer may include a hole transporting region between the first electrode and the EML. The hole transporting region may include at least one of a HIL, a HTL, and/or an EBL. The organic layer may also include an electron transporting region between the EML and the second electrode. The electron transporting region may include at least one of a HBL, an ETL, and/or an EIL.

The organic layer may include a single layer, or may include multiple layers, between the first electrode and the second electrode in the OLED. The organic layer may include an organic metal complex.

FIG. 1 is a schematic cross-sectional view of an OLED 10 according to an embodiment of the present invention. Hereinafter, a structure and a manufacturing method of the OLED 10 will be described in more detail with reference to FIG. 1. The OLED 10 includes a substrate 11, a first electrode 13, an organic layer 15, and a second electrode 17, which are sequentially stacked.

The substrate 11 may be any suitable substrate commonly used in an OLED, such as a glass substrate or a transparent plastic substrate having suitable mechanical strength, thermal stability, transparency, surface smoothness, ease of handling, and/or waterproofness.

The first electrode 13 may be formed by applying a first electrode material on the substrate 11 by deposition or sputtering. When the first electrode 13 is an anode, the first electrode material may be a material having a high work function to facilitate hole injection. The first electrode 13 may be a reflective electrode or a transparent electrode.

Non-limiting examples of the first electrode material include indium-tin oxide (ITO), Indium-zinc-oxide (IZO), tin oxide (SnO$_2$), and zinc oxide (ZnO). In embodiments where the first electrode material includes magnesium (Mg), aluminum (Al), aluminum-lithium (Al—Li), calcium (Ca), magnesium-indium (Mg—In), or magnesium-silver (Mg—Ag), the first electrode 13 may be formed as a reflective electrode.

The first electrode 13 may be formed as a single layer structure or as a multi-layered structure having at least two layers. For example, the first electrode 13 may have a three-layered structure, such as ITO/Ag/ITO, but the first electrode 13 is not limited thereto.

An organic layer 15 is formed on the first electrode 13.

The organic layer 15 may include a hole transporting region sequentially including a HIL and a HTL; and an electron transport region sequentially including an ETL and an EIL.

The HIL may be formed on the first electrode 13 using various suitable methods commonly used to form an HIL, such as vacuum deposition, spin coating, casting, or LB deposition. When the HIL is formed by vacuum deposition, the deposition conditions may vary according to the compound used for forming the HIL and the structural and thermal characteristics of the desired HIL. For example, the deposition conditions may include using a deposition temperature of about 100° C. to about 500° C., a degree of vacuum of about $10^{-8}$ to about $10^{-3}$ torr, and a deposition speed of about 0.01 Å/sec to about 100 Å/sec, but the conditions are not limited thereto.

When the HIL is formed by spin coating, the coating conditions may vary according to the compound used for forming the HIL, and the structural and thermal characteristics of the desired HIL. For example, the coating conditions may include using a coating speed of about 2,000 rpm to about 5,000 rpm and a heat treatment temperature for removing solvent after coating of about 80° C. to about 200° C., but the conditions are not limited there to.

The material for forming the HIL may be any commonly used hole injection material. Non-limiting examples of the hole injection material include N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), N,N'-di(1-naphthyl)-N,N'-diphenylbenzidine (NPB), TDATA, 2-TNATA, polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), and polyaniline/poly(4-styrenesulfonate) (PANI/PSS):

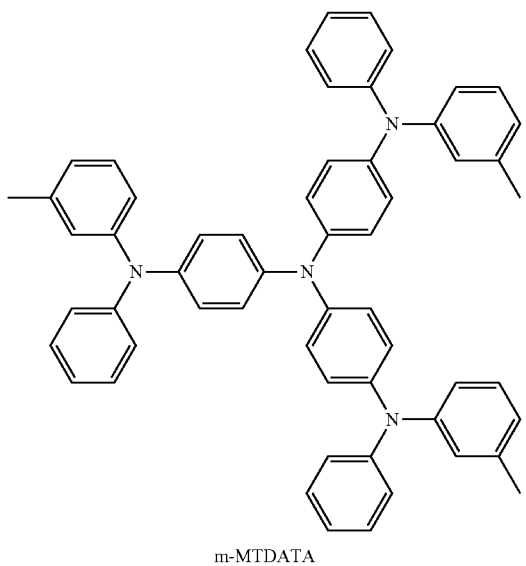

m-MTDATA

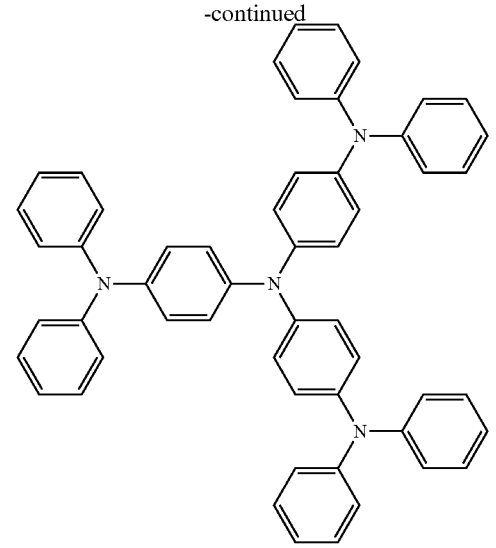

TDATA

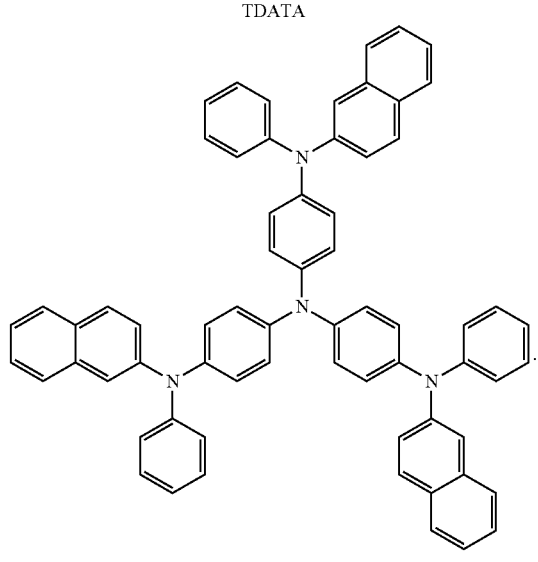

2-TNATA

In some embodiments, the thickness of the HIL may be about 100 Å to about 10,000 Å, for example, about 100 Å to about 1,000 Å. In these embodiments, suitable hole injection properties may be obtained without a substantial increase in driving voltage.

An HTL may be formed on the HIL using various suitable methods for forming a HTL, such as vacuum deposition, spin coating, casting, or LB deposition. When the HTL is formed by vacuum deposition or spin coating, the deposition or coating conditions vary according to the compound used to form the HTL. The conditions for forming the HTL may be similar to the conditions for forming the HIL.

Non-limiting examples of the material for forming the HTL include: carbazole derivatives such as N-phenylcarbazole and polyvinylcarbazole, N,N'-bis(3-methylphenyl)-N,N'-diphenyl-[1,1-biphenyl]-4,4'-diamine (TPD), 4,4',4"-tris (N-carbazolyl)triphenylamine (TCTA), and N,N'-di(1-naphthyl)-N,N'-diphenylbenzidine (NPB)

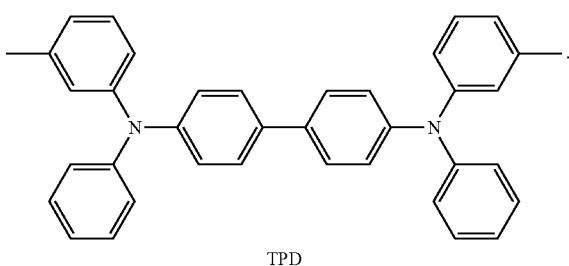

TPD

In some embodiments, the thickness of the HTL may be about 50 Å to about 2,000 Å, for example, about 100 Å to about 1,500 Å. In these embodiments, suitable hole transport properties may be obtained without a substantial increase in driving voltage.

At least one of the HIL or the HTL may include at least one of the compound represented by Formula 300 or the compound represented by Formula 301:

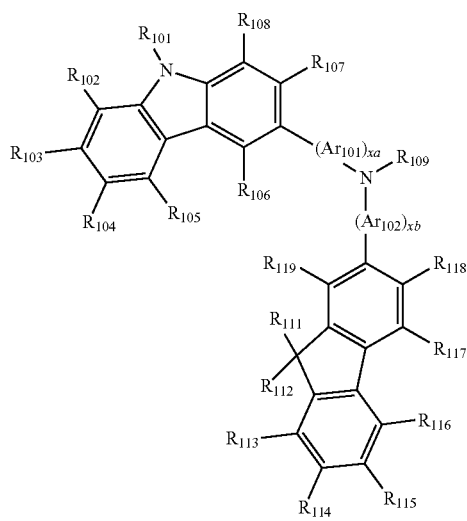

Formula 300

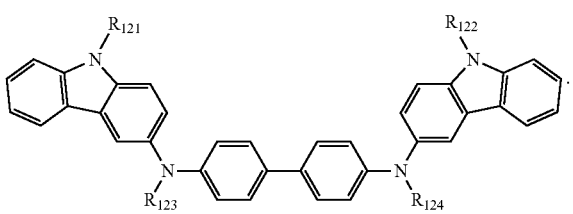

Formula 301

In Formula 300, $Ar_{101}$ and $Ar_{102}$ may each independently be: a phenylene group, a pentalenylene group, an indenylene group, a naphthylene group, an azulenylene group, a heptalenylene group, an acenaphthylene group, a fluorenylene group, phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, or a pentacenylene group; or a phenylene group, a pentalenylene group, an indenylene group, a naphtylene group, an azulenylene group, a heptalenylene group, an acenaphtylene group, a fluorenylene group, phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, or a pentacenylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_1$-$C_{60}$ heteroaryl group. However, $Ar_{101}$ and $Ar_{102}$ are not limited thereto.

In Formula 300, xa and xb may each independently be an integer of 0 to 5, for example, 0, 1, or 2. For example, xa may be 1, and xb may be 0, but xa and xb are not limited thereto.

In Formulae 300 and 301, $R_{101}$ through $R_{108}$, $R_{111}$ through $R_{119}$, and $R_{121}$ through $R_{124}$ may each independently be: a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, a pentyl group, a hexyl group, etc.), or a $C_1$-$C_{10}$ alkoxy group (e.g., a methoxy group, an ethoxy group, a propoxy group, a butoxy group, a pentoxy group, etc.); or a $C_1$-$C_{10}$ alkyl group or a $C_1$-$C_{10}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, or a phosphoric acid group or a salt thereof; or a phenyl group, a naphthyl group, an anthracenyl group, a fluorenyl group, or a pyrenyl group; or a phenyl group, a naphthyl group, an anthracenyl group, a fluorenyl group, or a pyrenyl group, each substituted with at least one of a $C_1$-$C_{10}$ alkyl group and a $C_1$-$C_{10}$ alkoxy group. However, $R_{101}$ through $R_{108}$, $R_{111}$ through $R_{119}$, and $R_{121}$ through $R_{124}$ are not limited thereto.

In Formula 300, $R_{109}$ may be: a phenyl group, a naphthyl group, an anthracenyl group, a biphenyl group, or a pyridinyl group; or a phenyl group, a naphthyl group, an anthracenyl group, a biphenyl group, or a pyridinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, or a $C_1$-$C_{20}$ alkoxy group.

In some embodiments, the compound of Formula 300 may be represented by Formula 300A, but the compound of Formula 300 is not limited thereto:

Formula 300A
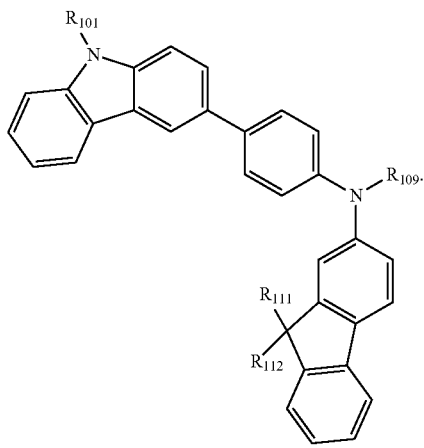
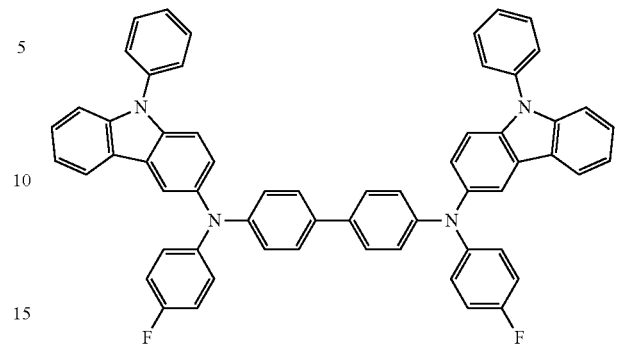
303
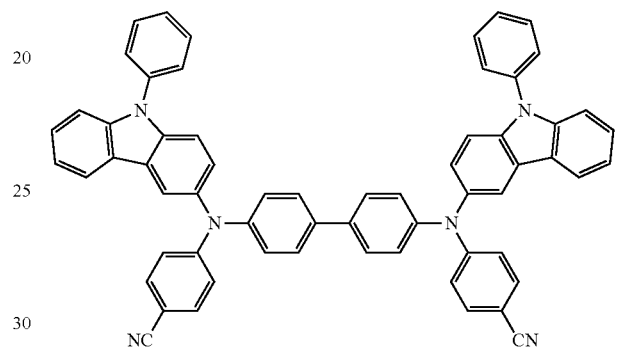
304
In Formula 300A, $R_{101}$, $R_{111}$, $R_{112}$, and $R_{109}$ are the same as those already described in connection with Formula 1.
In some embodiments, at least one of the HIL or the HTL may include at least one of Compounds 301 through, 320, but the HTL is not limited thereto:
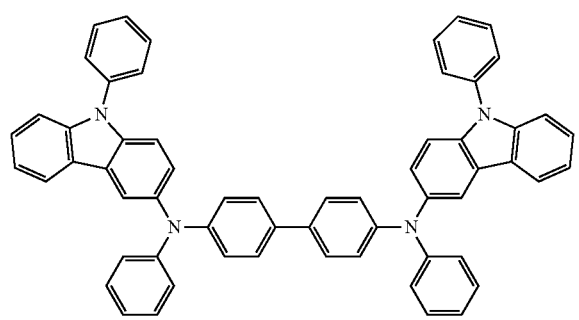
301
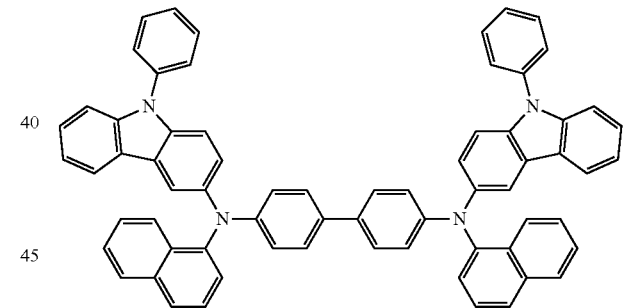
305
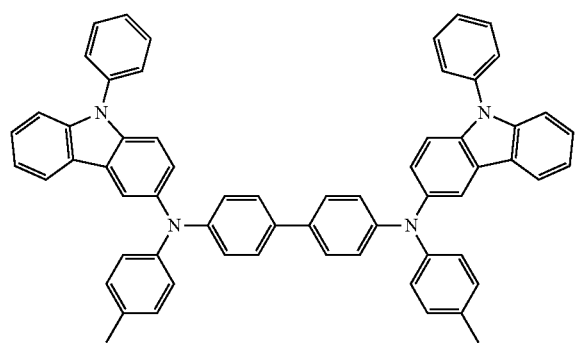
302
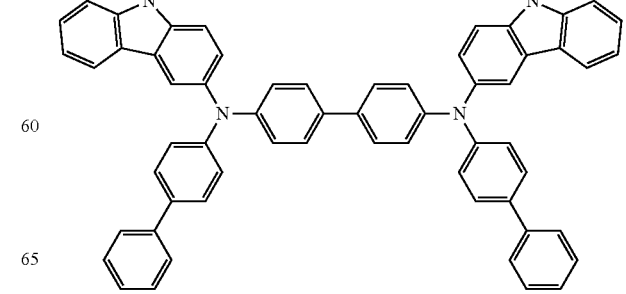
306

307
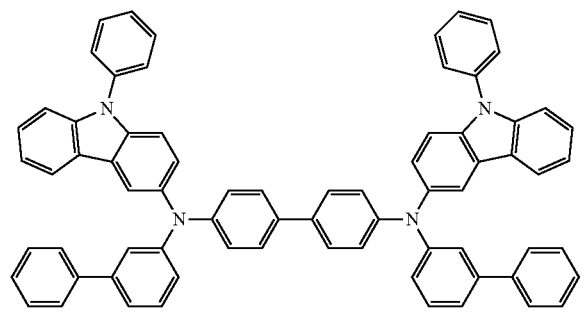
308
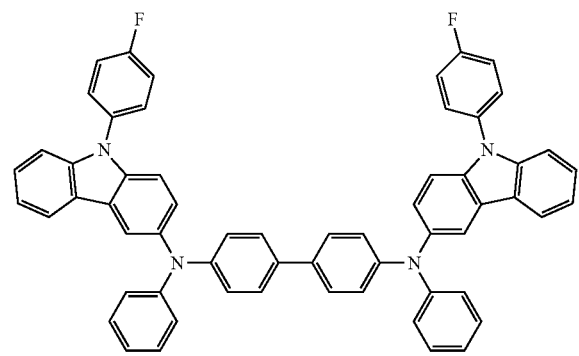
309
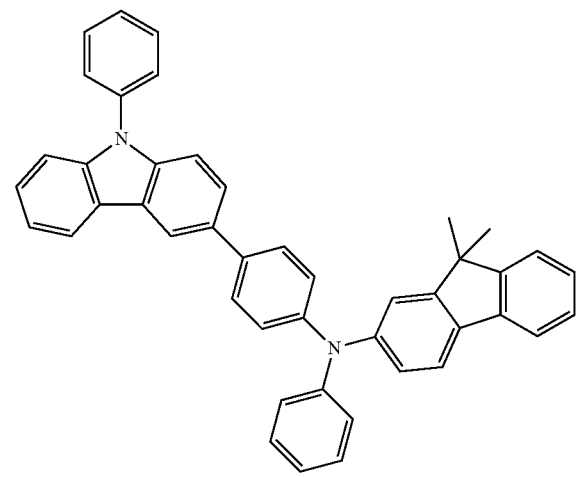
310
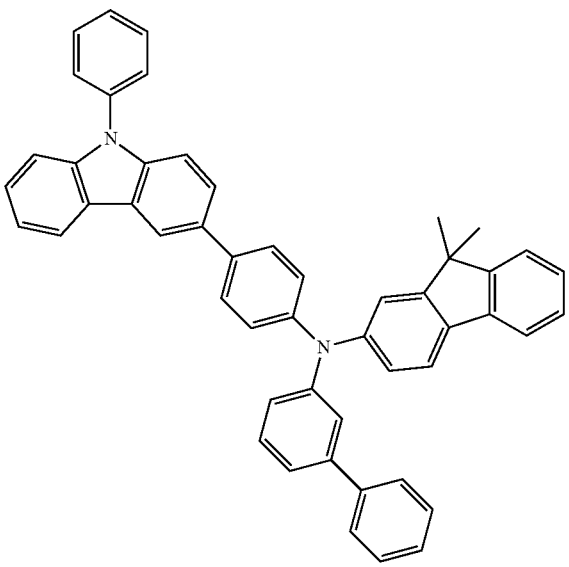
311
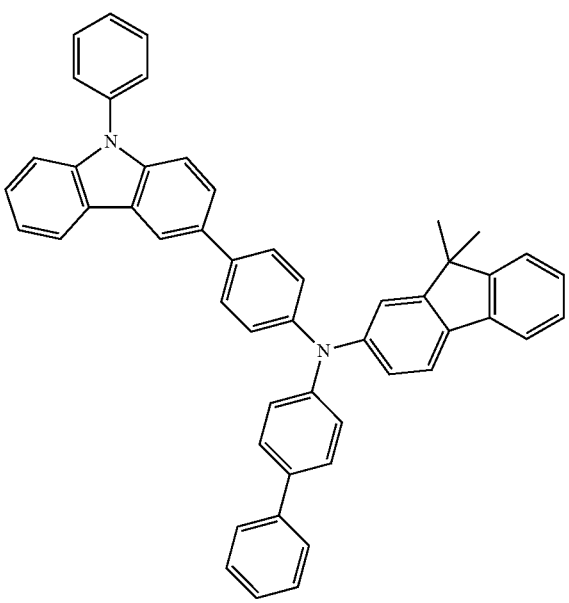

312
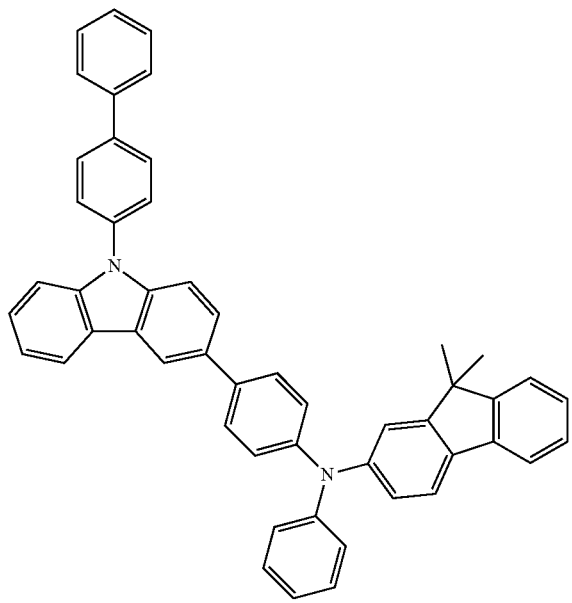
313
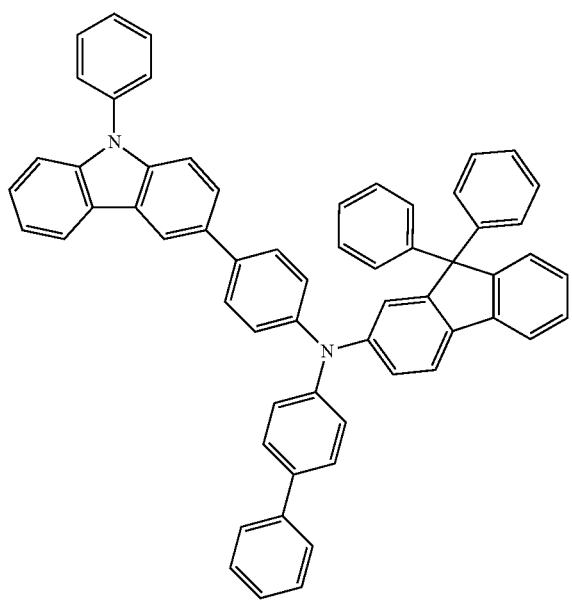
314
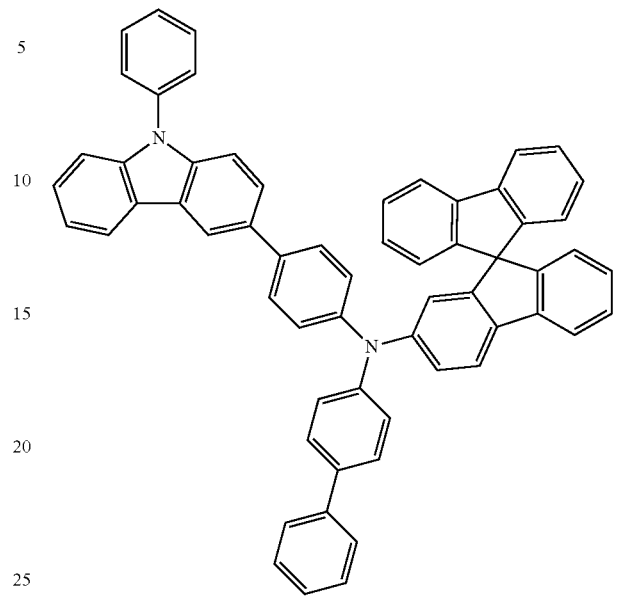
315
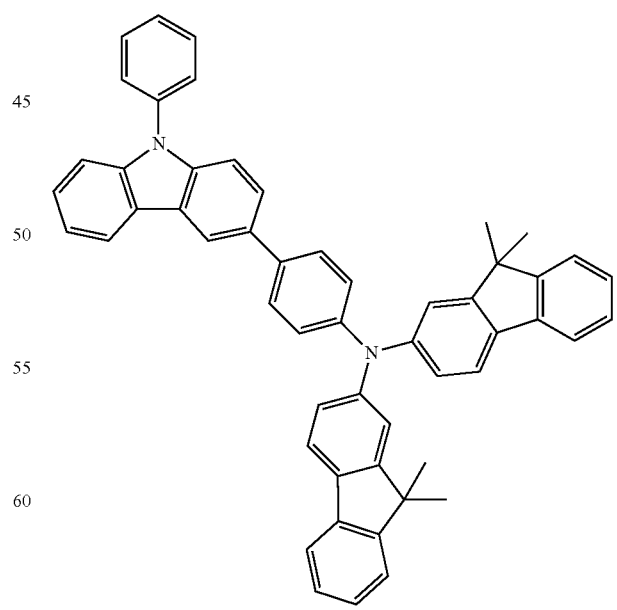

316
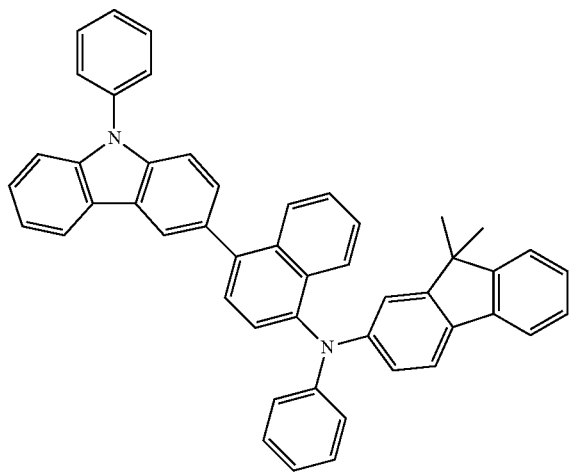
317
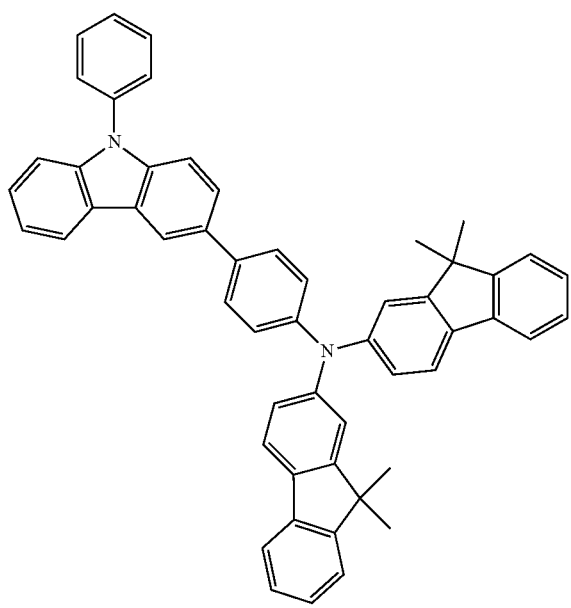
318
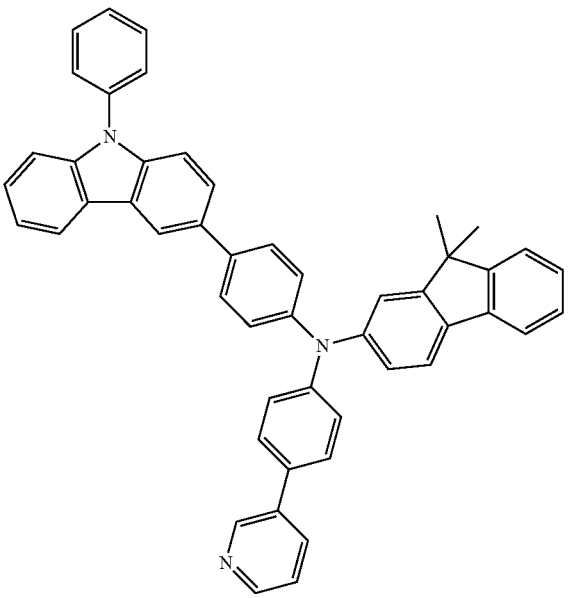
319
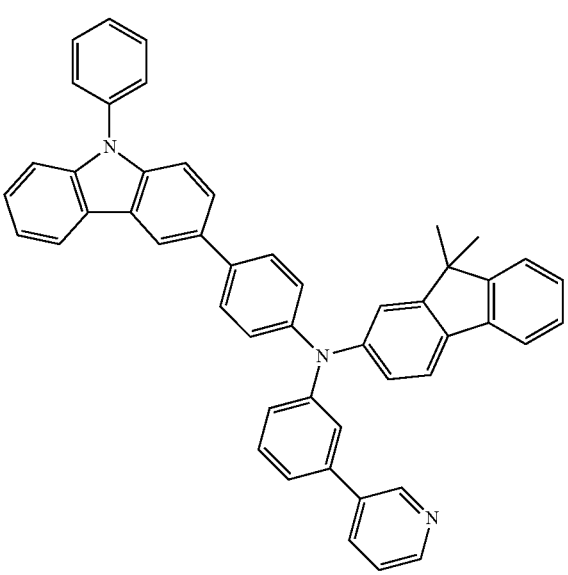

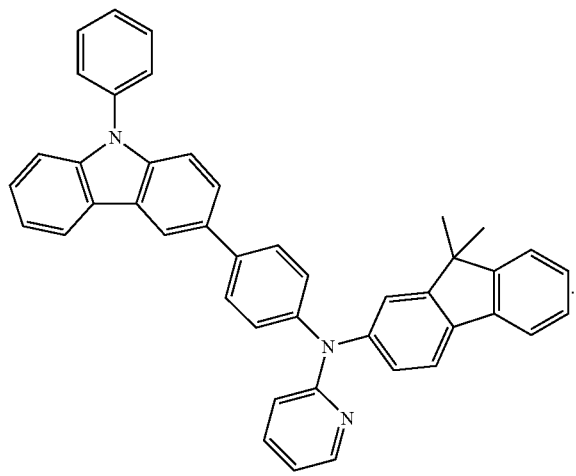

320

To improve conductivity, the hole transporting region may further include a charge-generating material in addition to the hole injection material and/or the hole transporting material.

The charge-generating material may be, for example, a p-dopant. The p-dopant may be a quinone derivative, a metal oxide, or a cyano-containing compound, but the p-dopant is not limited thereto. Non-limiting examples of the p-dopant include quinone derivatives such as tetra-cyanoquinodimethane (TCNQ) and 2,3,5,6-tetrafluoro-tetracyano-1,4-benzoquinodimethane (F4-TCNQ); metal oxides such as an tungsten oxide and a molybdenum oxide; and cyano-containing compounds such as Compound 200:

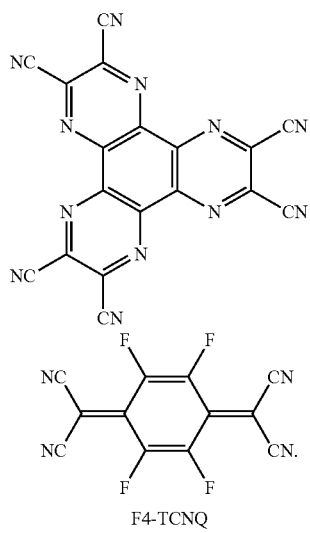

Compound 200

F4-TCNQ

When the hole transporting region further includes the charge-generating material, the charge-generating material may be homogeneously or non-homogeneously dispersed in the hole transporting region.

The hole transporting region may further include a buffer layer between the HTL and the EML.

The buffer layer may increase efficiency by compensating for an optical resonance distance according to the wavelength of light emitted from the EML. The buffer layer may include any suitable hole injection material and any suitable hole transporting material commonly used to form a HIL and a HTL, respectively. Also, the buffer layer may include the same material as one of the materials included in the HTL.

An EML may be formed on the hole transporting region by vacuum deposition, spin coating, casting, or LB deposition. When the EML is formed by vacuum deposition or spin coating, the deposition or coating conditions vary according to the compound used for forming the EML. The conditions for forming the EML may be similar to the conditions for forming the HIL.

The EML may include a host and a dopant.

Non-limiting examples of the host include $Alq_3$, 4,4'-N,N'-dicarbazole-biphenyl (CBP), 9,10-di(naphthalene-2-yl)anthracene (DNA), TCTA, 1,3,5-tris(N-phenylbenzimidazole-2-yl)benzene (TPBI), 3-tert-butyl-9,10-di(naphth-2-yl)anthracene (TBADN), E3, dmCBP, and Compounds 501 through 509:

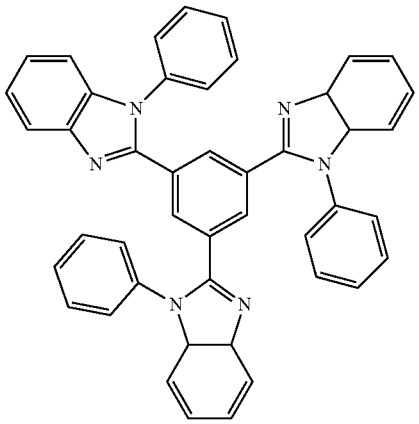

TPBI

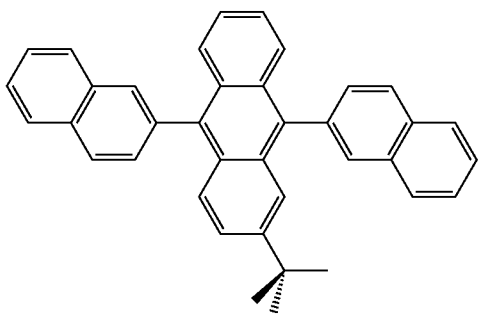

TBADN

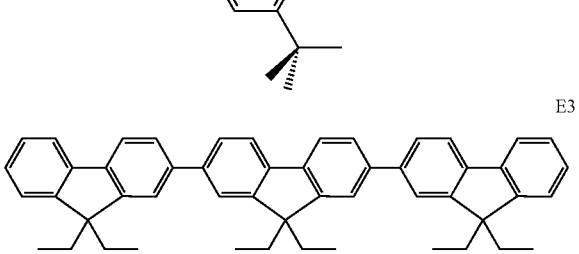

E3

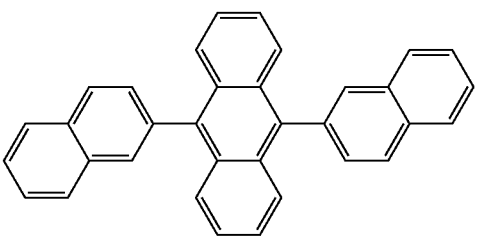

DNA

CBP
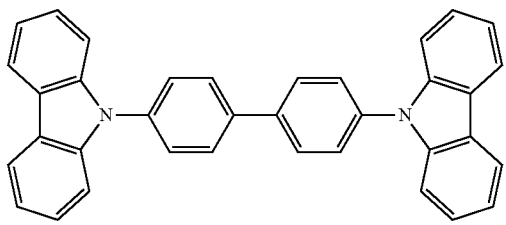
dmCBP
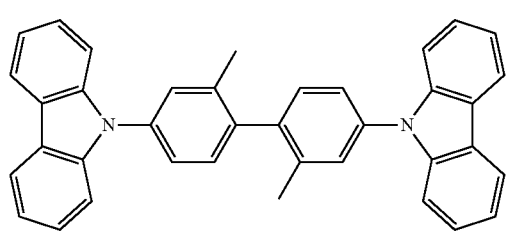
501
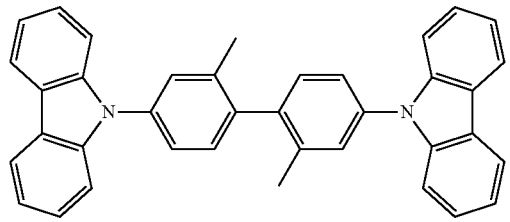
502
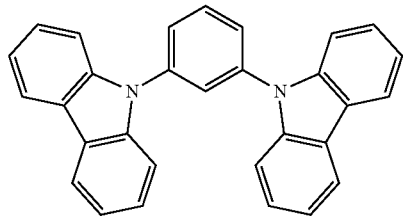
503
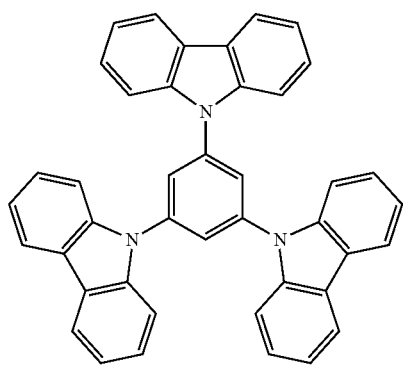
504
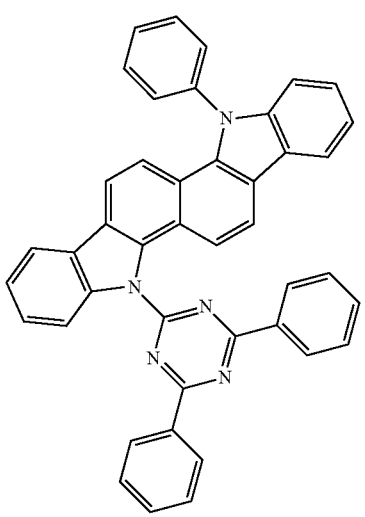
505
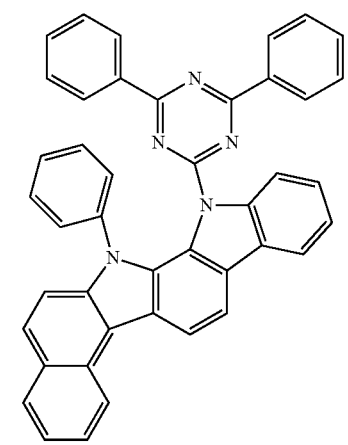
506
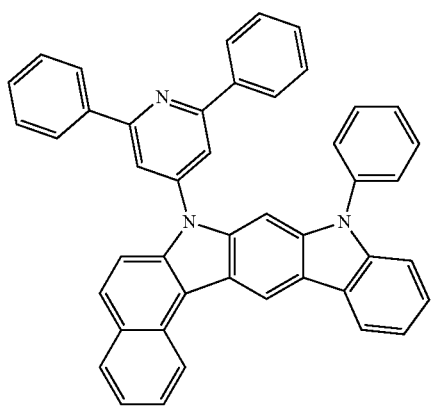

-continued

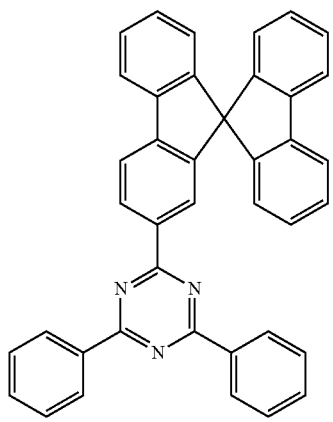
507

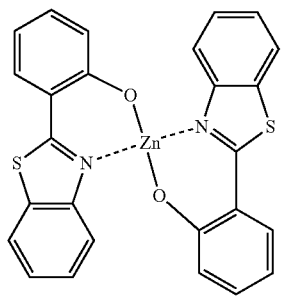
508

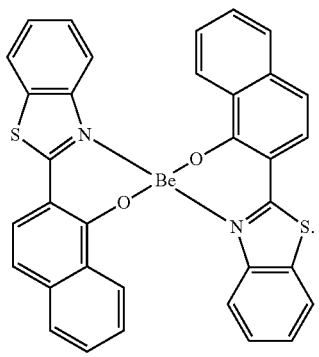
509

The host may include an anthracene-based compound represented by Formula 400:

Formula 400

Ar$_{114}$—(Ar$_{112}$)$_h$—(Ar$_{111}$)$_g$—Ar$_{113}$
(Ar$_{115}$)$_i$
(Ar$_{116}$)$_j$

In Formula 400, Ar$_{111}$ and Ar$_{112}$ may each independently be: a phenylene group, a naphthalene group, a fluorenyl group, a phenanthrenylene group, or a pyrenylene group; or a phenylene group, a naphthalene group, a phenanthrenylene group, a fluorenyl group, or a pyrenylene group, each substituted with at least one of a phenyl group, a naphthyl group, or an anthracenyl group.

In Formula 400, Ar$_{113}$ through Ar$_{116}$ may each independently be: a $C_1$-$C_{10}$ alkyl group; a phenyl group, a fluorenyl group, a naphthyl group, a phenanthrenyl group, or a pyrenyl group; or a phenyl group, a naphthyl group, a phenanthrenyl group, a fluorenyl group, or a pyrenyl group, each substituted with at least one of a phenyl group, a naphthyl group, or an anthracenyl group.

In Formula 400, g, h, i, and j may each independently be an integer of 0 to 4, for example, 0, 1, or 2. When g, h, i, and/or j is an integer of 2 or more, the two or more Ar$_{111}$s, Ar$_{112}$s, Ar$_{115}$s and/or Ar$_{115}$s are the same or different.

In Formula 400, Ar$_{113}$ through Ar$_{116}$ may each independently be: a $C_1$-$C_{10}$ alkyl group, each substituted with at least one of a phenyl group, a naphthyl group, or an anthracenyl group; or a phenyl group, a naphthyl group, an anthracenyl group, a pyrenyl group, a phenanthrenyl group, or a fluorenyl group; or a phenyl group, a naphthyl group, an anthracenyl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{50}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, or a fluorenyl group; or a

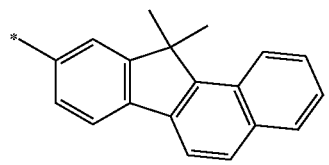 [SMILES: Cc1ccc2c(c1)C(C)(C)c1c-2ccc2ccccc12]

moiety. However, Ar$_{113}$ through Ar$_{116}$ are not limited thereto. * is a binding site to a corresponding atom of Formula 400 or to a corresponding Ar$_{111}$ or Ar$_{112}$.

Non-limiting examples of the anthracene-based compound of Formula 400 include the following compounds:

-continued
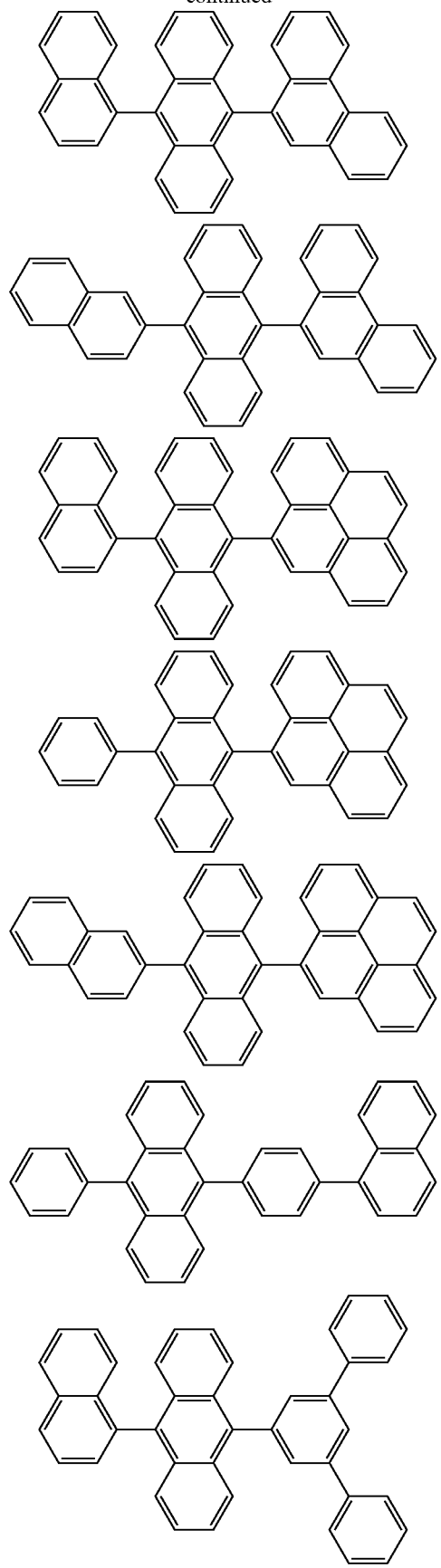
-continued
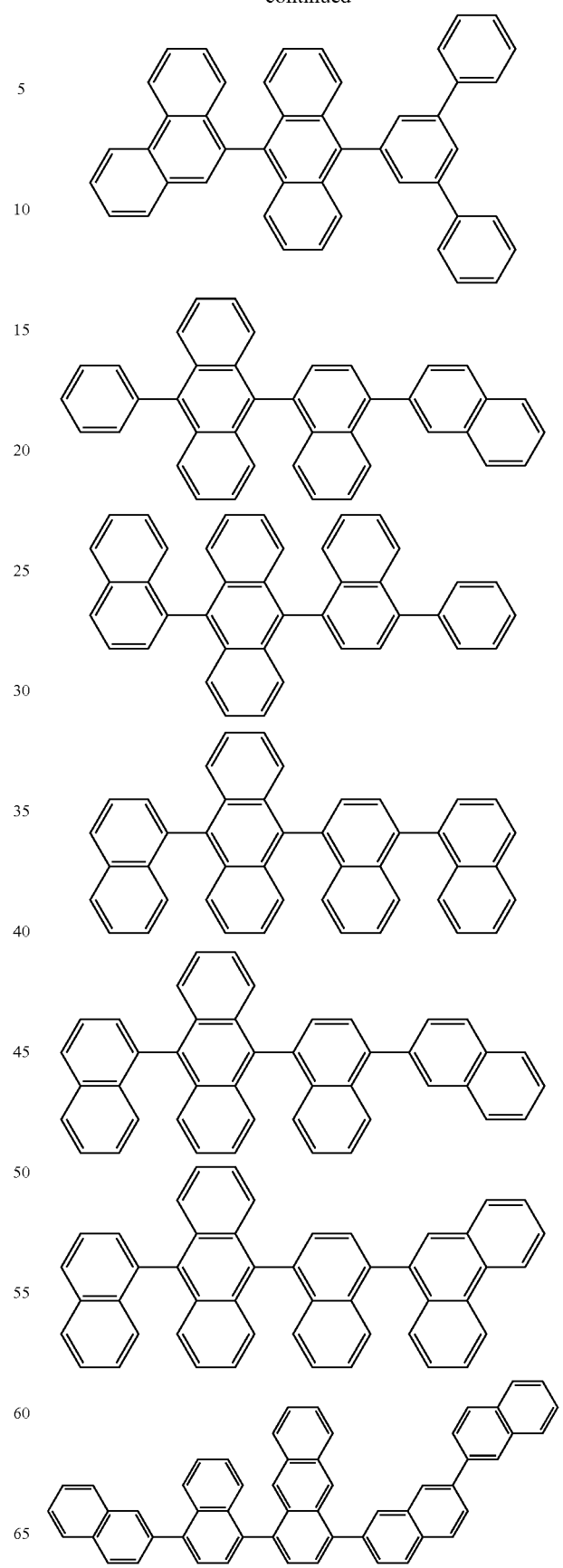

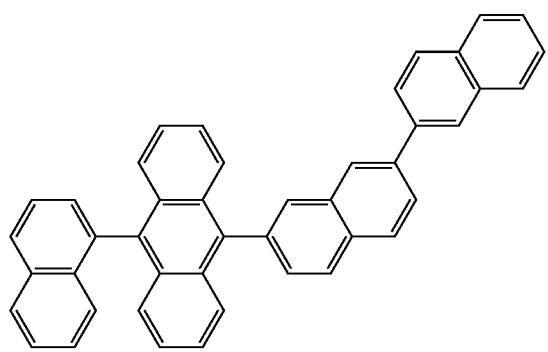
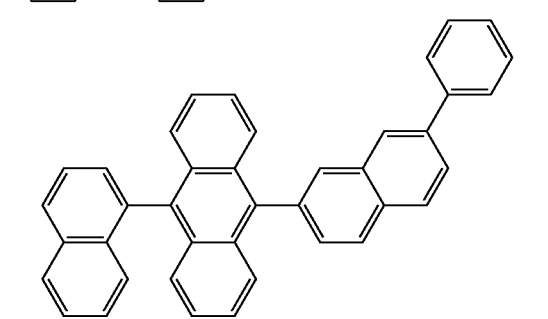
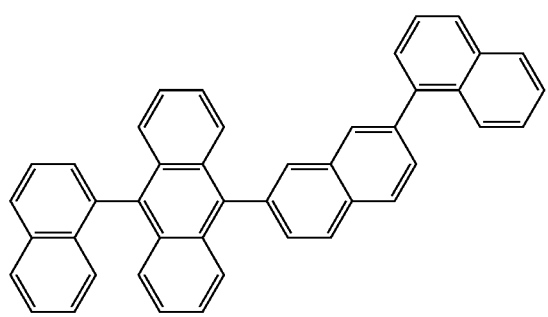
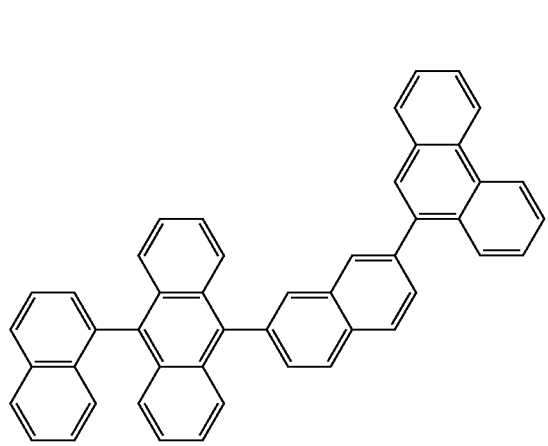
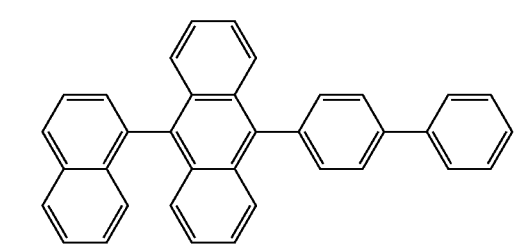
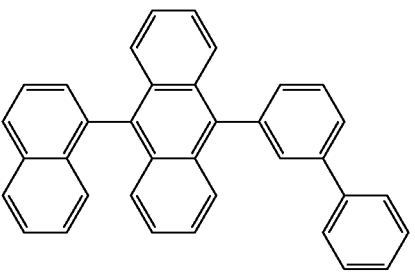
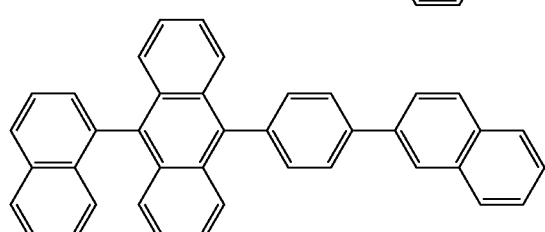
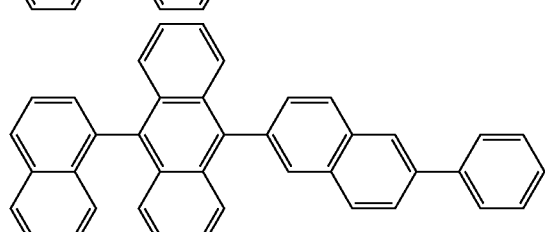
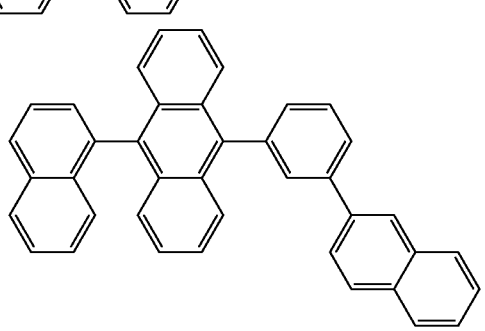
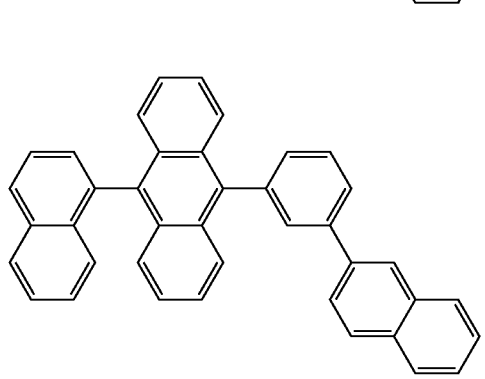
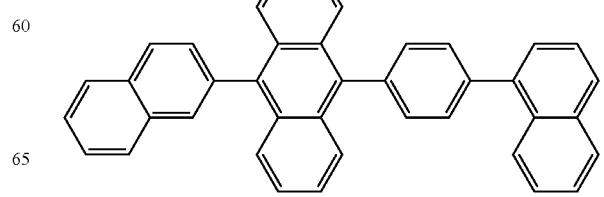

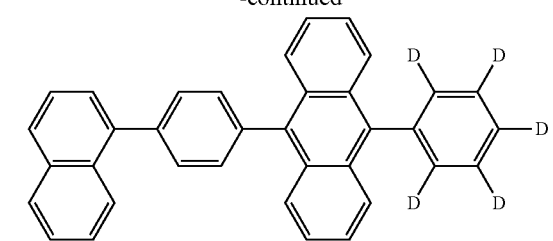
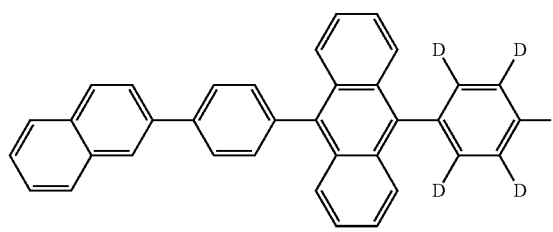
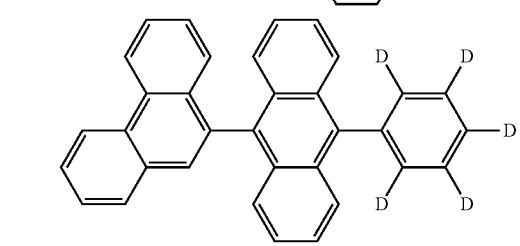
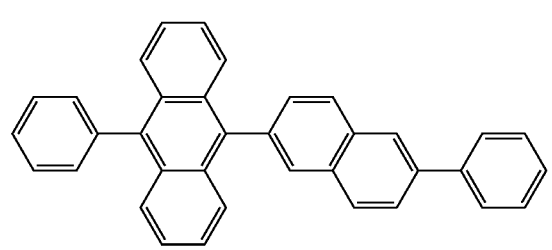
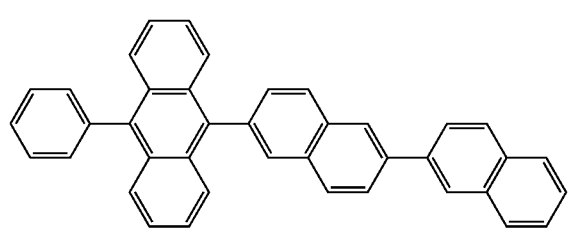
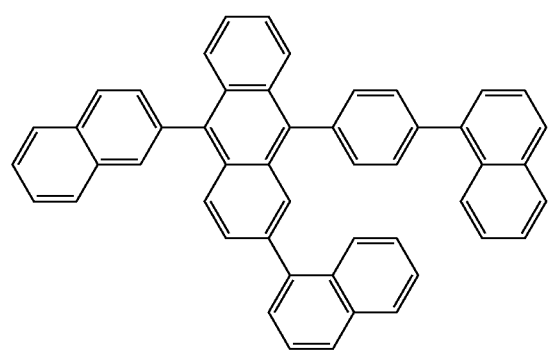
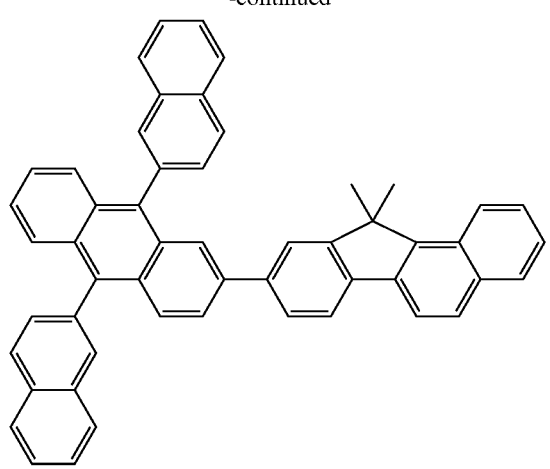
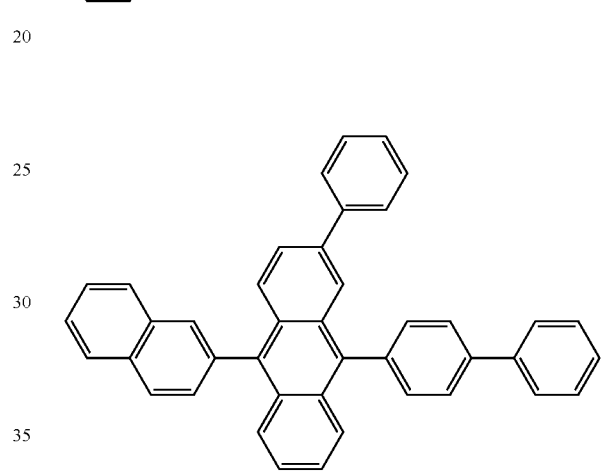
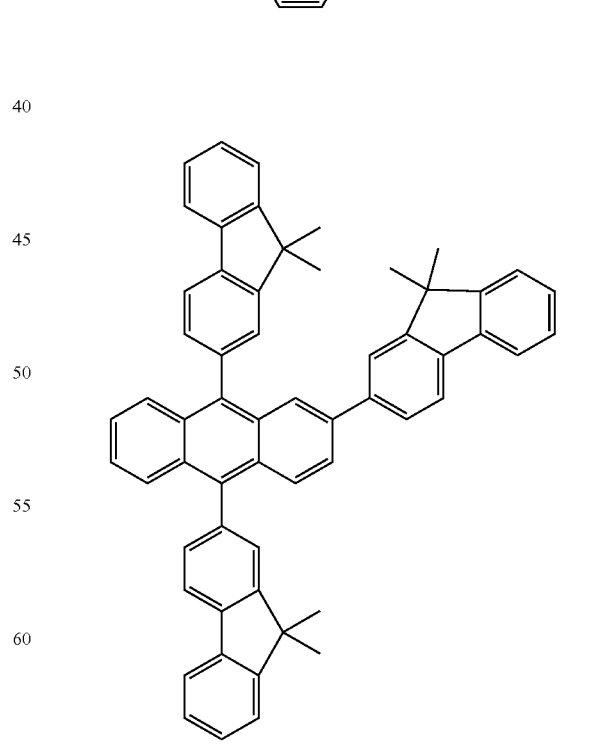

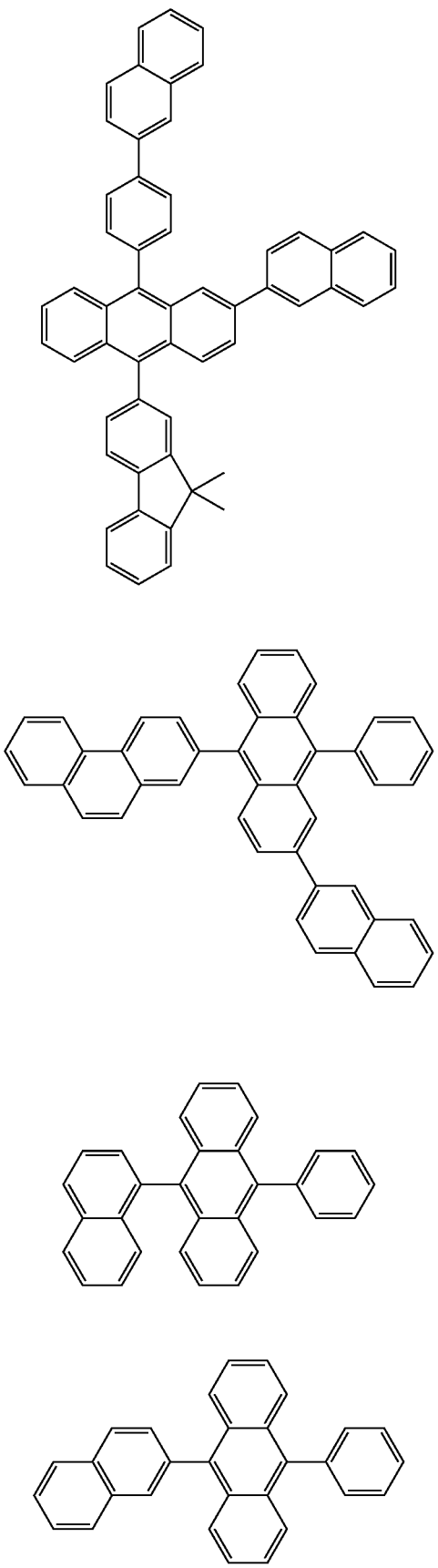
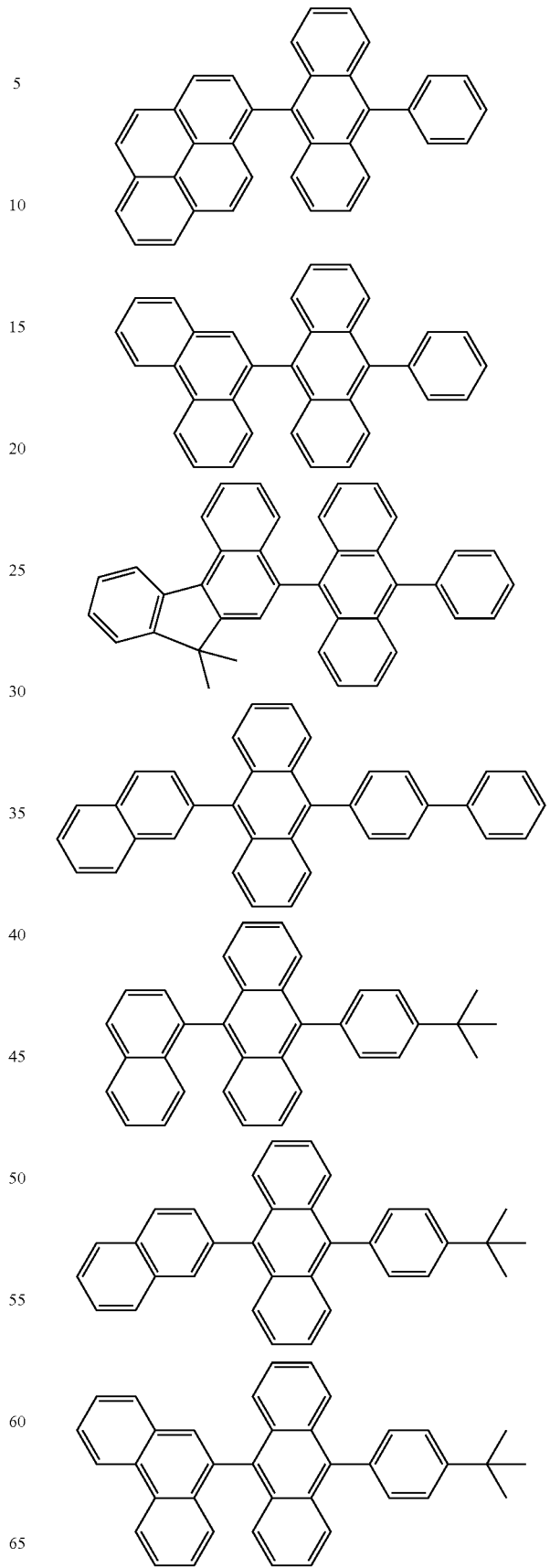

-continued
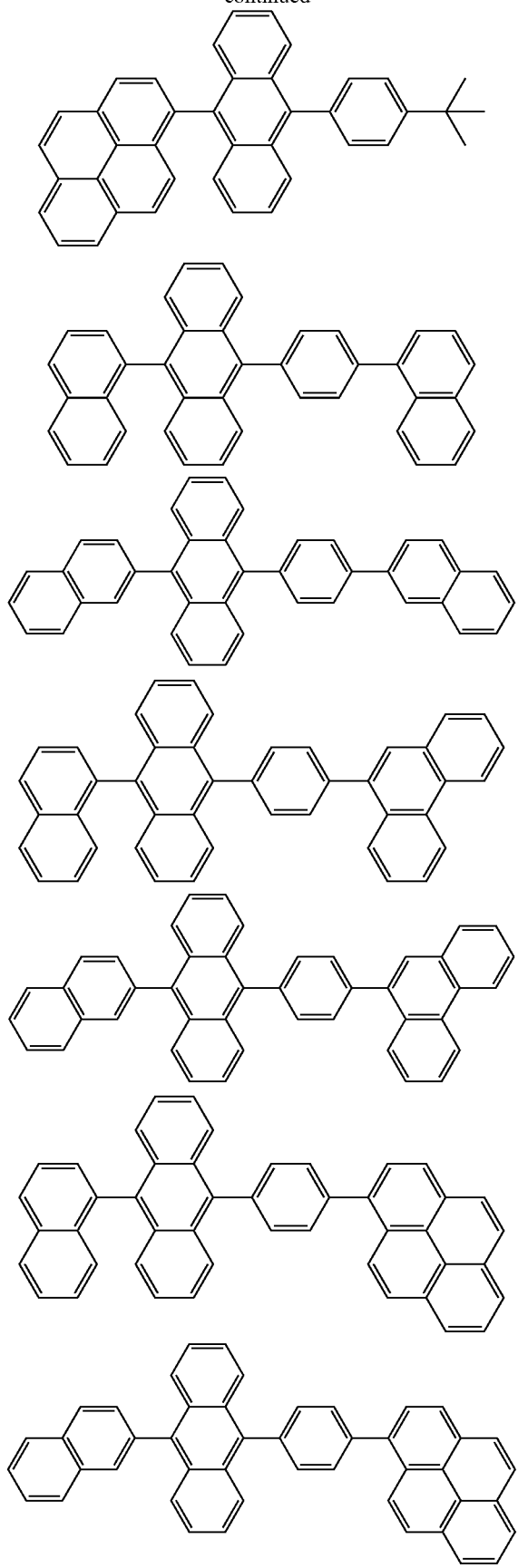
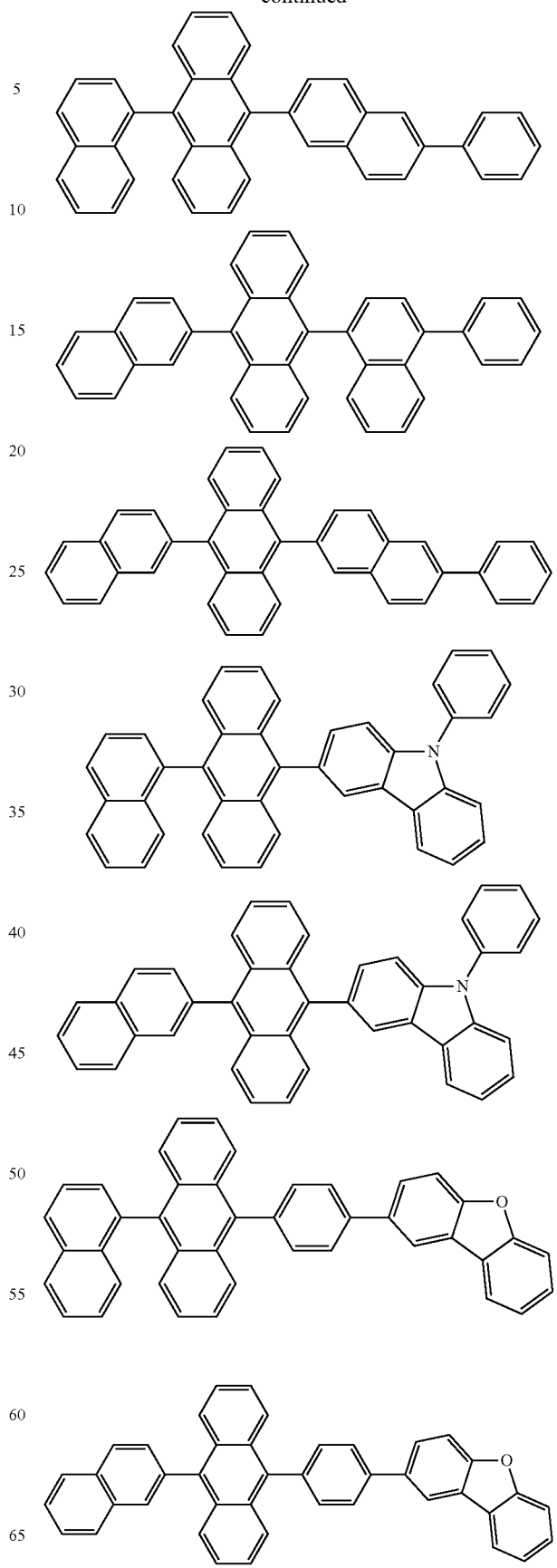

-continued
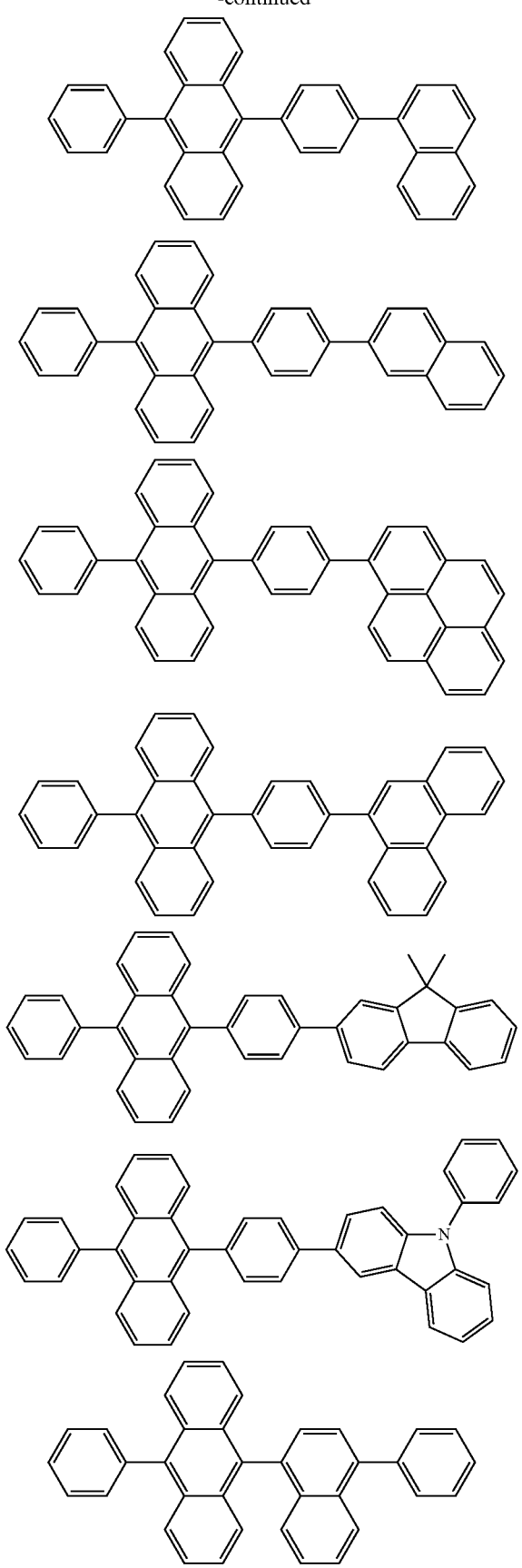
-continued
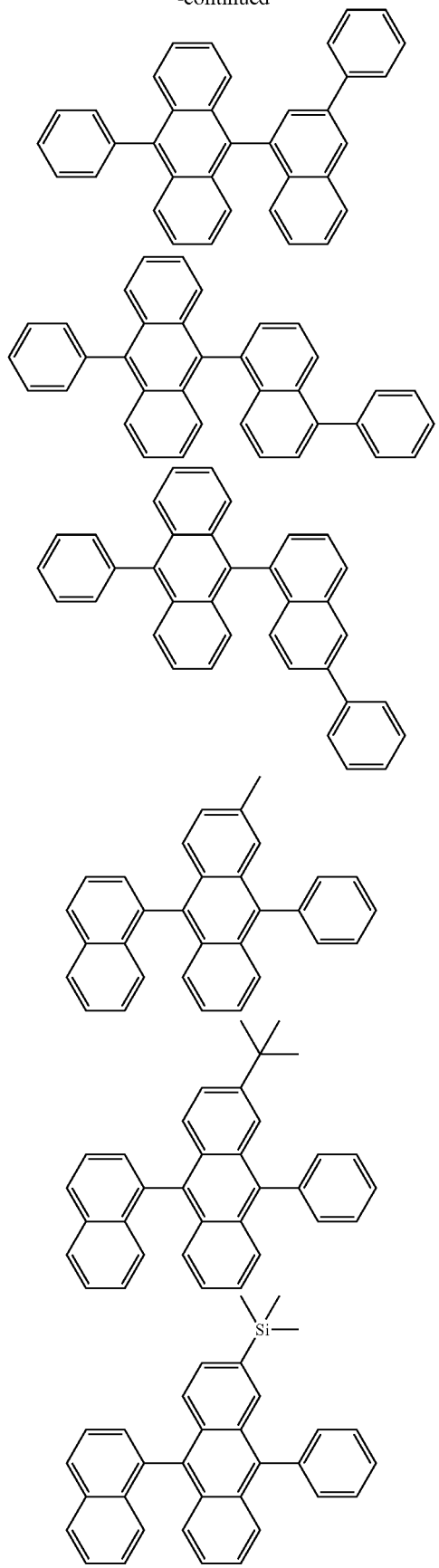

-continued
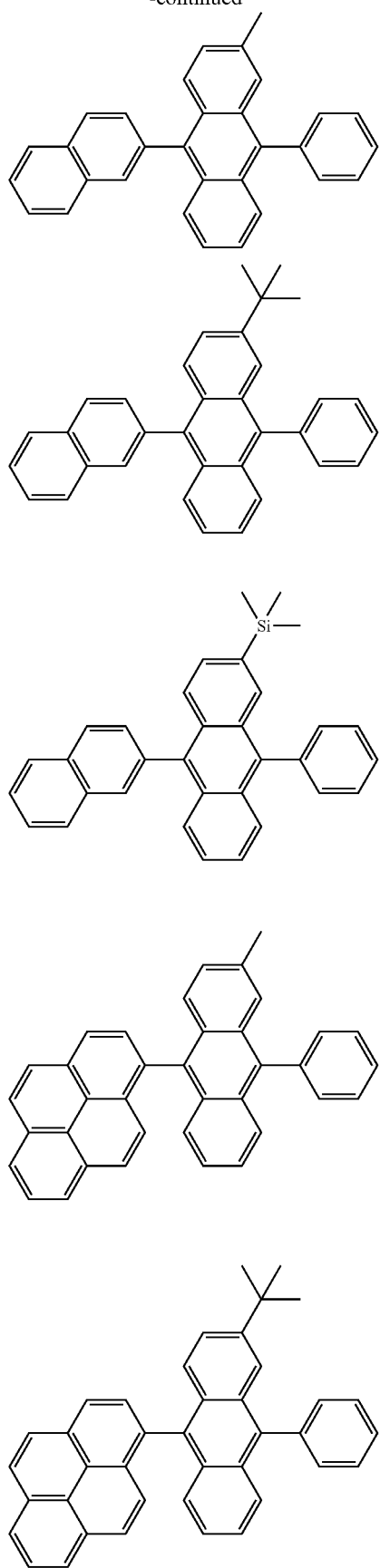
-continued
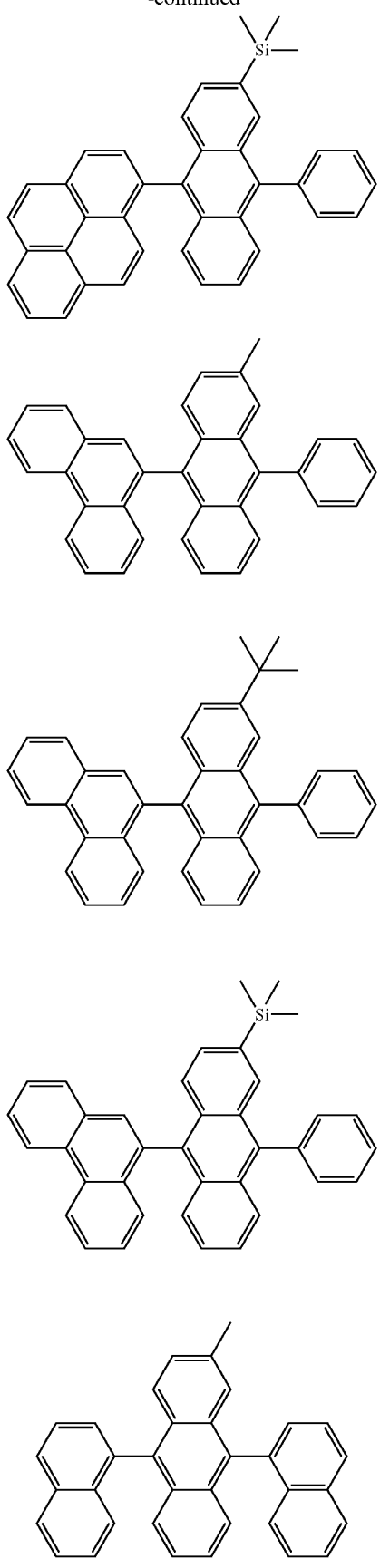

-continued
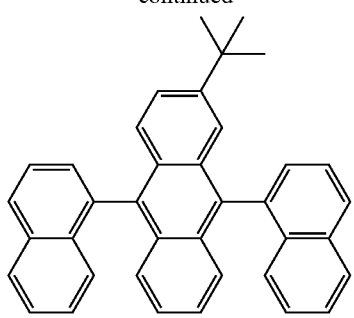
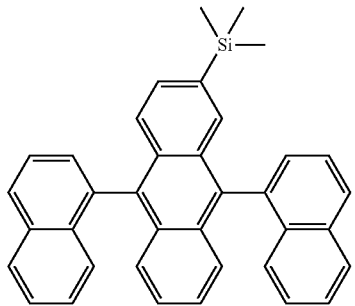
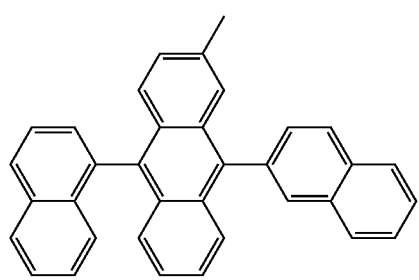
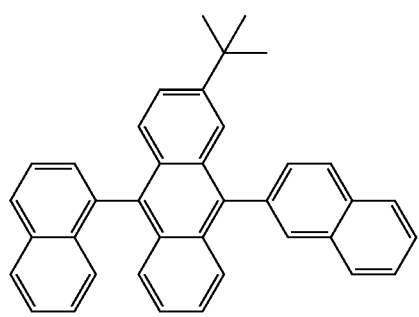
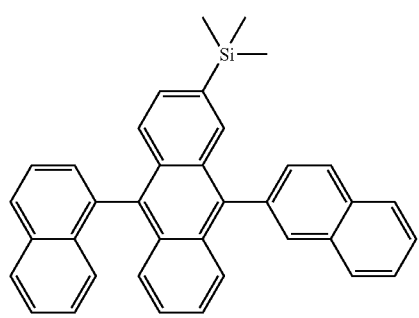
-continued
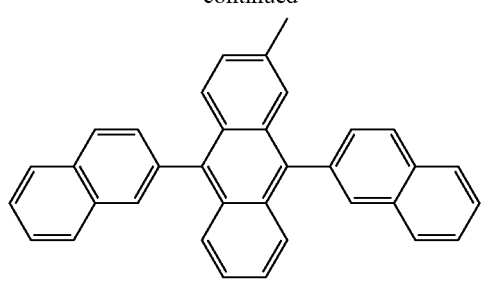
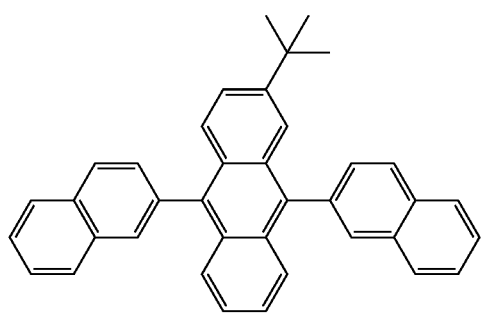
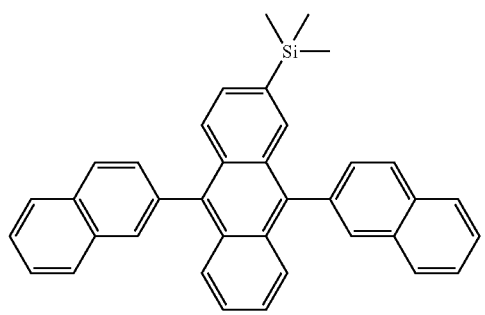
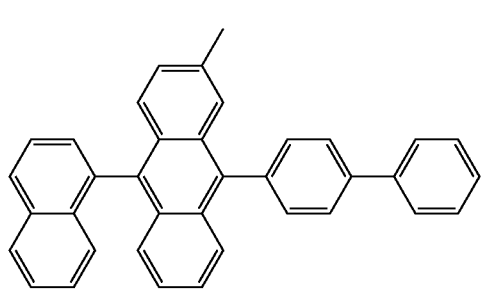
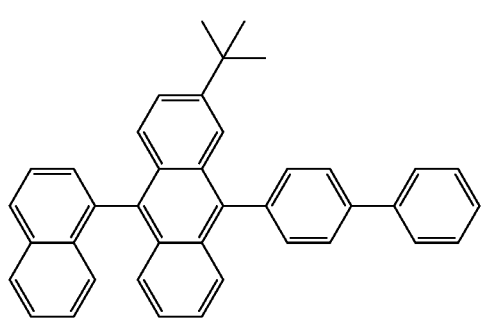

-continued
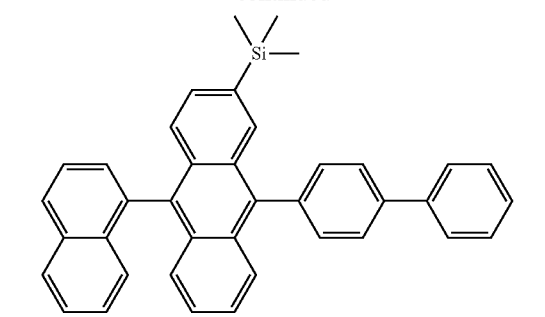
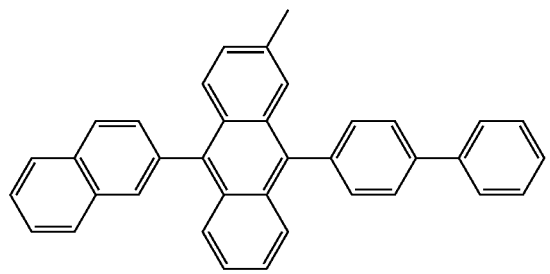
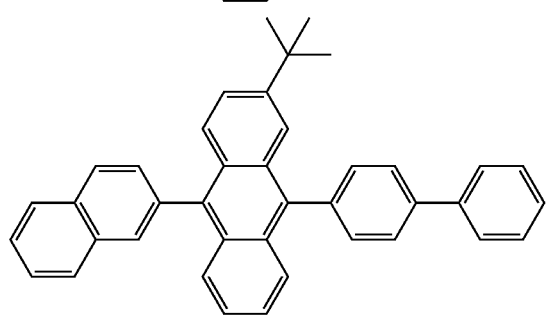
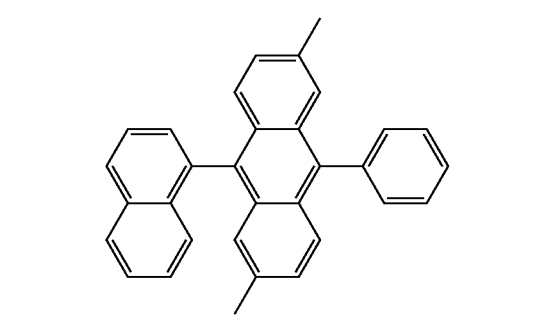
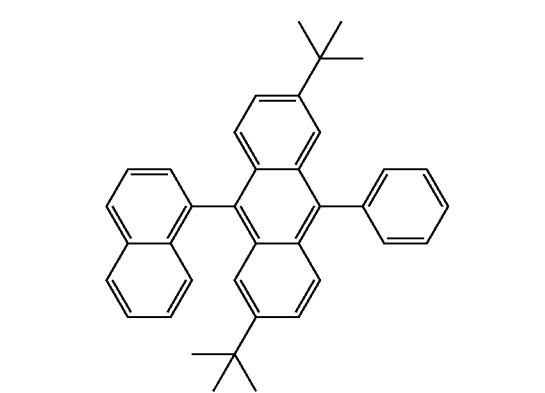
-continued
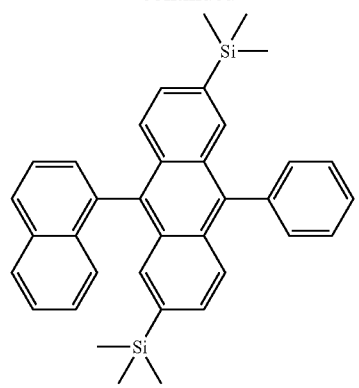
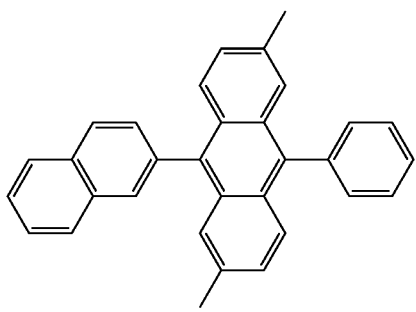
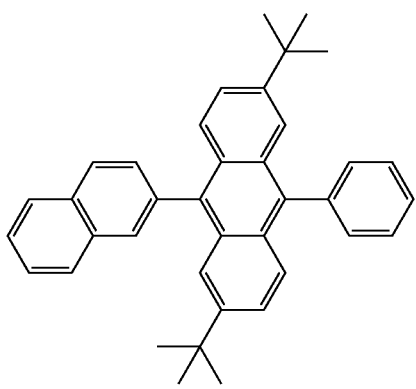
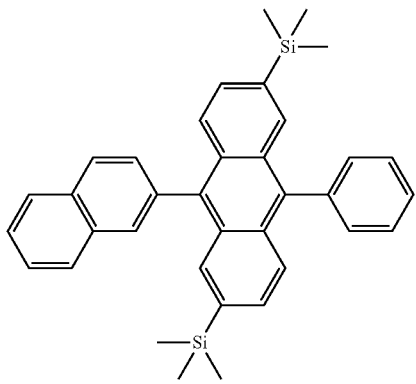

69
-continued
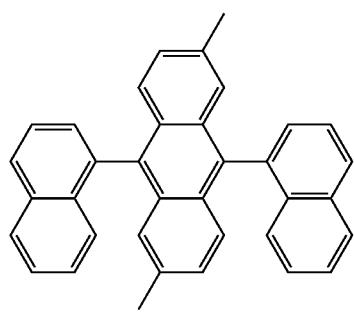
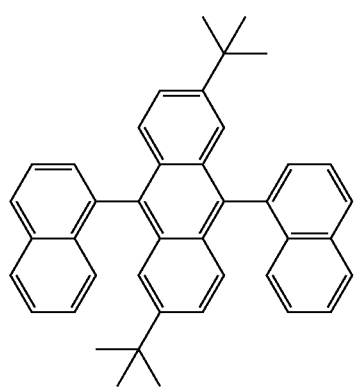
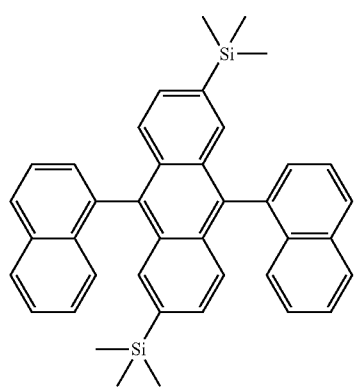
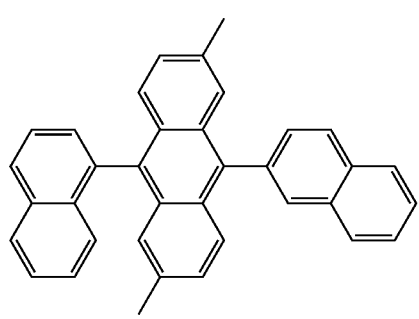
70
-continued
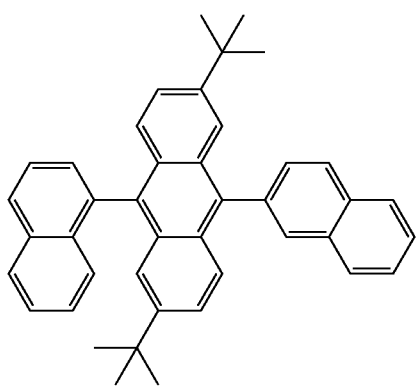
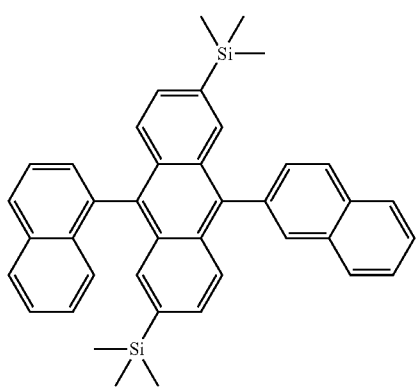
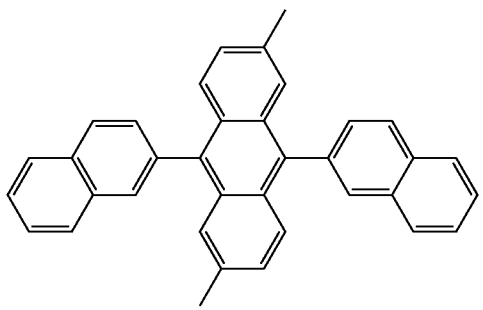
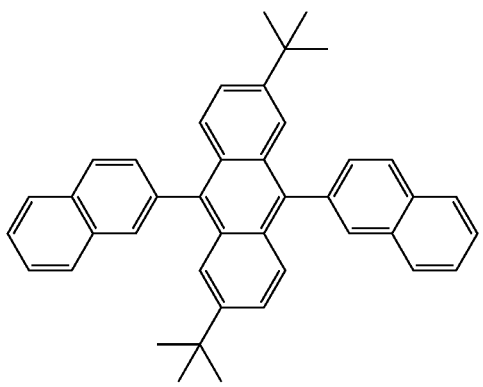

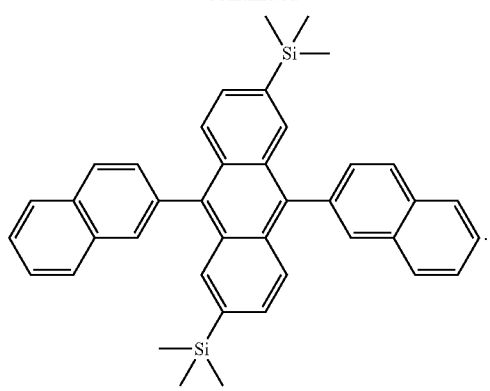 [SMILES: C[Si](C)(C)c1ccc2c(-c3ccc4ccccc4c3)c3cc([Si](C)(C)C)ccc3c(-c3ccc4ccccc4c3)c2c1]

The anthracene-based compound may be a host, and may be represented by Formula 401:

Formula 401

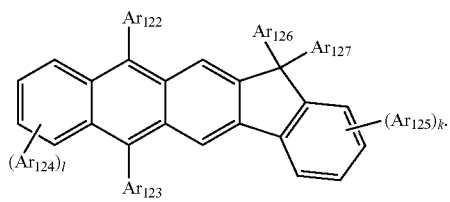

In Formula 401, $Ar_{122}$ through $Ar_{125}$ are the same as those described in connection with Formula 400.

In Formula 401, $Ar_{126}$ and $Ar_{127}$ may each independently be a $C_1$-$C_{10}$ alkyl group (e.g., a methyl group, an ethyl group, or a propyl group).

In Formula 401, k and l may each independently be an integer of 0 to 4. For example, k and l may each independently be 0, 1, or 2. When k and/or l is an integer of 2 or more, the two or more Ar125$_1$s and/or $Ar_{124}$s may be the same or different.

Non-limiting examples of the anthracene-based compound of Formula 401 include the following compounds:

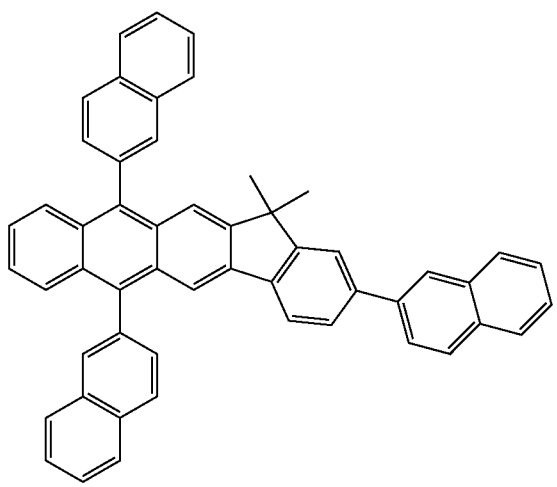

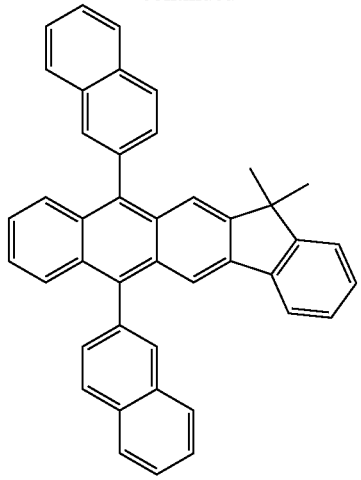

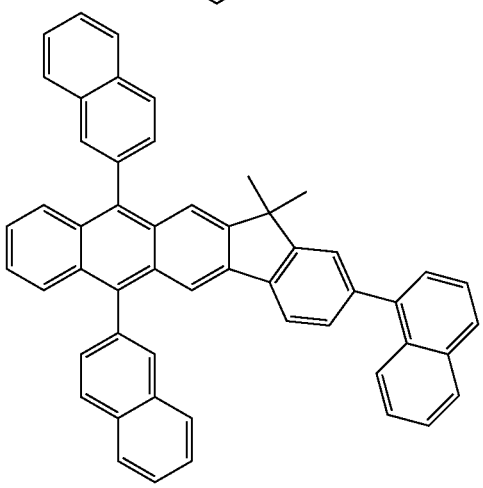

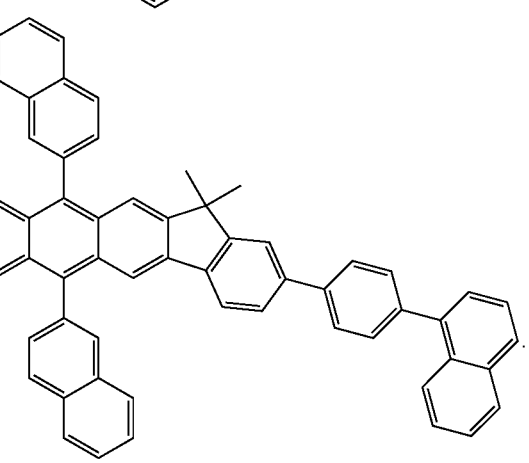

When the OLED is a full-color OLED, the EML may be patterned to separately include a red EML, a green EML, and a blue EML. Alternatively the EML may have a structure in which a red EML, a green EML, and/or a blue EML are stacked so as to emit white light.

The dopant in the EML may be a fluorescent dopant that emits light by a fluorescence mechanism and/or a phosphorescent dopant that emits light by a phosphorescence mechanism. When the EML includes a fluorescent dopant, the fluorescent dopant may include the amine-based compound represented by Formula 1.

The OLED may further include any suitable commonly used dopant, in addition to the amine-based compound represented by Formula 1 (e.g., as a dopant for full-color emission). For example, a blue emission layer of the OLED may include the amine-based compound represented by Formula 1 as a dopant, while a green emission layer and a red emission layer may include other suitable commonly used phosphorescent dopants.

The phosphorescent dopants may include an organic metal complex including a transition metal (e.g., iridium (Ir), platinum (Pt), osmium (Os), or rhodium (Rh)).

Non-limiting examples of the red dopant include the following compounds:

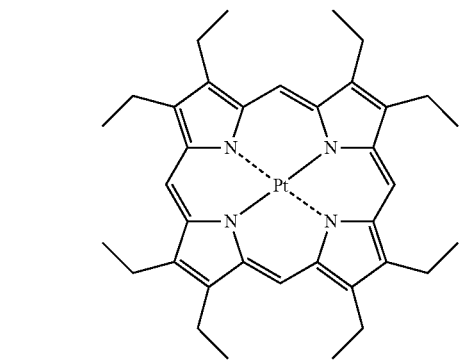

PtOEP

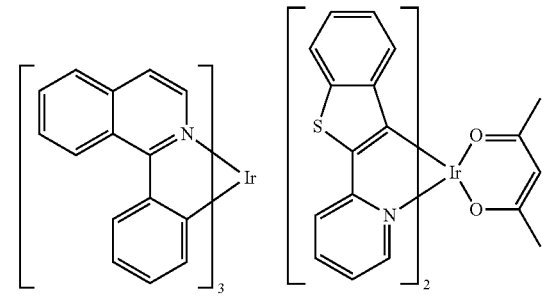

Ir(piq)₃       Btp₂Ir(acac)

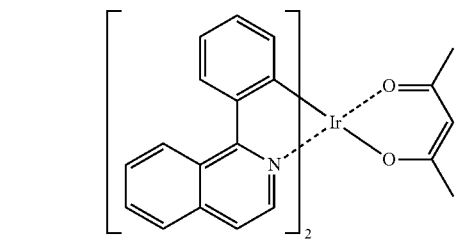

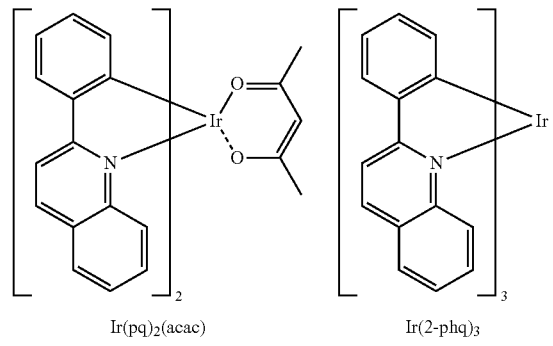

Ir(pq)₂(acac)     Ir(2-phq)₃

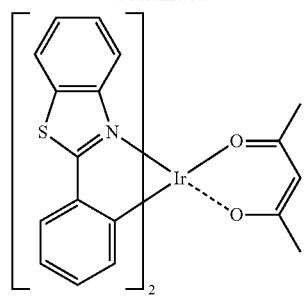

Ir(BT)₂(acac)

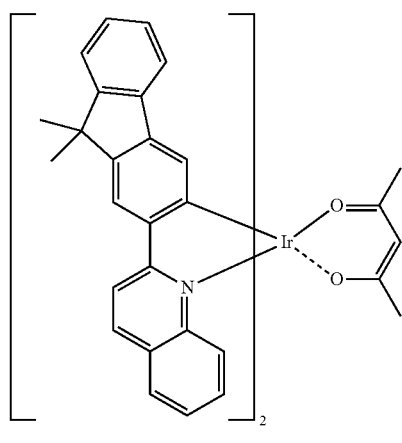

Ir(flq)₂(acac)

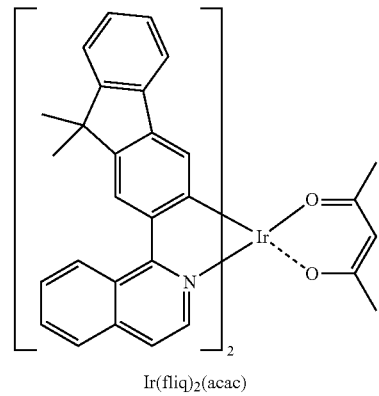

Ir(fliq)₂(acac)

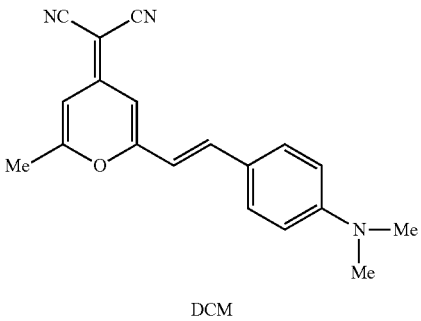

DCM

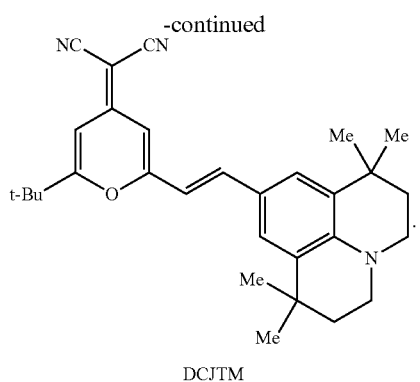
DCJTM
Non-limiting examples of the green dopant include the following compounds:
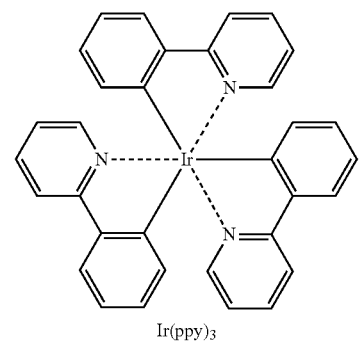
Ir(ppy)₃
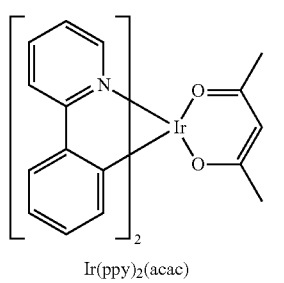   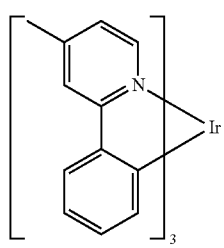
Ir(ppy)₂(acac)         Ir(mpyp)₃
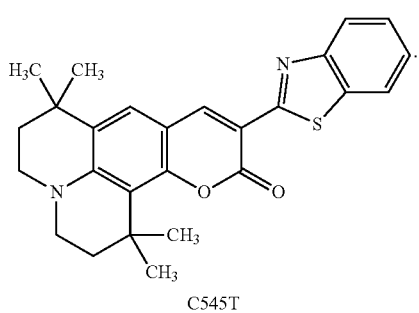
C545T
Non-limiting examples of dopants which may be included in the emission layer include organic metal complexes, such as Compounds D1 through D50:
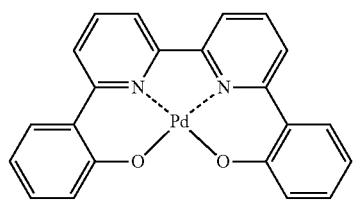
D1
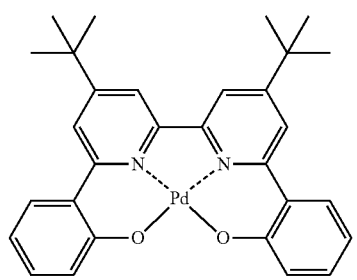
D2
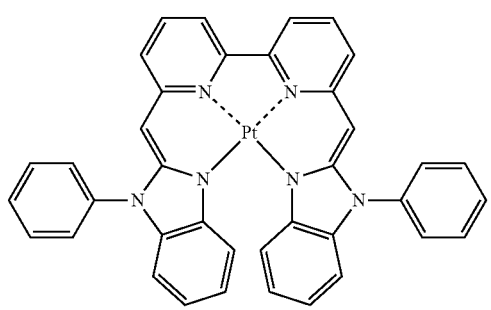
D3
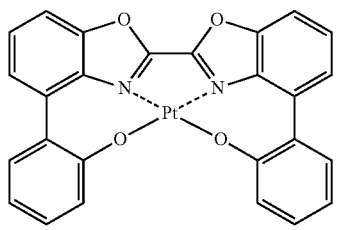
D4
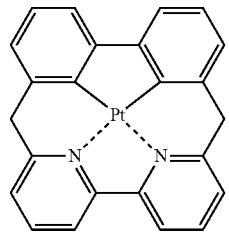
D5
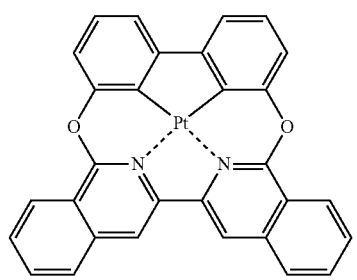
D6

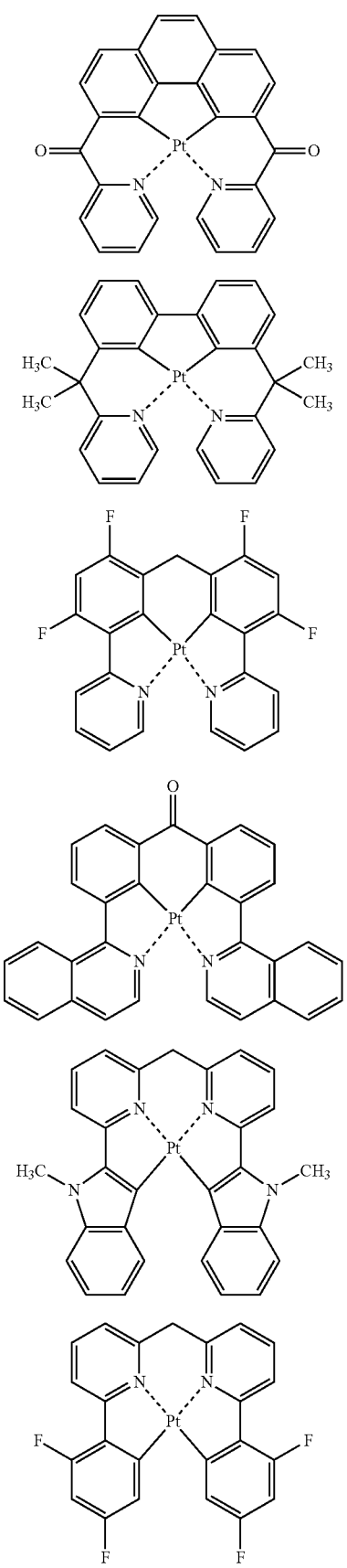
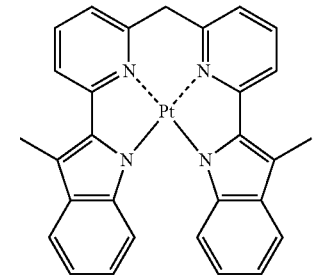
D13
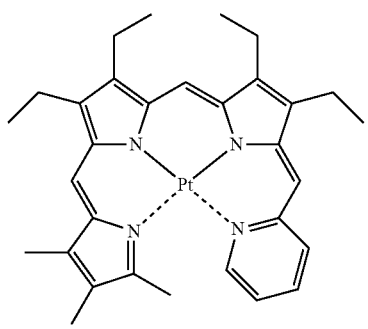
D14
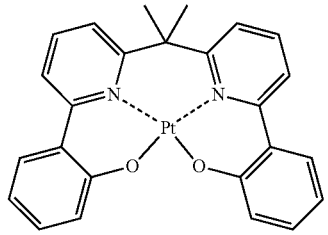
D15
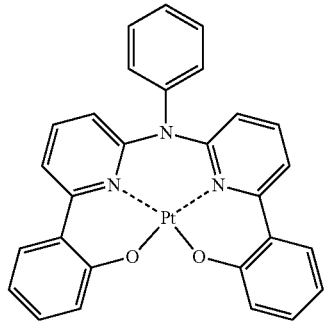
D16
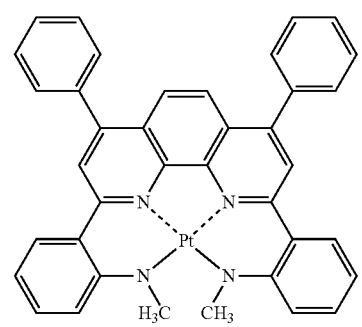
D17

-continued
D18
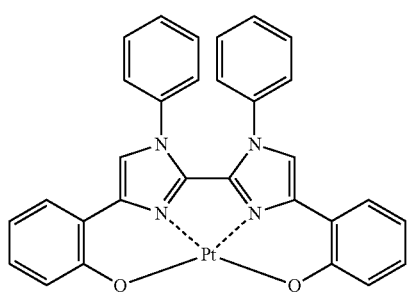
D19
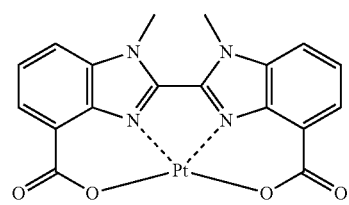
D20
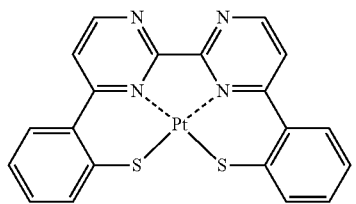
D21
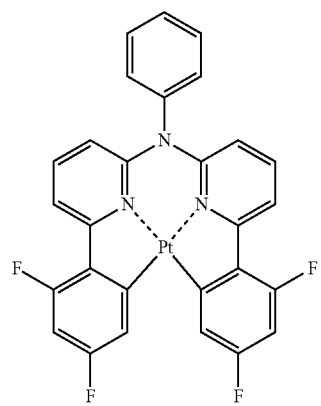
D22
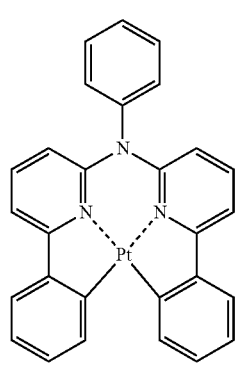
-continued
D23
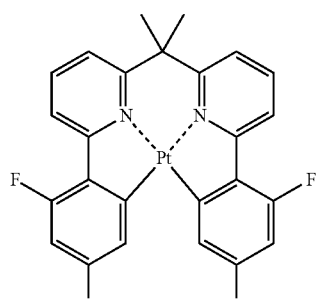
D24
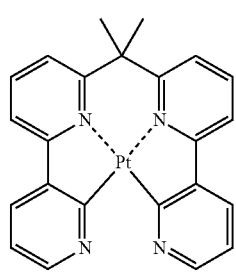
D25
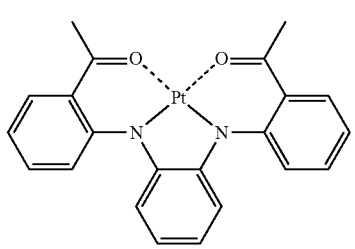
D26
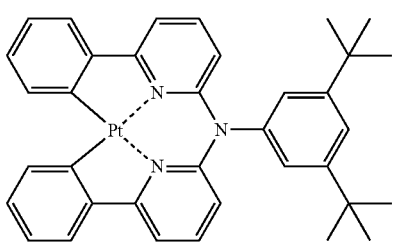
D27
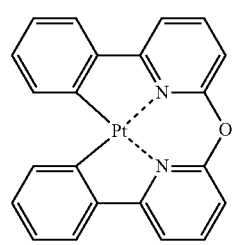
D28
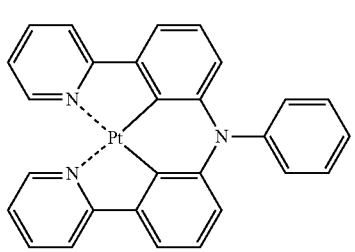

-continued
D29
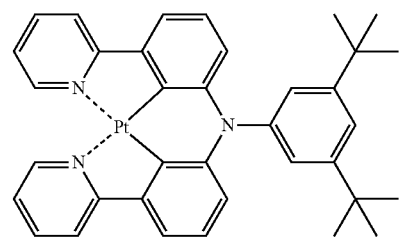
D30
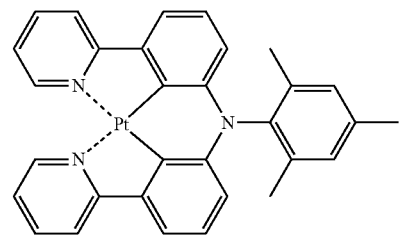
D31
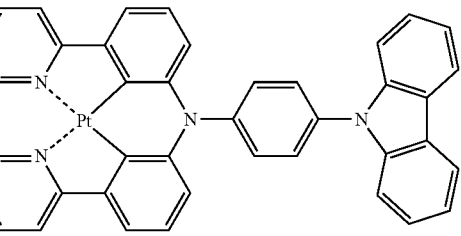
D32
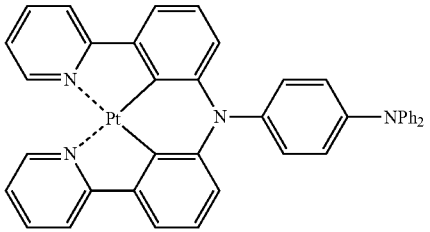
D33
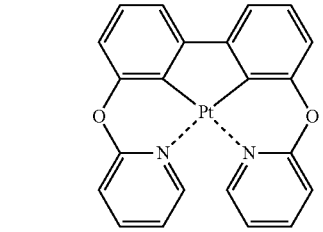
D34
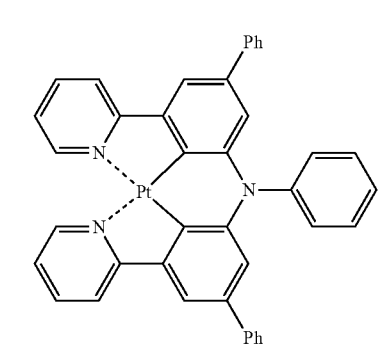
-continued
D35
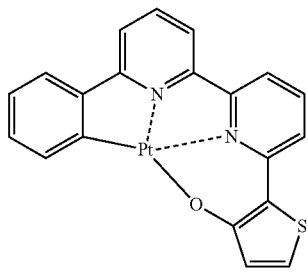
D36
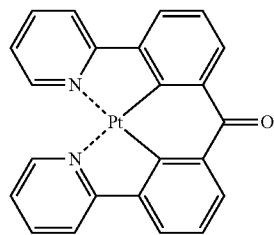
D37
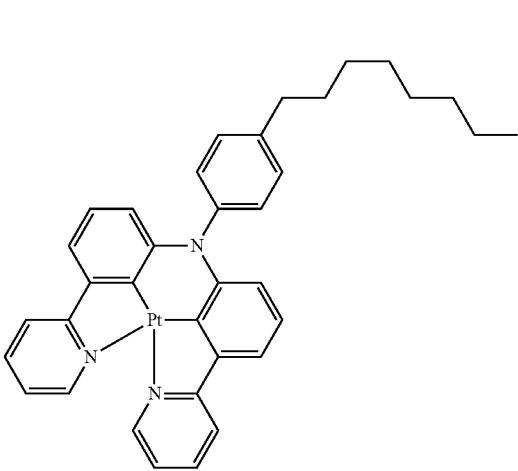
D38
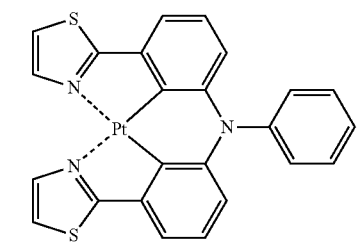
D39
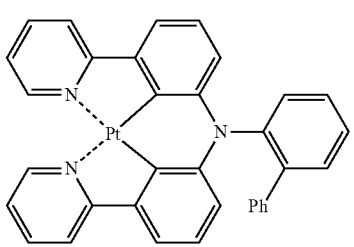

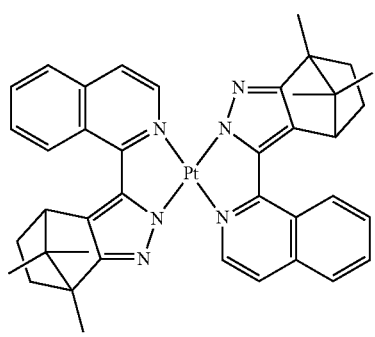 D40
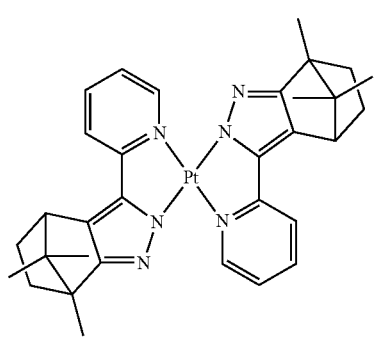 D41
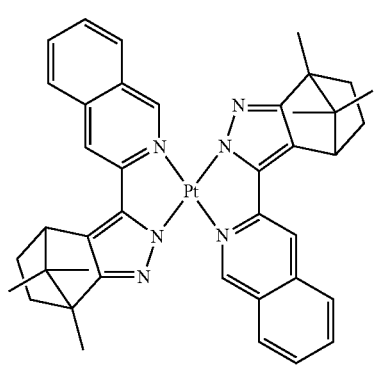 D42
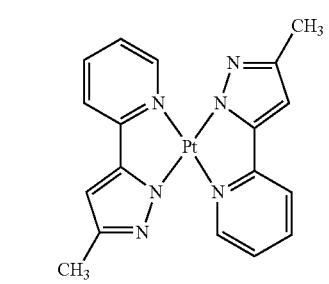 D43
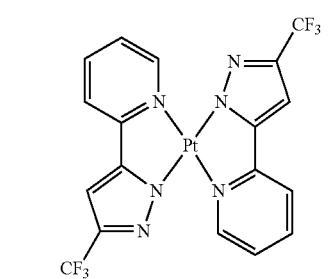 D44
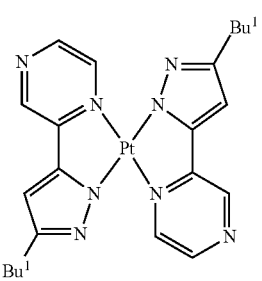 D45
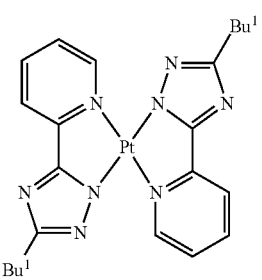 D46
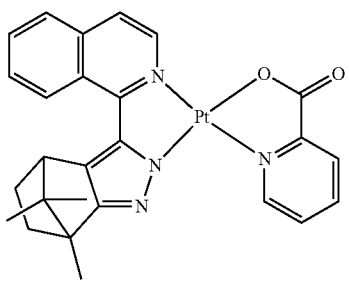 D47
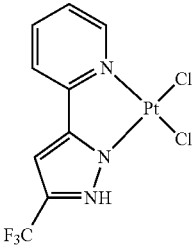 D48
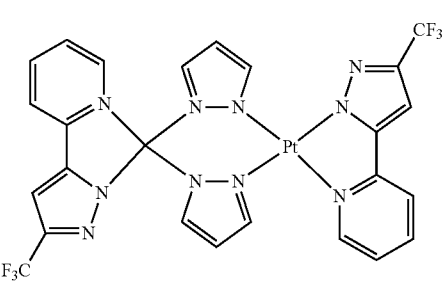 D49

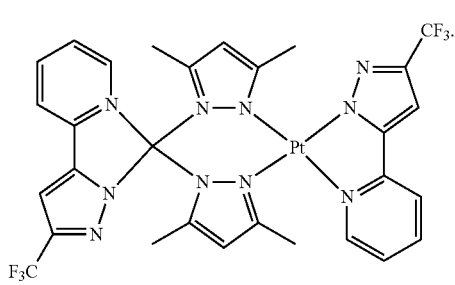

D50

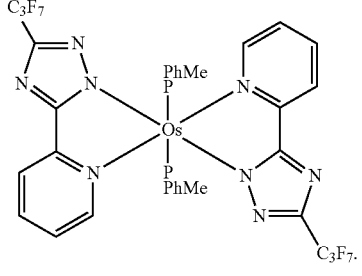

Os(hptz)₂(PPhMe₂)₂

Additional non-limiting examples of the dopant which may be included in the EML include the following organic metal complexes:

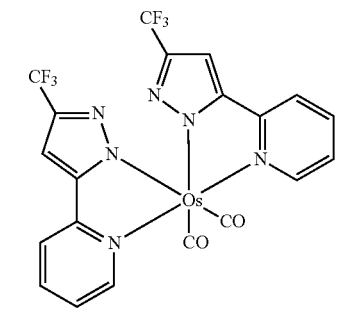

Os(fppz)₂(CO)₂

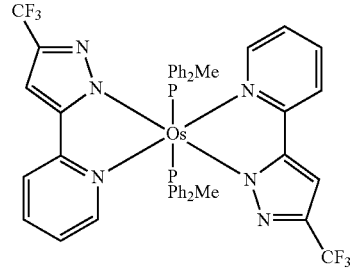

Os(fppz)₂(PPh₂Me)₂

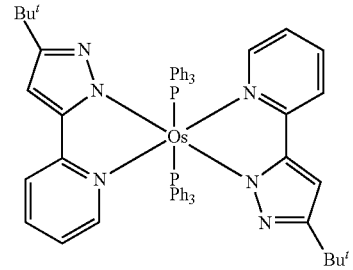

Os(bppz)₂(PPh₃)₂

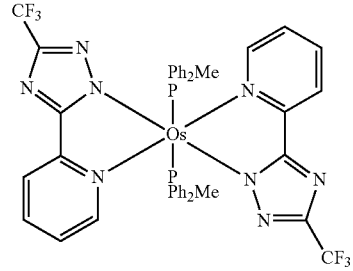

Os(fptz)₂(PPh₂Me)₂

When the EML includes a host and a dopant, the amount of the dopant in the EML may be about 0.01 to about 15 parts by weight based on 100 parts by weight of the host, but the amount of the dopant is not limited thereto.

In some embodiments, the thickness of the EML may be about 100 Å to about 1,000 Å, for example about 200 Å to about 600 Å. In these embodiments, suitable luminescent properties may be obtained without a substantial increase in driving voltage.

An ETL may be formed using various methods such as vacuum deposition, spin coating, or casting. When the ETL is formed by vacuum deposition or spin coating, the deposition or coating conditions may vary according to the compound used to form the ETL. The conditions may be similar to the conditions for forming the HIL.

The material for forming the ETL may be any electron transporting material capable of stably transporting electrons injected from a cathode. Non-limiting examples of the electron transporting material include a quinoline derivative such as tris(8-quinolinolate)aluminum (Alq₃), TAZ, BAlq, beryllium bis(benzoquinolin-10-olate (Bebq₂), ADN, or Compound 201, or Compound 202:

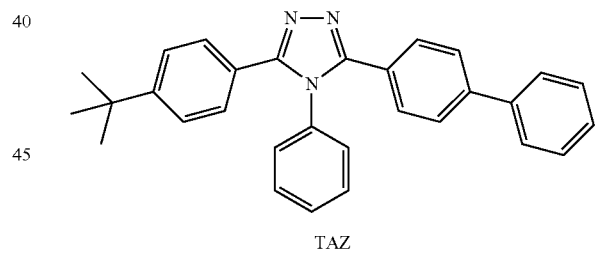

TAZ

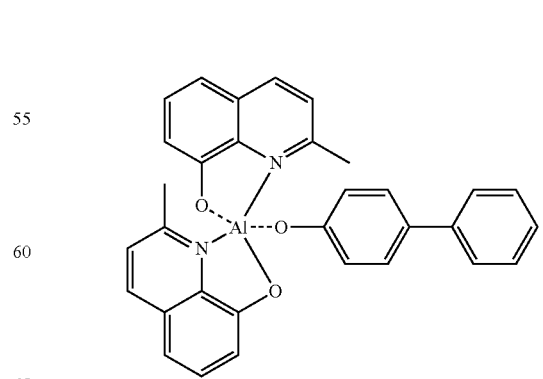

BAlq

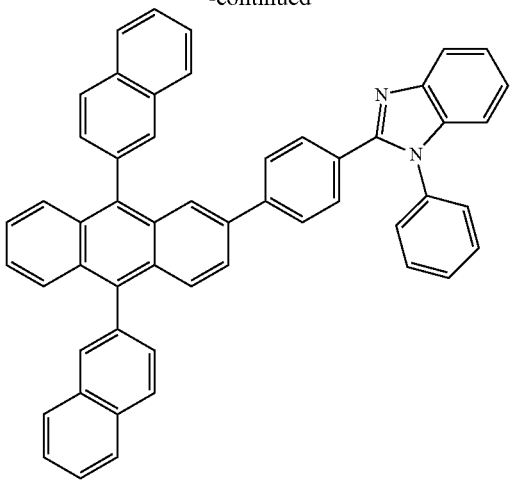

Compound 201

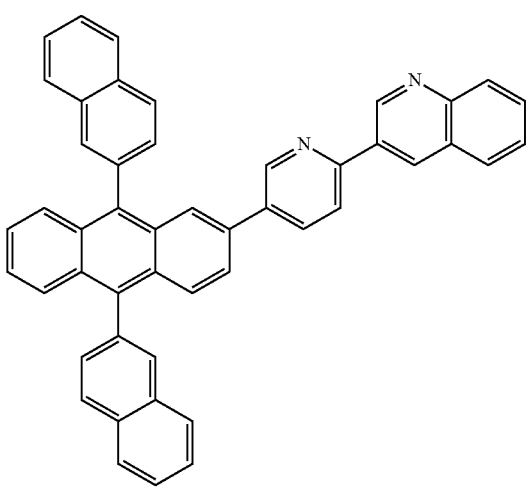

Compound 202

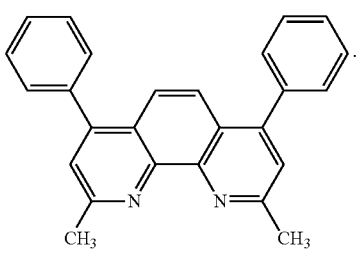

BCP

In some embodiments, the thickness of the ETL may be about 100 Å to about 1,000 Å, for example, about 150 Å to about 500 Å. In these embodiments, suitable electron transport properties may be obtained without a substantial increase in driving voltage.

The ETL may further include a metal-containing material, in addition to the amine-based compound described above.

The metal-containing material may include a Li-complex. Non-limiting examples of the Li-complex include lithium quinolates (LiQ) and Compound 203:

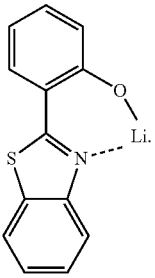

Compound 203

Also, an EIL, which may facilitate electron injection from the second electrode 17 (cathode), may be formed on the ETL.

The material for forming the EIL may include any suitable commonly used EIL forming material, such as LiF, NaCl, CsF, Li$_2$O, or BaO. The EIL deposition conditions may vary according to the compound used to form the EIL. The conditions for forming the EIL may be similar to the conditions for forming the HIL.

In some embodiments, the thickness of the EIL may be about 1 Å to about 100 Å, for example, about 3 Å to about 90 Å. In these embodiments, suitable electron injection properties may be obtained without a substantial increase in driving voltage.

A second electrode 17 may be formed on the organic layer 15. The second electrode 17 may be a cathode, which is an electron injection electrode. In this regard, a material for forming the second electrode 17 may include a metal having low work function, such as a metal, an alloy, an electrically conducting compound, or a combination thereof. In particular, a thin film of lithium (Li), magnesium (Mg), aluminum (Al), aluminum-lithium (Al—Li), calcium (Ca), magnesium-indium (Mg—In), or magnesium-silver (Mg—Ag) may be used as the material for forming the second electrode. In a top-emission type OLED, the second electrode 17 may be formed as a transparent electrode using ITO or IZO.

Although the OLED has been described with reference to FIG. 1, the OLED is not limited thereto.

In some embodiments, the first electrode 13 shown in FIG. 1 may be a cathode, the second electrode 17 may be an anode, an electron transporting region may be included between the first electrode 13 and the EML, and a hole transporting region may be included between the EML and the second electrode 17.

An HBL may be formed between the EML and the ETL by vacuum deposition, spin coating, casting or LB deposition to prevent or reduce diffusion of triplet excitons and/or holes to the ETL. When the HBL is formed by vacuum deposition or spin coating, the conditions may vary according to the compound used to form the HBL. The conditions for forming the HBL may be similar to the conditions for forming the HIL. The HBL may include any suitable commonly used hole blocking material. Non-limiting examples of the hole blocking material include an oxadiazole derivative, a triazole derivative, and a phenanthroline derivative. For example, BCP may be used as a hole blocking material:

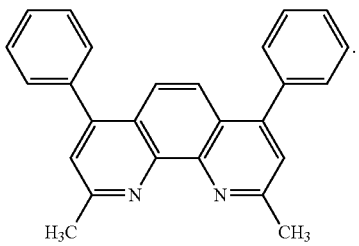

BCP

In some embodiments, the thickness of the HBL may be about 20 Å to about 1,000 Å, for example, about 30 Å to about 300 Å. In these embodiments, suitable hole blocking properties may be obtained without a substantial increase in driving voltage.

Hereinafter, examples of the substituents described above are provided. In this regard, it is understood that the numbers of carbon atoms listed for the substituents are presented only for illustrative purposes and do not limit the characteristics of the substituents. Definitions of substituents not provided in the present specification are the same as the general definitions of those substituents as understood by one of ordinary skill in the art.

Non-limiting examples of the $C_1$-$C_{60}$ alkyl group include a linear or branched $C_1$-$C_{60}$ alkyl group, such as methyl, ethyl, propyl, isobutyl, sec-butyl, pentyl, iso-amyl, hexyl, and the like. The $C_1$-$C_{60}$ alkylene group refers to a divalent group, which otherwise has the same structure as the $C_1$-$C_{60}$ alkyl group.

The $C_1$-$C_{60}$ alkoxy group refers to a moiety represented by —OA (where, A is the $C_1$-$C_{60}$ alkyl group). Non-limiting examples of the $C_1$-$C_{60}$ alkoxy group include methoxy, ethoxy, and isopropoxy.

The $C_2$-$C_{60}$ alkenyl group refers to a moiety including at least one carbon-carbon double bond in the $C_2$-$C_{60}$ alkyl group. The carbon-carbon double bond (i.e., an alkene) may be an internal alkene or a terminal alkene. The internal alkene may be in the form of an E isomer, a Z isomer, or a mixture thereof. Examples of the $C_2$-$C_{60}$ alkenyl group include ethenyl, propenyl, and butenyl. The $C_2$-$C_{60}$ alkenylene group refers to a divalent group, which otherwise has the same structure as the $C_2$-$C_{60}$ alkenyl group.

The $C_2$-$C_{60}$ alkynyl group refers to a moiety including at least one carbon triple bond in the $C_2$-$C_{60}$ alkyl group. The carbon-carbon triple bond (i.e., an alkyne) may be an internal alkyne or a terminal alkyne. Non-limiting examples of the $C_2$-$C_{60}$ alkynyl group include ethynyl and propynyl. The $C_2$-$C_{60}$ alkynylene group refers to a divalent group, which otherwise has the same structure as the $C_2$-$C_{60}$ alkynyl group.

The $C_3$-$C_{10}$ cycloalkyl group refers to a cycloalkyl group having 3 to 10 carbons. Non-limiting examples of the $C_3$-$C_{10}$ cycloalkyl group include a cyclopentyl group, a cyclohexyl group, and a cycloheptyl group. The $C_3$-$C_{10}$ cycloalkylene group refers to a divalent group, which otherwise has the same structure as the $C_3$-$C_{10}$ cycloalkyl group.

The $C_2$-$C_{10}$ heterocycloalkyl group refers to a cycloalkyl group including at least one heteroatom, such as N, S, O, or P, and having 3 to 10 carbons. Non-limiting examples of the $C_2$-$C_{10}$ heterocycloalkyl group include tetrahydrofuranyl and tetrahydrothiophenyl. The $C_2$-$C_{10}$ heterocycloalkylene group refers to a divalent group, which otherwise has the same structure as the $C_2$-$C_{10}$ heterocycloalkyl group.

The $C_3$-$C_{10}$ cycloalkenyl group refers to a cycloalkenyl group having 3 to 10 carbons. Non-limiting examples of the $C_3$-$C_{10}$ cycloalkenyl group include cyclopentenyl, cyclohexenyl, and cycloheptenyl. The $C_3$-$C_{10}$ cycloalkenyl group refers to a divalent group, which otherwise has the same structure as the $C_3$-$C_{10}$ cycloalkenyl group.

The $C_2$-$C_{10}$ heterocycloalkenyl group refers to a cycloalkenyl group including at least one heteroatom, such as N, S, O, or P, and having 3 to 10 carbons. Non-limiting examples of the $C_2$-$C_{10}$ heterocycloalkenyl group include 2,3-dihydrofuranyl and 2,3-dihydrothiophenyl. The $C_2$-$C_{10}$ heterocycloalkenylene group refers to a divalent group, which otherwise has the same structure as the $C_2$-$C_{10}$ heterocycloalkenyl group.

The $C_6$-$C_{60}$ aryl group refers to a monovalent group including at least one aromatic ring and having a carbocyclic system that includes 6 to 60 carbons. The $C_6$-$C_{60}$ arylene group refers to a divalent group, which otherwise has the same structure as the $C_6$-$C_{60}$ aryl group. When the $C_6$-$C_{60}$ aryl group and the $C_6$-$C_{60}$ arylene group include at least two rings, the rings may be fused to each other or connected to each other via a single bond.

The substituted $C_6$-$C_{60}$ aryl group refers to the substitution of at least one hydrogen atom of the $C_6$-$C_{60}$ aryl group with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, —N($Q_{11}$)($Q_{12}$), or —Si($Q_{13}$)($Q_{14}$)($Q_{15}$). Non-limiting examples of the $C_6$-$C_{60}$ aryl group include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m-, or p-fluorophenyl group, a dichlorophenyl group), a dicyanophenyl group, a trifluoromethoxyphenyl group, an o-, m-, or p-tolyl group, an o-, m-, or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkyl naphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthyl group, a phenalenyl group, a fluorenyl group, a methylanthracenyl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, and an ovalenyl group.

The $C_1$-$C_{60}$ heteroaryl group refers to a monovalent group including at least one heteroatom, such as N, O, P, or S, with all of the remaining ring atoms being C, and including an aromatic ring. The $C_1$-$C_{60}$ heteroarylene group refers to a divalent group, which otherwise has the same structure as the $C_1$-$C_{60}$ heteroaryl group. When the $C_1$-$C_{60}$ heteroaryl group and the $C_1$-$C_{60}$ heteroarylene group include at least two rings, the rings may be fused to each other or connected to each other via a single bond.

Non-limiting examples of the $C_1$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group.

The $C_6$-$C_{60}$ aryloxy group refers to a —$OA_2$ moiety, where $A_2$ is the $C_6$-$C_{60}$ aryl group. The $C_6$-$C_{60}$ arylthio group refers to a —$SA_3$ moiety, where $A_3$ is the $C_6$-$C_{60}$ aryl group.

As used herein, the term "substituted" refers to substitution of a hydrogen atom on a group with a substituent other than hydrogen, such as those substgituents described above with respect to the substituted aryl group.

Hereinafter, the amine-based compound and the OLED according to an embodiment of the present invention will be described with reference to the following Synthesis Examples and other Examples. However, these Synthesis Examples and other Examples are presented for illustrative purposes only and do not limit the scope of the present invention. In the Synthesis Examples, when B was used instead of A, the amount of B used and the amount of A used were the same in terms of moles (e.g., based on a molar equivalent).

Synthesis Example 1

Synthesis of Compound 1

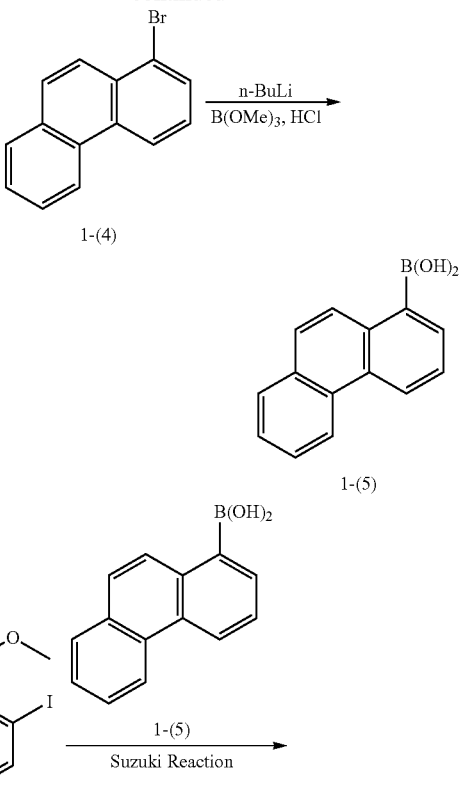

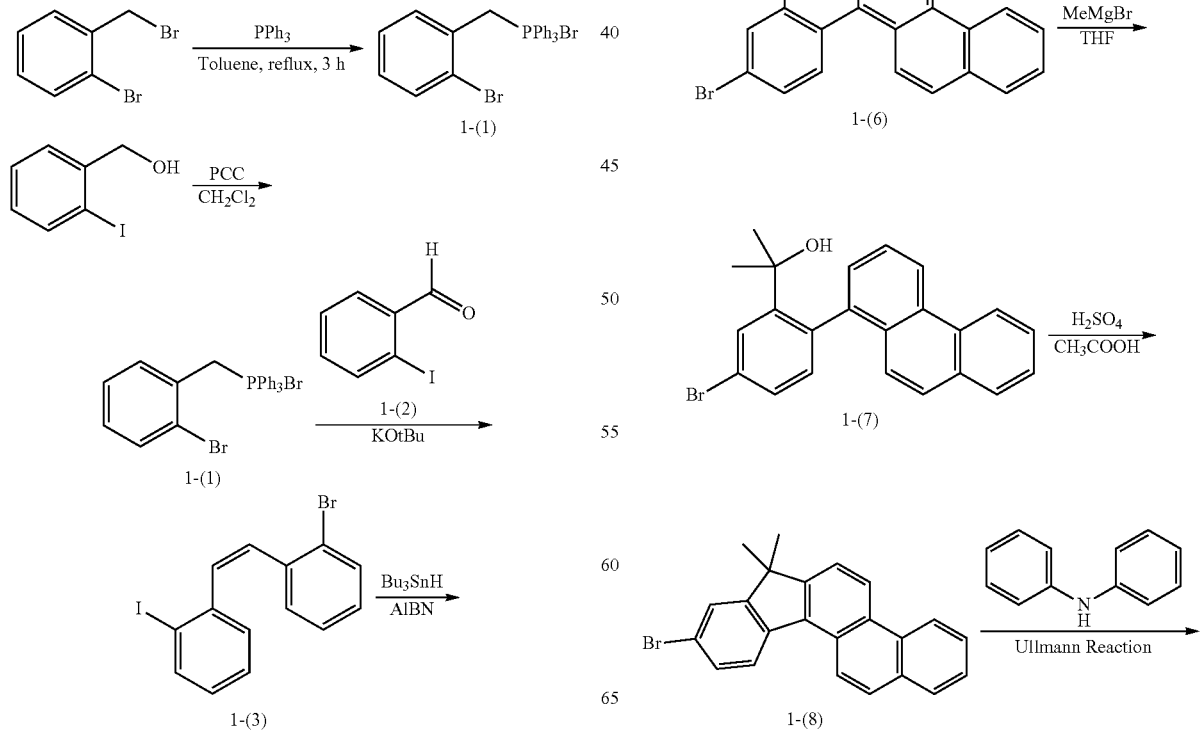

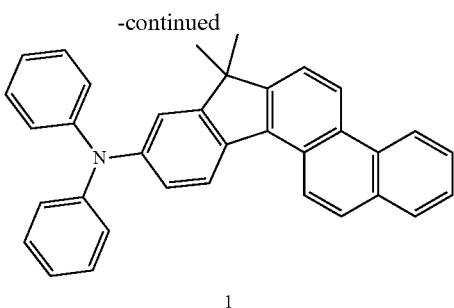

Synthesis of Intermediate 1-(1)

10 g (40 mmol) of 2-bromobenzyl bromide and 12.58 g (48 mmol) of triphenylphophine were added to 500 mL of toluene, and then heat-stirred for 3 hours. When the reaction was complete, the mixture was cooled to room temperature, and then the precipitate was filtered and washed with hexane to provide 19.6 g of Intermediate 1-(1) (2-bromobenzyl)triphenylphosphonium bromide) was obtained as a white solid (yield: 96.1%).

1H NMR (300 MHz, CDCl3): δ (ppm) 7.83~7.21 (m, 16H), 7.38 (d, J=7.8 Hz, 1H), 7.17 (m, 2H), 5.74 (d, J=14.4 Hz, 2H)

A molecular weight: Theoretical value for $C_{25}H_{21}BrP+$ 431.0559

LR-Mass (EI+): 431.0, HR-Mass (FAB+): 431.0564

Synthesis of Intermediate 1-(2)

10 g (42.73 mmol) of 2-iodobenzylalcohol was added to 200 mL of dichloromethane, 10.13 g (47 mmol) of pyridine chlorochromate (PCC) was added thereto, and was then stirred at room temperature. When the reaction was complete, the solvent was removed, and column chromatography (ethyl acetate: hexane=1:8) was used to obtain 9.1 g of Intermediate 1-(2) (2-iodobenzaldehyde) as a yellow liquid (yield: 92%).

1H NMR (300 MHz, CDCl3): δ (ppm) 10.09 (s, 1H), 7.94 (dd, J=15.0, 7.2 Hz, 2H), 7.48 (s, 1H), 7.30 (s, 1H)

A molecular weight for $C_7H_5IO$: Cal. 231.9385

LR-Mass (EI+): 232.0, HR-Mass (EI+): 231.9393

Synthesis of Intermediate 1-(3)

33 g (64.425 mmol) of Intermediate 1-(1) (2-bromobenzyl)triphenylphosphonium bromide) in 350 mL of tetrahydrofuran were stirred at a temperature of 0° C. under a nitrogen atmosphere. A mixture including 8.434 g (75.163 mmol) of potassium tert-butoxide and 50 mL of tetrahydrofuran was added thereto. Next, a mixture of 12.457 g (53.688 mmol) of Intermediate 1-(2) (2-iodobenzaldehyde) and 100 mL of tetrahydrofuran was added dropwise, and the temperature of the resulting mixture was slowly increased to room temperature, and then stirred for 24 hours. When the reaction was complete, 100 mL of H2O was added, and the organic layer was separated using an excess amount of diethyl ether and H2O, and washed with a saturated sodium chloride solution. The organic layer was dried with sodium sulfate and filtered. The solvent was removed from the resultant obtained after the drying and filtering, and column chromatography was then performed using hexane to obtain 18.7 g of Intermediate 1-(3) ((Z)-1-bromo-2-(2-iodostyryl)benzene) as a white solid (yield: 90.5%).

1H NMR (300 MHz, CDCl3): δ (ppm) 7.87 (dd, J=7.9, 1.1 Hz, 1H), 7.57 (dd, J=7.3, 1.8 Hz, 1H), 7.11-6.93 (m, 5H), 6.89 (td, J=7.7, 1.9 Hz, 1H), 6.76 (d, J=11.8 Hz, 1H), 6.68 (d, J=11.8 Hz, 1H)

13C NMR (75 MHz, CDCl3): δ (ppm) 140.9, 139.2, 137.0, 135.4, 132.8, 131.1, 130.8, 130.6, 129.0, 128.9, 128.0, 127.1, 124.3, 100.0

A molecular weight for $C_{14}H_{10}BrI$: Cal. 383.9011

LR-Mass (EI+): 384.1, HR-Mass (EI+): 383.9018

Synthesis of Intermediate 1-(4)

15.1 g (39.217 mmol) of Intermediate 1-(3) ((Z)-1-bromo-2-(2-iodostyryl)benzene), 13.697 g (47.060 mmol) of tributyltin hydride, and 1.288 g (7.843 mmol) of azobisisobutyronitrile (AlBN) were heat-stirred in 200 mL of toluene under a nitrogen atmosphere. After 12 hours, the mixture was slowly cooled to room temperature, and 2.283 g (7.843 mmol) of tributyl hydride and 0.258 g (1.569 mmol) of AlBN were then added and the resulting mixture was heat-stirred. When the reaction was complete, the toluene was removed, and the organic layer was separated using an excess amount of dichloromethane and H2O. Next, potassium fluoride and celite were used to remove the tin salt, and the organic layer was then dried with sodium sulfate and filtered. After the drying and filtering, the solvent was removed and column chromatography was performed with hexane to obtain 8.4 g of Intermediate 1-(4) (bromophenanthrene) as a white solid (yield: 83.3%).

1H NMR (300 MHz, CDCl3): δ (ppm) 8.68 (d, J=8.2 Hz, 2H), 8.23 (d, J=9.2 Hz, 1H), 7.95~6.89 (m, 2H), 7.86 (d, J=9.2 Hz, 1H), 7.73~7.62 (m, 2H), 7.50 (dd, J=8.2, 7.9 Hz, 1H)

13C NMR (75 MHz, CDCl3): δ (ppm) 132.2, 132.1, 130.9, 130.8, 130.1, 128.9, 128.7, 127.4, 127.3, 127.0, 125.5, 123.9, 123.1, 122.5

A molecular weight for $C_{14}H_9Br$: Cal. 255.9888

LR-Mass (EI+): 256.0, HR-Mass (EI+): 255.9886

Synthesis of Intermediate 1-(5)

3 g (11.667 mmol) of Intermediate 1-(4) (1-bromophenanthrene) was added into a round bottom flask having two necks, sealed, and then dried at a reduced pressure. 100 mL of purified tetrahydrofuran was added, and a temperature of the mixture was maintained at −78° C. by using dry ice and acetone. 11.667 mL (29.168 mmol) of an n-butyl lithium solution (2.5 mol/L in hexane) was slowly injected into the flask and stirred while maintaining the temperature. Then 6.539 mL (58.336 mmol) of trimethyl borate was added and the resulting mixture was stirred while slowly increasing the temperature to room temperature. After 5 hours, an excess amount of 1N HCl (20 mL) was added, followed by stirring for 2 hours. When the reaction was complete, the organic layer was separated using an excess of dichloromethane and H2O. Next, the organic layer was dried with sodium sulfate and filtered. After drying and filtering, the solvent was removed and column chromatography (dichloromethane: methanol=9:1) was performed to obtain 1.8 g of Intermediate 1-(5) ((phenanthren-1-yl)boronic acid) as a white solid (yield: 69.5%).

1H NMR (300 MHz, acetone-d6): δ (ppm) 8.88 (dd, J=8.4, 5.4 Hz, 2H), 8.51 (d, J=9.0 Hz, 1H), 7.97 (d, J=7.2 Hz, 2H), 7.82 (d, J=9.0 Hz, 1H), 7.71~7.60 (m, 3H)

13C NMR (75 MHz, acetone-d6): δ (ppm) 135.0, 132.8, 131.8, 130.6, 128.3, 127.7, 126.5, 126.4, 126.3, 125.7, 124.0, 122.7

A molecular weight for $C_{14}H_{11}BO_2$: Cal. 222.0852

LR-Mass (EI+): 222.0, HR-Mass (EI+): 222.0848

Synthesis of Intermediate 1-(6)

3.849 g (11.259 mmol) of methyl 5-bromo-2-iodobenzoate, 3 g (13.510 mmol) of Intermediate 1-(6) (phenanthren-1-ylboronic acid), 30 mL of 2 mol/L potassium carbonate in H2O, and 0.651 g (0.563 mmol) of tetrakis(triphenylphosphine)palladium were added to 100 mL of tetrahydrofuran and 30 mL of methanol under a nitrogen atmosphere and then heat-stirred. After 24 hours, completion of the reaction was confirmed through TLC, and the solvent was removed and filtered using celite. Next, the organic layer was separated using dichloromethane and $H_2O$ and washed with a saturated sodium chloride solution. The organic layer was dried with sodium sulfate and filtered. After drying and filtering, the solvent was removed and column chromatography (MC:hexane=1:4) was performed to obtain 3.5 g of Intermediate 1-(6) as a white solid (yield: 79%).

1H NMR (300 MHz, $CDCl_3$): δ (ppm) 8.80 (d, J=12.6 Hz, 2H), 8.22 (s, 1H), 7.88 (d, J=7.8 Hz, 1H), 7.77 (dd, J=5.1, 1.8 Hz, 1H), 7.73~7.60 (m, 4H), 7.40 (dd, J=7.8, 1.5 Hz, 2H), 7.32 (d, J=8.1 Hz, 1H), 3.41 (s, 3H)

13C NMR (75 MHz, $CDCl_3$): δ (ppm) 166.4, 140.7, 139.0, 134.6, 133.5, 133.1, 131.7, 130.3, 130.2, 130.0, 128.5, 127.2, 126.8, 126.7, 125.7, 123.9, 122.9, 122.4, 121.5, 52.1

A molecular weight for $C_{22}H_{15}BrO_2$: Cal. 390.0255

LR-Mass (EI+): 392.2, HR-Mass (EI+): 392.0257

Synthesis of Intermediate 1-(7)

3.45 g (8.818 mmol) of Intermediate 1-(6) (methyl 5-bromo-2-(phenanthren-1-yl)benzoate) was added into a round bottom flask having two necks, sealed, and then dried at a reduced pressure. 120 mL of purified tetrahydrofuran was added, and 14.85 mL (21.162 mmol) of a methyl magnesium bromide solution (1.4 mol/L) was slowly injected into the flask. The resulting mixture was heat-stirred for 4 hours and the solvent was removed. Next, the organic layer was separated using dichloromethane and $H_2O$ and washed with a saturated sodium chloride solution. The organic layer was dried with sodium sulfate and filtered. After drying and filtering, the solvent was removed and column chromatography (MC:hexane=1:9) was performed to obtain 2.7 g of Intermediate 1-(7) (2-(5-bromo-2-(phenanthren-1-yl)phenyl)propan-2-ol) as a white solid (yield: 75%).

1H NMR (300 MHz, CDCl3): δ (ppm) 8.77 (d, J=5.1 Hz, 2H), 8.03 (d, J=1.8 Hz, 1H), 7.89 (d, J=4.5 Hz, 1H), 7.88~7.62 (m, 4H), 7.52~7.47 (m, 2H), 7.33 (d, J=9.3 Hz, 2H), 7.03 (d, J=8.1 Hz, 1H), 1.39 (s, 3H), 1.22 (s, 3H)

13C NMR (75 MHz, CDCl3): δ (ppm) 149.5, 140.4, 1367, 134.2, 131.7, 131.0, 130.5, 130.2, 129.6, 129.4, 128.6, 128.0, 127.2, 126.9, 125.4, 125.0, 122.9, 122.5, 122.1, 73.7, 32.3, 31.7

A molecular weight for $C_{23}H_{19}BrO$: Cal. 390.0619

LR-Mass (EI+): 390.0, HR-Mass (EI+): 390.0622

Synthesis of Intermediate 1-(8)

4.5 mL of sulfuric acid in 130 mL of acetic acid, as a solvent was added to 2.7 g (6.918 mmol) of Intermediate 1-(7) (2-(5-bromo-2-(phenanthren-1-yl)phenyl)propan-2-ol), and the resulting mixture was heat-stirred for 3 hours. After the reaction was complete, the mixture was slowly cooled to room temperature, and 50 mL of $H_2O$ was added, following by stirring. Next, the organic layer was separated using dichloromethane and $H_2O$, washed with a saturated sodium chloride solution, and the organic layer was then dried. The solvent was then removed and column chromatography was performed to obtain 2.7 g of Intermediate 1-(8) (9-bromo-7,7-dimethyl-7H-indeno[1,2-a]phenanthrene) as a white solid (yield: 75%).

1H NMR (300 MHz, $CDCl_3$): δ (ppm) 8.76 (t, J=5.4 Hz, 2H), 8.63 (d, J=9.3 Hz, 1H), 8.24 (d, J=8.4 Hz, 1H), 7.74 (d, J=8.7 Hz, 1H), 7.97~7.91 (m, 2H), 7.71~7.59 (m, 4H), 1.59 (s, 6H)

13C NMR (75 MHz, $CDCl_3$): δ (ppm) 157.0, 152.7, 130.2, 128.6, 127.9, 126.9, 126.7, 126.5, 126.2, 124.7, 123.0, 122.3, 120.9, 120.7, 46.6, 26.9

A molecular weight for $C_{23}H_{17}Br$: Cal. 372.0514

LR-Mass (EI+): 372.0, HR-Mass (EI+): 372.0514

Synthesis of Compound 1

2.65 g (7.099 mmol) of Intermediate 1-(8) (9-bromo-7,7-dimethyl-7H-indeno[1,2-a]phenanthrene), 1.561 g (9.229 mmol) of diphenylamine, and 0.111 g (0.497 mmol) of palladium acetate were added into a round bottom flask having two necks, sealed, and then dried at a reduced pressure. 80 mL of purified tetrahydrofuran was injected into the flask, and the contents of the flask were stirred. 0.287 g (1.420 mmol) of tri-tert-butylphosphine and 3.187 g (28.389 mmol) of potassium tert-butoxide were mixed and dissolved in 20 mL of toluene, and the mixture was slowly injected into the flask by using a syringe. The resulting mixture was then heat-stirred at a temperature of 100° C. for 12 hours. After the reaction was complete, the solvent was removed, and the resultant was filtered with celite. Next, the organic layer was separated using dichloromethane and $H_2O$, washed with a saturated sodium chloride solution, and the organic layer was dried. The solvent was removed after drying and column chromatography was performed with a chlorinated solvent to obtain 2.15 g of Compound 1 (7,7-dimethyl-N,N-diphenyl-7H-Indeno[1,2-a]phenanthren-9-amine) as a white solid (yield: 66%).

1H NMR (400 MHz, CDCl3): δ (ppm) 8.66 (d, J=8.4 Hz, 1H), 8.61 (d, J=8.4 Hz, 1H), 8.56 (d, J=9.2 Hz, 1H), 8.14 (d, J=8.0 Hz, 1H), 7.84 (d, J=8.0 Hz, 1H), 7.79 (d, J=9.6 Hz, 1H), 7.64 (d, J=8.0 Hz, 1H), 7.59 (t, J=7.2 Hz, 1H), 7.52 (t, J=7.2 Hz, 1H), 7.26~7.18 (m, 6H), 7.12~7.05 (m, 4H), 6.98 (t, J=7.2 Hz, 2H), 1.43 (s, 6H)

13C NMR (100 MHz, CDCl3): δ (ppm) 157.0, 152.7, 130.2, 128.6, 127.9, 126.9, 126.7, 126.5, 126.2, 124.7, 123.0, 122.3, 120.9, 120.7, 46.6, 26.9

A molecular weight for $C_{35}H_{27}N$: Cal. 461.2143

LR-Mass (EI+): 461.0, HR-Mass (EI+): 461.2147

Synthesis Example 2

Synthesis of Compound 5

Compound 5 was synthesized as in Synthesis Example 1, except that bis(4-(trimethylsilyl)phenyl)amine was used instead of diphenylamine in the synthesis of Compound 1.

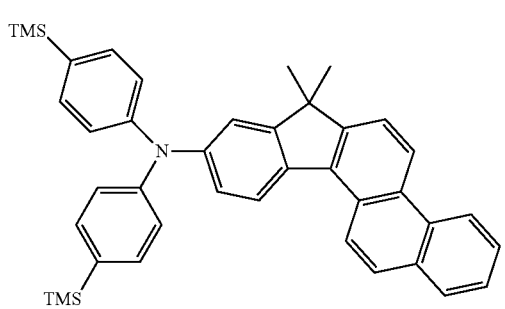

5

1H NMR (400 MHz, CDCl3): δ (ppm) 8.66 (d, J=8.4 Hz, 1H), 8.61 (d, J=8.4 Hz, 1H), 8.56 (d, J=9.2 Hz, 1H), 8.14 (d, J=8.0 Hz, 1H), 7.84 (d, J=8.0 Hz, 1H), 7.79 (d, J=9.6 Hz, 1H), 7.64 (d, J=8.0 Hz, 1H), 7.59 (t, J=7.2 Hz, 1H), 7.52 (t, J=7.2 Hz, 1H), 7.46~7.38 (m, 6H), 6.78 (m, 4H), 1.43 (s, 6H), 0.46 (s, 18H)

A molecular weight for $C_{41}H_{43}NSi_2$: Cal. 605,29

Synthesis Example 3

Synthesis of Compound 15

Compound 15 was synthesized as in Synthesis Example 1, except that Intermediate 15-(8) was used instead of diphenylamine in the synthesis of Compound 1.
Intermediate 15-(8)

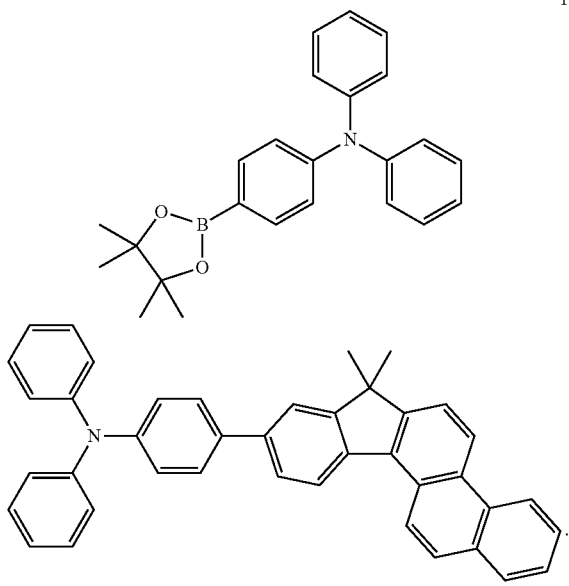

1H NMR (400 MHz, CDCl3): δ (ppm) 8.66 (d, J=8.4 Hz, 1H), 8.61 (d, J=8.4 Hz, 1H), 8.56 (d, J=9.2 Hz, 1H), 8.14 (d, J=8.0 Hz, 1H), 7.84 (d, J=8.0 Hz, 1H), 7.79 (d, J=9.6 Hz, 1H), 7.64 (d, J=8.0 Hz, 1H), 7.59 (t, J=7.2 Hz, 1H), 7.52 (m, 3H), 7.43~7.18 (m, 6H), 6.58~6.38 (m, 8H), 1.43 (s, 6H)
A molecular weight for $C_{41}H_{31}N$: Cal. 537.69

Synthesis Example 4

Synthesis of Compound 14

Compound 14 was synthesized as in Synthesis Example 1, except that Intermediate 14-(8) was used instead of diphenylamine in the synthesis of Compound 1.
Intermediate 14-(8)

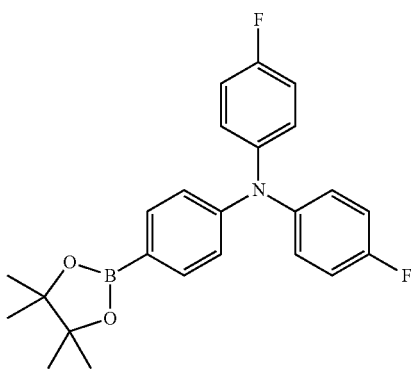

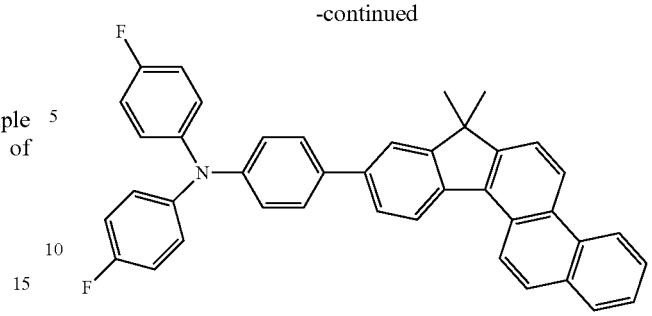

1H NMR (400 MHz, CDCl3): δ (ppm) 8.66 (d, J=8.4 Hz, 1H), 8.61 (d, J=8.4 Hz, 1H), 8.56 (d, J=9.2 Hz, 1H), 8.24 (d, J=8.0 Hz, 1H), 8.04 (d, J=8.0 Hz, 1H), 7.89 (d, J=9.6 Hz, 1H), 7.74 (d, J=8.0 Hz, 1H), 7.65 (t, J=7.2 Hz, 1H), 7.53 (m, 3H), 7.23~6.98 (m, 6H), 6.38~6.18 (m, 6H), 1.43 (s, 6H)
A molecular weight for $C_{41}H_{29}NF_2$: Cal. 573.67

Synthesis Example 5

Synthesis of Compound 11

Compound 11 was synthesized as in Synthesis Example 1, except that Intermediate 11-(8) was used instead of diphenylamine in the synthesis of Compound 1.
Intermediate 11-(8)

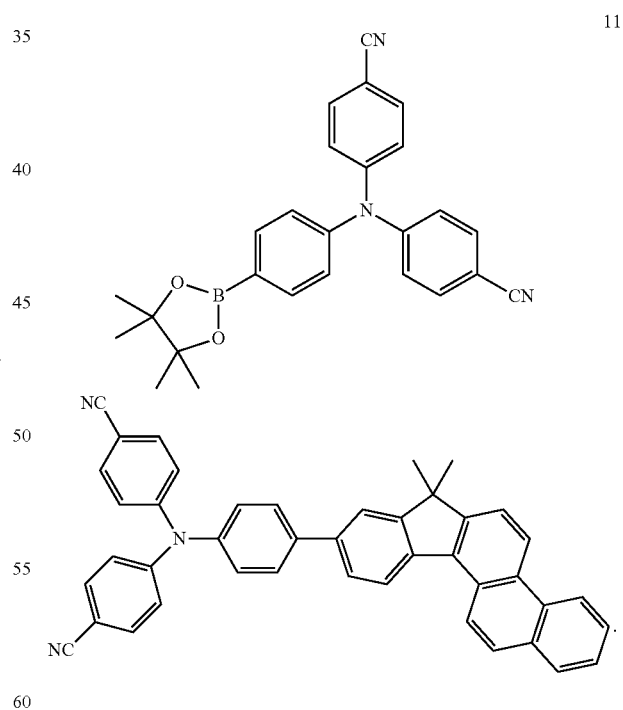

1H NMR (400 MHz, CDCl3): δ (ppm) 8.66 (d, J=8.4 Hz, 1H), 8.61 (d, J=8.4 Hz, 1H), 8.56 (d, J=9.2 Hz, 1H), 8.24 (d, J=8.0 Hz, 1H), 8.04 (d, J=8.0 Hz, 1H), 7.89 (d, J=9.6 Hz, 1H), 7.74 (d, J=8.0 Hz, 1H), 7.65 (t, J=7.2 Hz, 1H), 7.49 (m, 3H), 7.21~6.78 (m, 6H), 6.48~6.28 (m, 6H), 1.43 (s, 6H)
A molecular weight for $C_{43}H_{29}N_3$: Cal. 587.71

Evaluation Example 1

Evaluation of Light-Emitting Characteristics of Compound 1

Figure 2:
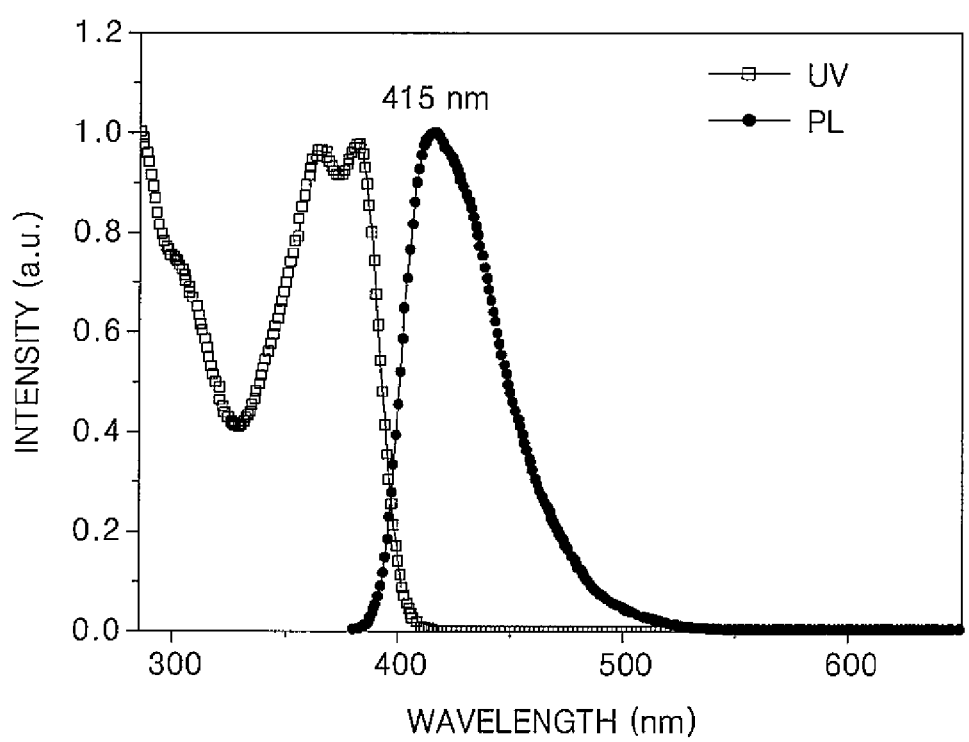
FIG. 2 is a UV absorption spectrum and a PL spectrum of Compound 1 prepared according to Synthesis Example 1 in a solution.

The light-emitting characteristics of Compound 1 were evaluated by analyzing the UV absorption spectrum and a photoluminescence (PL) spectrum of Compound 1 synthesized according to Synthesis Example 1, and the results are shown in FIG. 2. Compound 1 was diluted in toluene to a concentration of 0.2 mM. The UV absorption spectrum of Compound 1 in solution was measured by using a spectrometer (Shimadzu UV-350 Spectrometer). Then, Compound 1 was diluted in toluene to a concentration of 10 mM to measure the PL spectrum of Compound 1 in solution by using a spectrofluorometer (ISC PC1 Spectrofluorometer) equipped with a xenon lamp.

Referring to FIG. 2, Compound 1 had good UV absorption characteristics and good PL light-emission characteristics.

Example 1

An ITO/Ag/ITO substrate was cut to a size of 50 mm×50 mm×0.7 mm and washed with ultrasonic waves in isopropyl alcohol and pure water for 5 minutes each. Then, the substrate was irradiated with UV light for 10 minutes and exposed to ozone to be cleaned. The resulting glass substrate was mounted in a vacuum deposition apparatus.

Compound 301 was vacuum deposited on the ITO/Ag/ITO anode to form an HIL having a thickness of 600 Å, and Compound 311 was vacuum deposited on the HIL to form an HTL having a thickness of 200 Å.

ADN (host) and Compound 1 (dopant) were co-deposited on the HTL at a weight ratio of 200:6 to form an EML having a thickness of 200 Å. Compound 201 was co-deposited on the EML to form an ETL having a thickness of 300 Å. LiQ was vacuum deposited on the ETL to form an EIL having a thickness of 10 Å. Mg and Ag were co-deposited on the EIL to form a cathode having a thickness of 160 Å.

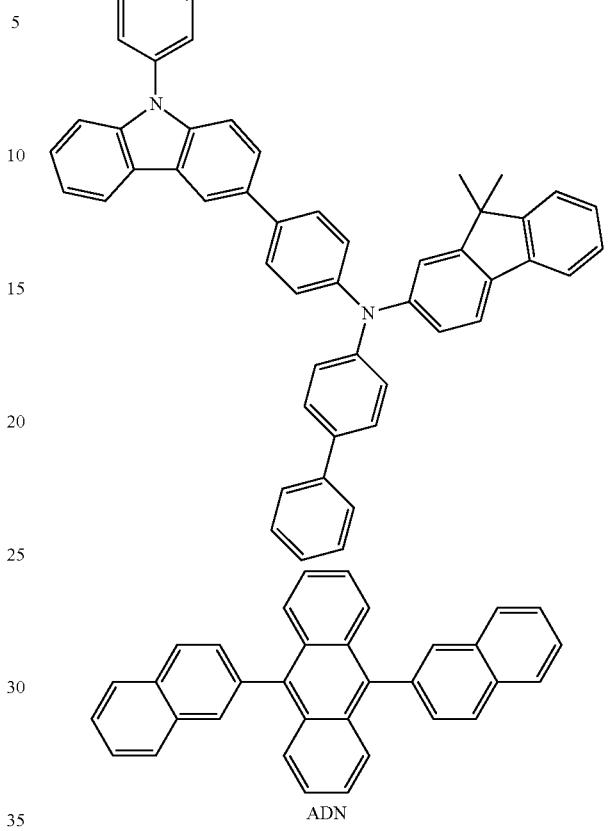

311

ADN

Compound 201

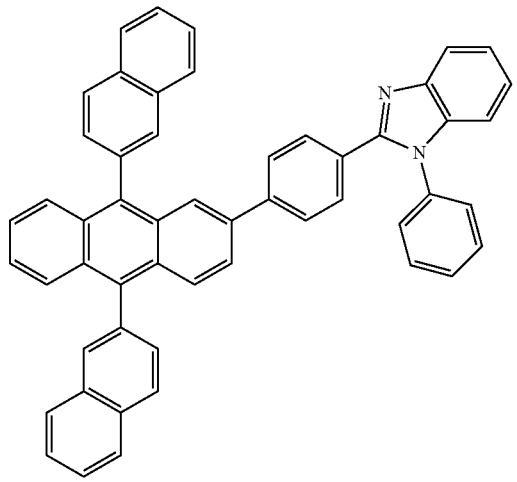

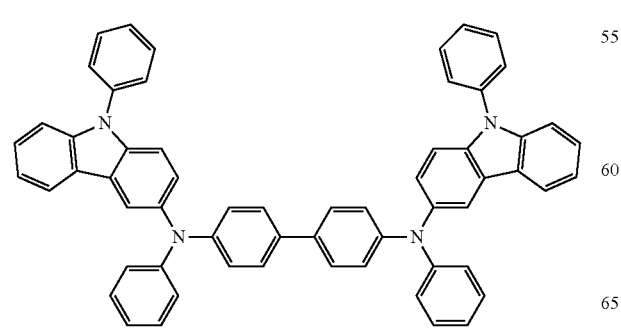

301

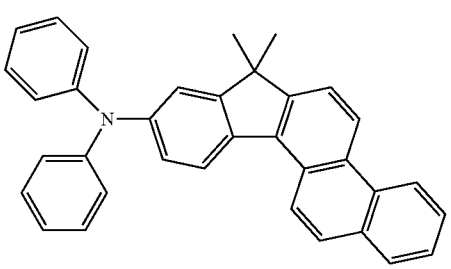

1

Example 2

An OLED was manufactured as in Example 1, except that Compound 5 was used instead of Compound 1 as the dopant in the formation of the EML.

Example 3

An OLED was manufactured as in Example 1, except that Compound 15 was used instead of Compound 1 as the dopant in the formation of the EML.

Example 4

An OLED was manufactured as in Example 1, except that Compound 14 was used instead of Compound 1 as the dopant in the formation of the EML.

Example 5

An OLED was manufactured as in Example 1, except that Compound 11 was used instead of Compound 1 as the dopant in the formation of the EML.

Comparative Example 1

An OLED was manufactured as in Example 1, except that Compound A was used instead of Compound 1 as the dopant in the formation of the EML:

Compound A

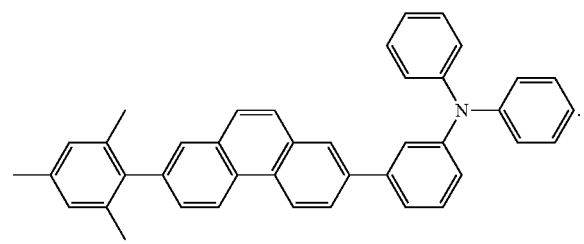

Comparative Example 2

An OLED was manufactured as in Example 1, except that Compound B was used instead of Compound 1 as the dopant in the formation of the EML:

Compound B

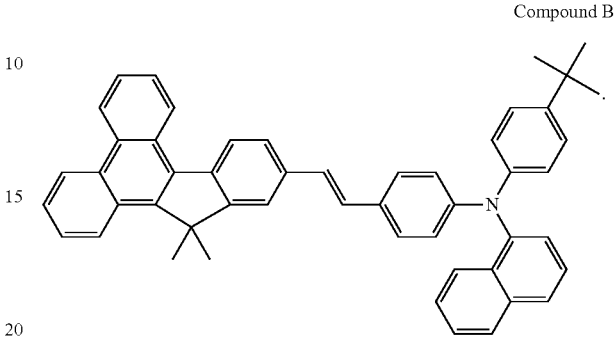

Evaluation Example 2

Evaluation of Characteristics of OLED

The driving voltage, current density, brightness, emission color coordinates, efficiency, and half-lifetime of each of the OLEDs prepared according to Examples 1 to 5 and Comparative Examples 1 and 2 were evaluated by supplying power from a current-voltage meter (Keithley SMU 236) and using a photometer (PR650 Spectrascan Source Measurement Unit (available from PhotoResearch)). The results are shown in Table 1.

TABLE 1

| | Host | Dopant | Driving voltage (V) | Current density (mA/cm$^2$) | Light-emitting efficiency (cd/A) | Color coordinate CIE x | CIE y |
|---|---|---|---|---|---|---|---|
| Example 1 | ADN | Compound 1 | 4.2 | 16.8 | 2.5 | 0.140 | 0.029 |
| Example 2 | ADN | Compound 5 | 4.1 | 17.2 | 2.2 | 0.133 | 0.030 |
| Example 3 | ADN | Compound 15 | 4.3 | 15.6 | 3.1 | 0.137 | 0.040 |
| Example 4 | ADN | Compound 14 | 4.5 | 16.2 | 3.2 | 0.140 | 0.042 |
| Example 5 | ADN | Compound 11 | 4.0 | 16.7 | 3.0 | 0.142 | 0.039 |
| Comparative Example 1 | ADN | Compound A | 4.5 | 18.2 | 2.0 | 0.149 | 0.098 |
| Comparative Example 2 | ADN | Compound B | 4.6 | 18.9 | 1.9 | 0.152 | 0.109 |

Referring to Table 1, the OLEDs of Examples 1 to 5 have improved driving voltages, light-emitting efficiencies, and color purities compared to the OLEDs of Comparative Examples 1 and 2.

As described herein, according to the one or more embodiments of the present invention, an amine-based compound has good electrical characteristics, light-emitting characteristics, and thermal stability. Thus, in some embodiments, an OLED including the amine-based compound may have improved driving voltage, light-emitting efficiency, and/or color purity.

While the present invention has been described in connection with certain exemplary embodiments, those of ordinary skill in the art will understand that various modifications may be made to the disclosed embodiments without departing from the spirit and scope of the appended claims, and equivalents thereof.

What is claimed is:

1. An amine-based compound represented by Formula 1:

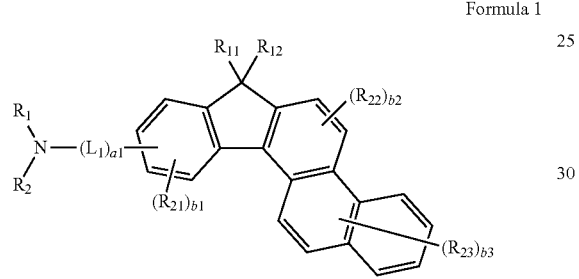

Formula 1 wherein, in Formula 1:

$L_1$ is selected from:
  a $C_3$-$C_{10}$ cycloalkylene group, a $C_2$-$C_{10}$ heterocycloalkylene group, a $C_3$-$C_{10}$ cycloalkenylene group, a $C_2$-$C_{10}$ heterocycloalkenylene group, a $C_6$-$C_{60}$ arylene group, and a $C_1$-$C_{60}$ heteroarylene group; and
  a $C_3$-$C_{10}$ cycloalkylene group, a $C_2$-$C_{10}$ heterocycloalkylene group, a $C_3$-$C_{10}$ cycloalkenylene group, a $C_2$-$C_{10}$ heterocycloalkenylene group, a $C_6$-$C_{60}$ arylene group, and a $C_1$-$C_{60}$ heteroarylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and —Si($Q_1$)($Q_2$)($Q_3$);

a1 is an integer of 0 to 5, and when a1 is an integer of 2 or more, the two or more $L_1$s are the same or different;

$R_1$ and $R_2$ are each independently selected from:
  a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, and a $C_1$-$C_{60}$ heteroaryl group; and
  a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, and a $C_1$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and —Si($Q_4$)($Q_5$)($Q_6$);

$R_{11}$, $R_{12}$, $R_{21}$, $R_{22}$, and $R_{23}$ are each independently selected from:
  a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and
  a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group; and
  a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group; and
  a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group, each substituted with at least one substituent selected from a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and —Si($Q_7$)($Q_8$)($Q_9$);

wherein $Q_1$ through $Q_9$ are each independently selected from:
  a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group;

b1 is an integer of 1, 2, or 3;

b2 is an integer of 1 or 2;

b3 is an integer of 1, 2, 3, 4, 5, or 6; and when b1, b2, and/or b3 is an integer of 2 or more, the two or more $R_{21}$s, $R_{22}$s, and/or $R_{23}$s are the same or different.

2. The amine-based compound of claim 1, wherein $L_1$ is selected from:

a phenylene group, a pentalenylene group, an indenylene group, a naphthalene group, an azulenylene group, a heptalenylene group, an indacenylene group, an acenaphthalene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinyiene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthalene group, an azulenylene group, a heptalenylene group, an indacenylene group, an acenaphthalene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group.

3. The amine-based compound of claim 1, wherein $L_1$ is selected from:

a phenylene group, a naphthalene group, a fluorenylene group, a spiro-fluorenylene group, a phenanthrenylene group, an anthracenylene group, a fluoranthrenylene group, a triphenylenylene group, a pyrenylene group, and a chrysenylene group; and a phenylene group, a naphthalene group, a fluorenylene group, a spiro-fluorenylene group, a phenanthrenylene group, an anthracenylene group, a fluoranthrenylene group, a triphenylenylene group, a pyrenylene group, and a chrysenylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group.

4. The amine-based compound of claim 1, wherein $L_1$ is represented by one of Formulae 2-1 through 2-30:

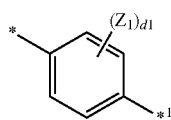

Formula 2-1

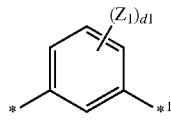

Formula 2-2

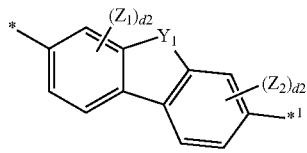

Formula 2-3

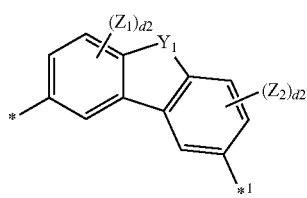

Formula 2-4

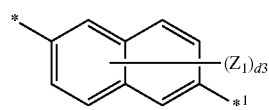

Formula 2-5

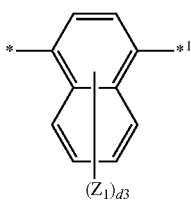

Formula 2-6

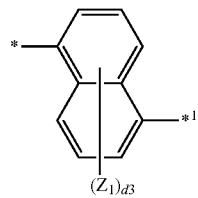

Formula 2-7

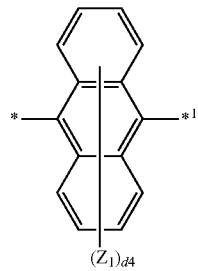

Formula 2-8

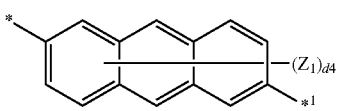

Formula 2-9

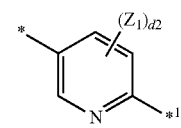

Formula 2-10

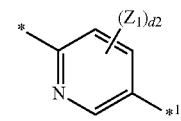

Formula 2-11

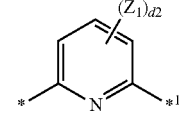

Formula 2-12

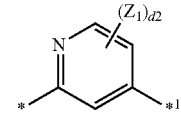

Formula 2-13

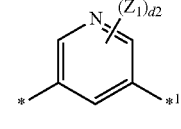

Formula 2-14

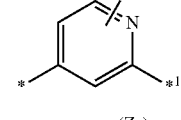

Formula 2-15

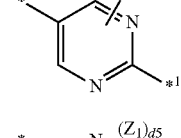

Formula 2-16

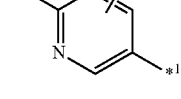

Formula 2-17

-continued

Formula 2-18
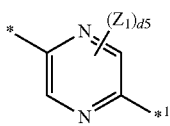

Formula 2-19
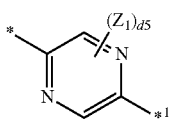

Formula 2-20
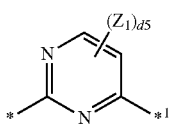

Formula 2-21
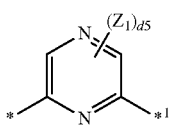

Formula 2-22
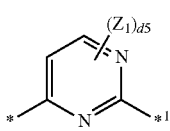

Formula 2-23
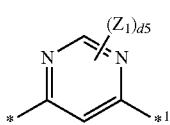

Formula 2-24
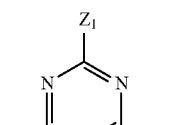

Formula 2-25
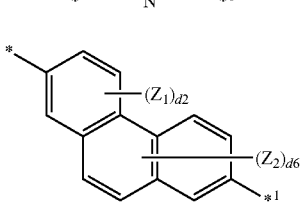

Formula 2-26
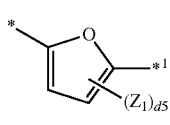

Formula 2-27
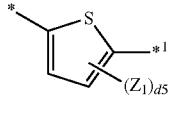

Formula 2-28
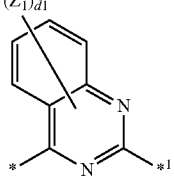

-continued

Formula 2-29
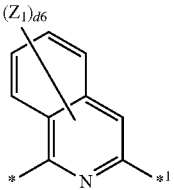

Formula A; 2-30
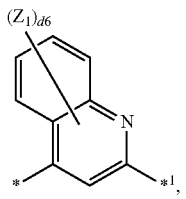

wherein, in Formulae 2-1 through 2-30:

$Y_1$ is O, S, S(=O), S(=O)$_2$, C($Z_3$)($Z_4$), N($Z_5$), or Si($Z_6$)($Z_7$);

$Z_1$ through $Z_7$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group;

d1 is an integer of 1 to 4;
d2 is an integer of 1 to 3;
d3 is an integer of 1 to 6;
d4 is an integer of 1 to 8;
d5 is an integer of 1 or 2;
d6 is an integer of 1 to 5;

when d1, d2, d3, d4, d5, and/or d6 is an integer of 2 or more, the two or more $Z_1$s and/or $Z_2$s are the same or different; and

* and *' are each a binding site to the nitrogen (N) atom of Formula 1, to a corresponding atom of Formula 1, or to another $L_1$.

5. The amine-based compound of claim 1, wherein $L_1$ is represented by one of Formulae 3-1 through 3-19:

Formula 3-1
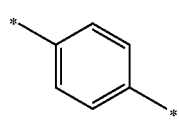

Formula 3-2
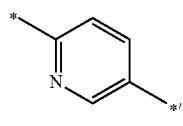

111
-continued
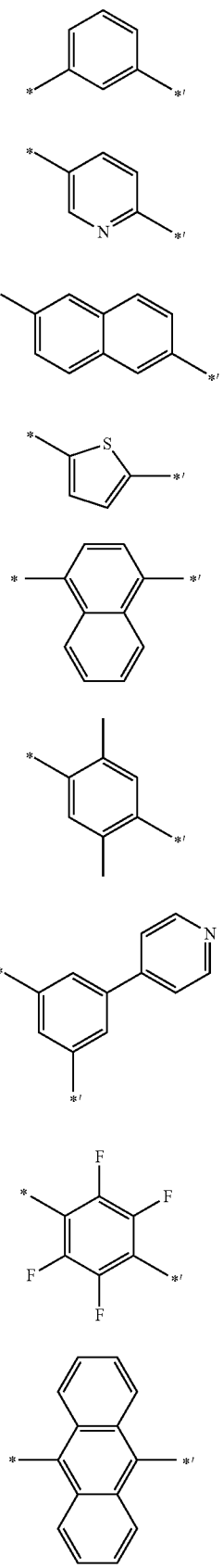
Formula 3-3
Formula 3-4
Formula 3-5
Formula 3-6
Formula 3-7
Formula 3-8
Formula 3-9
Formula 3-10
Formula 3-11
112
-continued
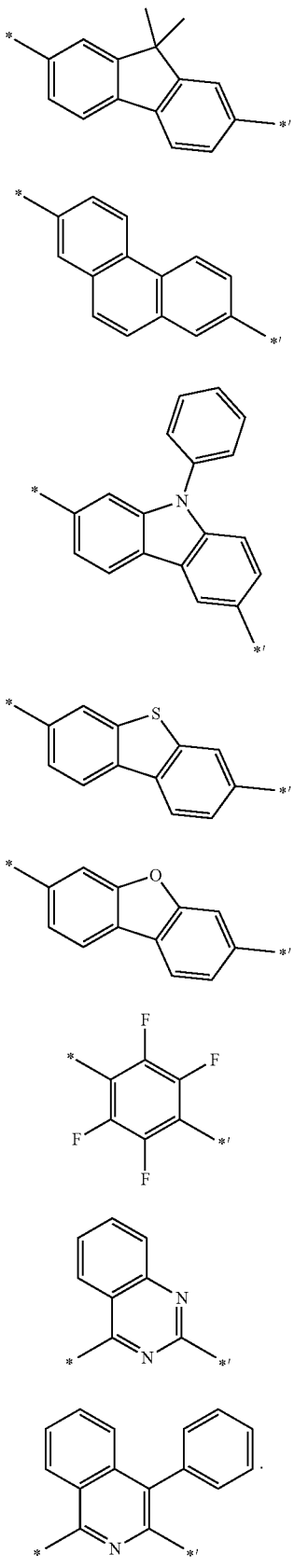
Formula 3-12
Formula 3-13
Formula 3-14
Formula 3-15
Formula 3-16
Formula 3-17
Formula 3-18
Formula 3-19 wherein * and *' are each a binding site to the nitrogen (N) atom of Formula 1, to a corresponding atom of Formula 1, or to another one of $L_1$.

6. The amine-based compound of claim 1, wherein a1 is an integer of 0 or 1.

7. The amine-based compound of claim 1, wherein $R_1$ and $R_2$ are each independently selected from:
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, and a dibenzocarbazolyl group; and
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, and a dibenzocarbazolyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, a quinazolinyl group, and —Si($Q_4$)($Q_5$)($Q_6$);
wherein $Q_4$ through $Q_6$ are each independently selected from a hydrogen atom, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group.

8. The amine-based compound of claim 1, wherein $R_{11}$, $R_{12}$, $R_{21}$, $R_{22}$, and $R_{23}$ are each independently selected from:
a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; and
a $C_1$-$C_{20}$ alkyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group; and
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, and a dibenzocarbazolyl group; and
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolylene group, a triazinyl group, a dibenzofuranyl group, a dibenzothiophenyl group, a benzocarbazolyl group, and a dibenzocarbazolyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, a quinazolinyl group, and —Si($Q_7$)($Q_8$)($Q_9$);

wherein $Q_7$ through $Q_9$ are each independently selected from a hydrogen atom, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group.

9. The amine-based compound of claim 1, wherein:
$R_{11}$, $R_{12}$, $R_{21}$, $R_{22}$, and $R_{23}$ are each independently selected from:
a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; and
a $C_1$-$C_{20}$ alkyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a pyridinyl group, a pyrimidinyl group, a triazinyl group, a quinolinyl group, an isoquinolinyl group, and a quinazolinyl group; and a group represented by one of Formulae 4-1 through 4-29, $R_1$ and $R_2$ are each independently selected from groups represented by Formulae 4-1 through 4-29,

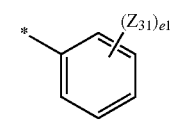

Formula 4-1

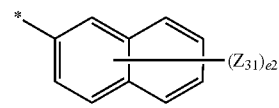

Formula 4-2

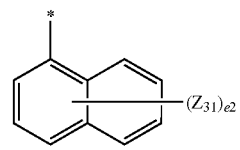

Formula 4-3

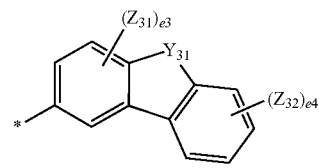

Formula 4-4

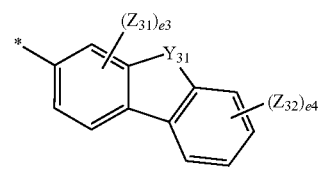

Formula 4-5

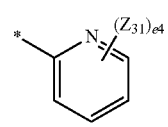

Formula 4-6

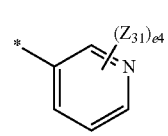

Formula 4-7

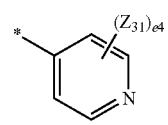

Formula 4-8

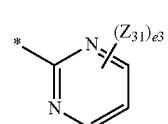

Formula 4-9

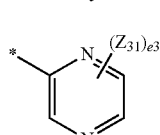

Formula 4-10

-continued

Formula 4-11

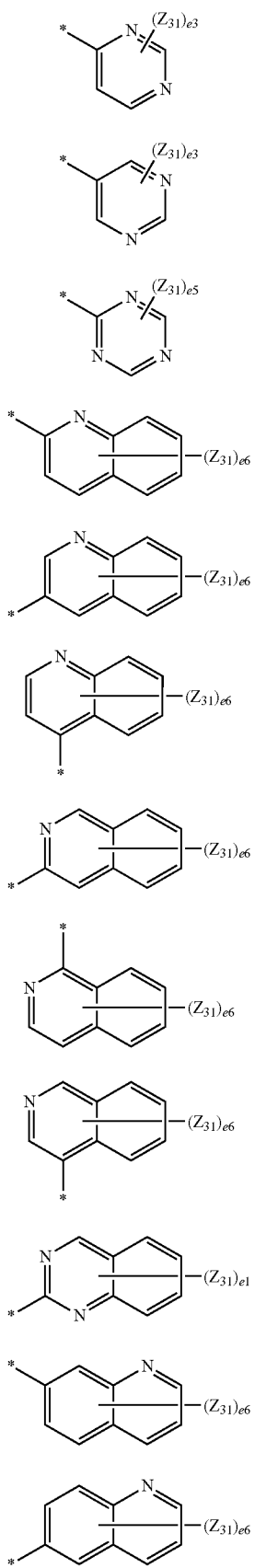

Formula 4-12

Formula 4-13

Formula 4-14

Formula 4-15

Formula 4-16

Formula 4-17

Formula 4-18

Formula 4-19

Formula 4-20

Formula 4-21

Formula 4-22

-continued

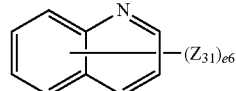

Formula 4-23

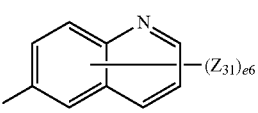

Formula 4-24

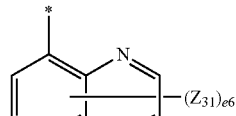

Formula 4-25

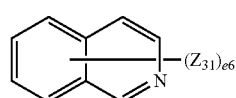

Formula 4-26

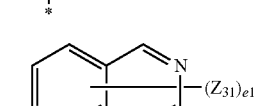

Formula 4-27

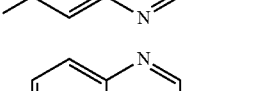

Formula 4-28

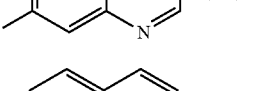

Formula 4-29

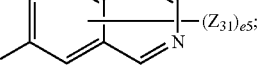

wherein, in Formulae 4-1 through 4-29:

$Y_{31}$ is O, S, $C(Z_{33})(Z_{34})$, $N(Z_{35})$ or $Si(Z_{36})(Z_{37})$;

$Z_{31}$ through $Z_{37}$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, a quinazolinyl group, and —$Si(Q_{11})(Q_{12})(Q_{13})$, wherein $Q_{11}$ through $Q_{13}$ are each independently selected from the group consistent of a hydrogen atom, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group;

e1 is an integer of 1 to 5;
e2 is an integer of 1 to 7;
e3 is an integer of 1 to 3;
e4 is an integer of 1 to 4;
e5 is an integer of 1 or 2;
e6 is an integer of 1 to 6;
when e1, e2, e3, e4, e5, and/or e6 is an integer of 2 or more, the two or more $Z_1$s and/or $Z_2$s are the same or different; and
* is a binding site to a corresponding atom of Formula 1.

10. The amine-based compound of claim 1, wherein:
$R_{11}$, $R_{12}$, $R_{21}$, $R_{22}$, and $R_{23}$ are each independently selected from:
  a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; and
  a $C_1$-$C_{20}$ alkyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthrenyl group, a fluorenyl group, a carbazolyl group, a pyridinyl group, a pyrimidinyl group, a triazinyl group, a quinolinyl group, an isoquinolinyl group, and a quinazolinyl group; and
  a group represented by one of Formulae 5-1 through 5-21; and
$R_1$ and $R_2$ are each independently selected from groups represented by one of Formulae 5-1 through 5-21;

Formula 5-1

Formula 5-2

Formula 5-3

Formula 5-4

Formula 5-5

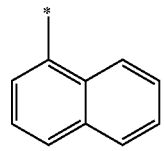

Formula 5-6

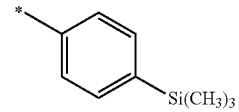

Formula 5-7

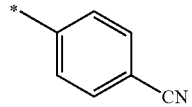

Formula 5-8

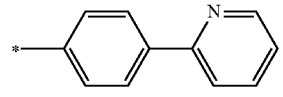

Formula 5-9

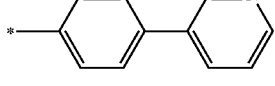

Formula 5-10

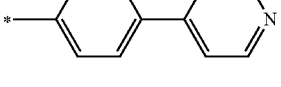

Formula 5-11

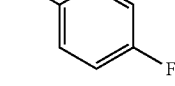

Formula 5-12

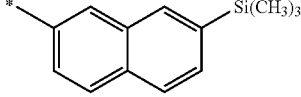

Formula 5-13

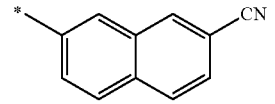

Formula 5-14

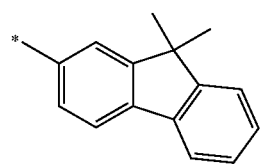

Formula 5-15

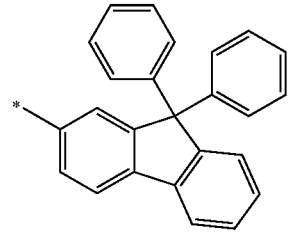

Formula 5-16

-continued

Formula 5-17
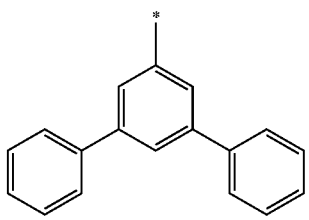

Formula 5-18
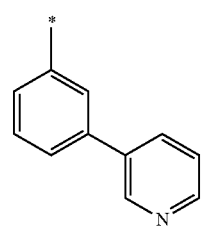

Formula 5-19
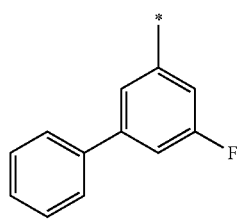

Formula 5-20
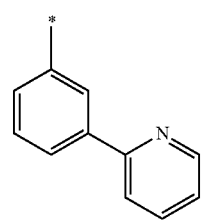

Formula 5-21
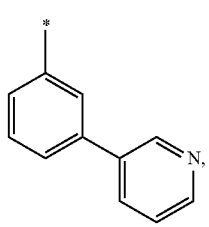

and

* is a binding site to a corresponding atom of Formula 1.

11. The amine-based compound of claim 1, wherein $R_{21}$, $R_{22}$, and $R_{23}$ are each a hydrogen atom.

12. The amine-based compound of claim 1, wherein the compound represented by Formula 1 is a compound represented by Formula 1A:

Formula 1A
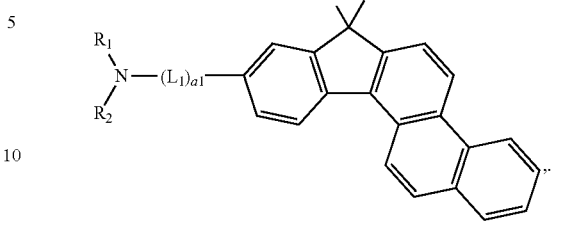

13. The amine-based compound of claim 1, wherein the compound represented by Formula 1 is a compound represented by one of Formulae 1A(1) through 1A(6):

Formula 1A(1)
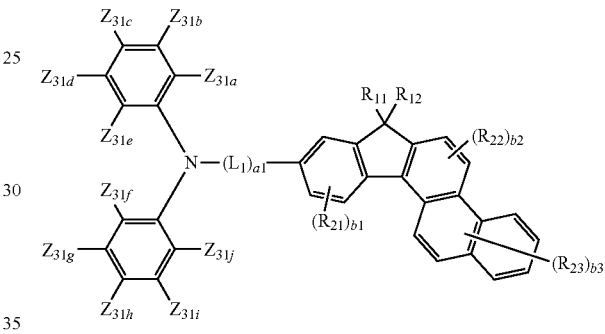

Formula 1A(2)
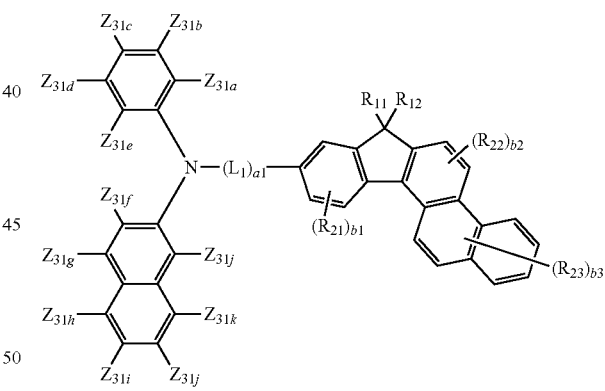

Formula 1A(3)
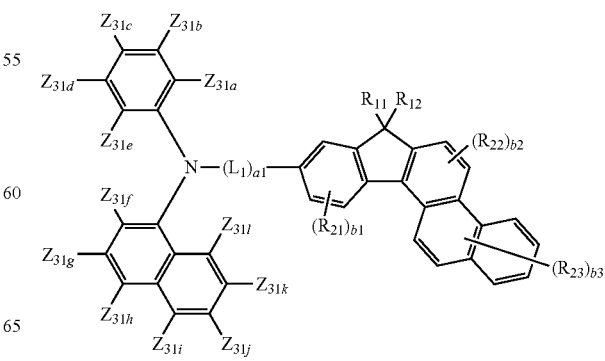

Formula 1A(4)

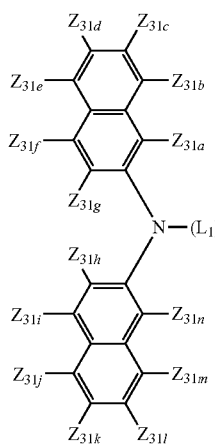

Formula 1A(5)

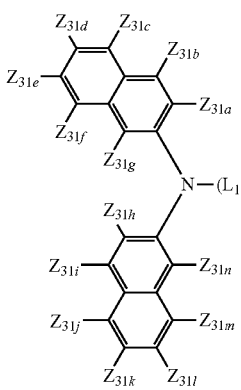

Formula 1A(6)

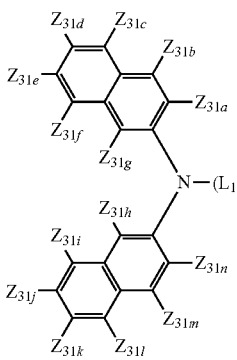

wherein, in Formulae 1A(1) through 1A(6):

$Z_{31a}$ through $Z_{31n}$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and —Si($Q_4$)($Q_5$)($Q_6$), wherein $Q_4$ through $Q_6$ are each independently selected from a hydrogen atom, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, and a $C_1$-$C_{60}$ heteroaryl group.

14. The amine-based compound of claim 13, wherein, in Formulae 1A(1) through 1A(6):

$L_1$ is selected from:
a phenylene group, a naphthalene group, a fluorenylene group, a spiro-fluorenylene group, a phenanthrenylene group, an anthracenylene group, a fluoranthrenylene group, a triphenylenylene group, a pyrenylene group, and a chrysenylene group; and
a phenylene group, a naphthalene group, a fluorenylene group, a spiro-fluorenylene group, a phenanthrenylene group, an anthracenylene group, a fluoranthrenylene group, a triphenylenylene group, a pyrenylene group, and a chrysenylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group, a1 is an integer of 0 or 1;
$R_{11}$ and $R_{12}$ are each independently selected from:
a $C_1$-$C_{20}$ alkyl group and a $C_1$-$C_{20}$ alkoxy group; and
a $C_1$-$C_{20}$ alkyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group; and
a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group; and
a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group;

$R_{21}$, $R_{22}$, and $R_{23}$ are each independently selected from:
a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; and a $C_1$-$C_{20}$ alkyl group and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group; and a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group; and a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group; and b1, b2, and b3 are each independently an integer of 1 or 2, and when b1, b2, and/or b3 is an integer of 2, the two $R_{21}$s, $R_{22}$s, and/or $R_{23}$s are the same or different.

15. The amine-based compound of claim 1, wherein the amine-based compound is one of Compounds 1 through 15:

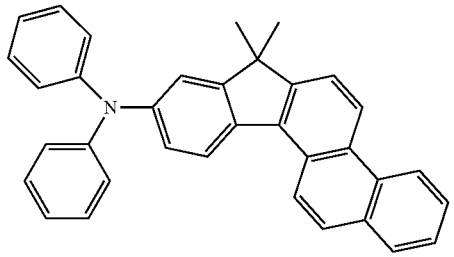

1

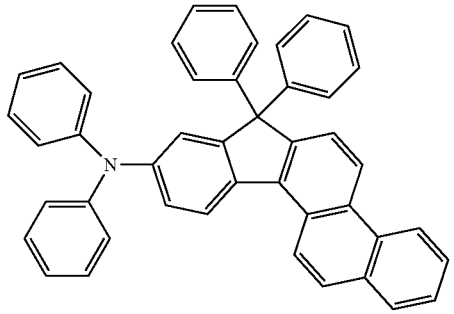

2

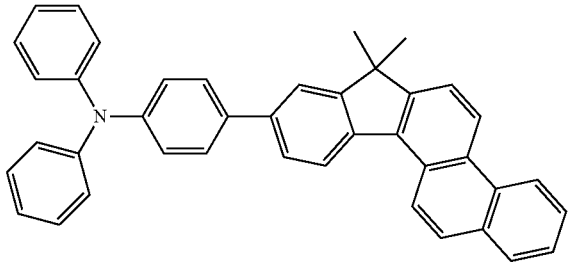

3

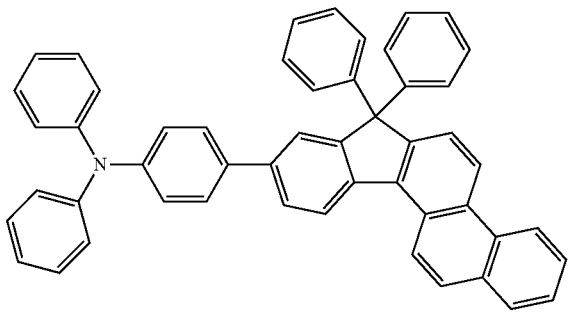

4

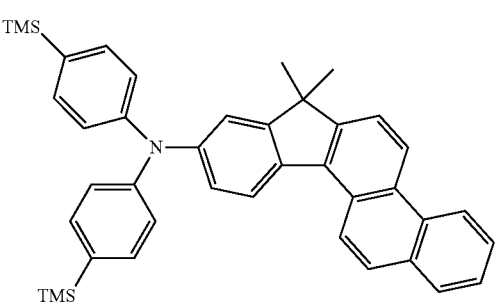

5

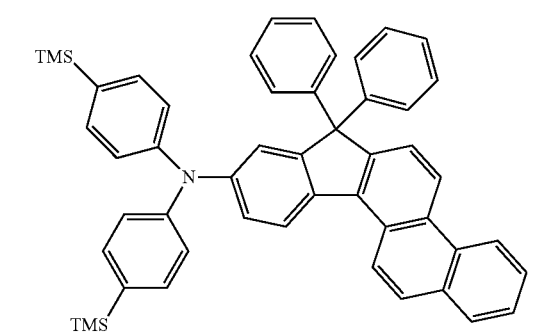
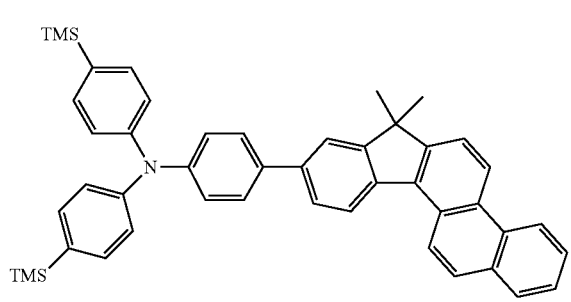
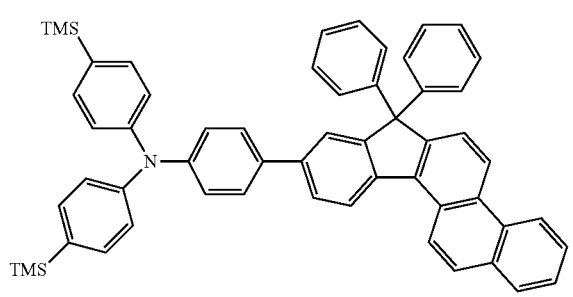
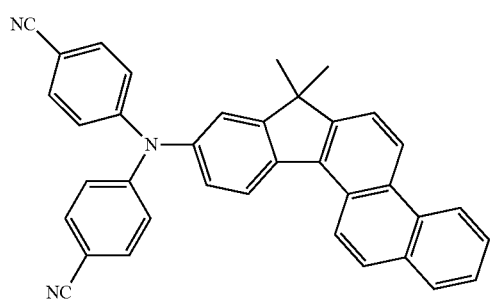
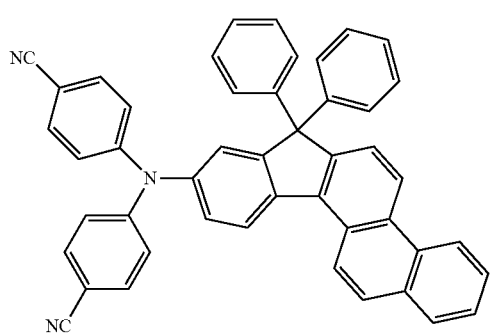
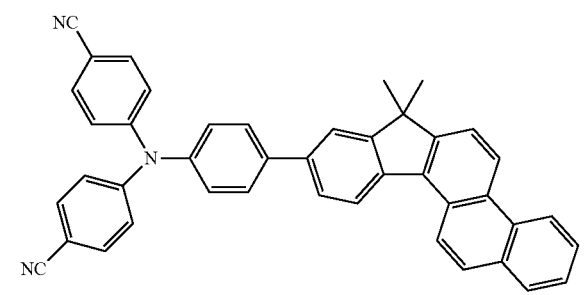
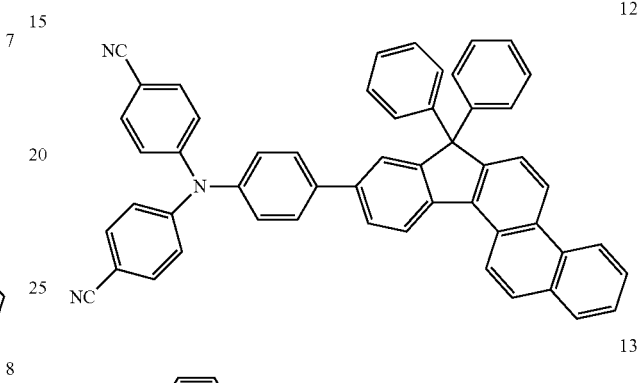
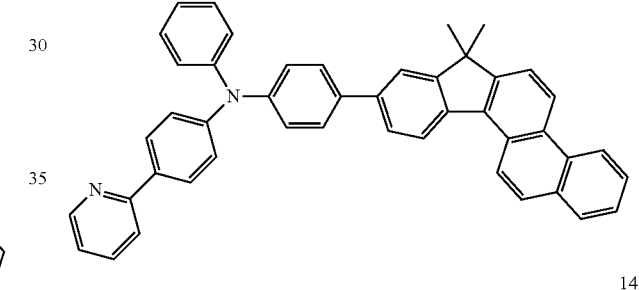
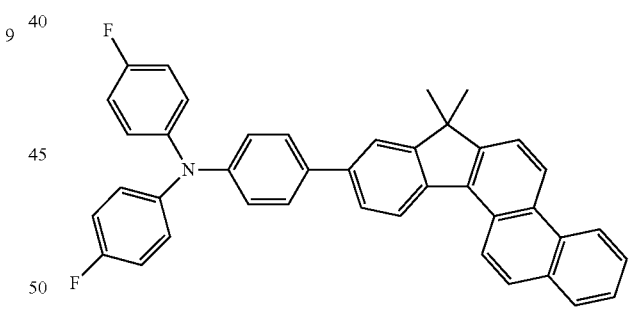
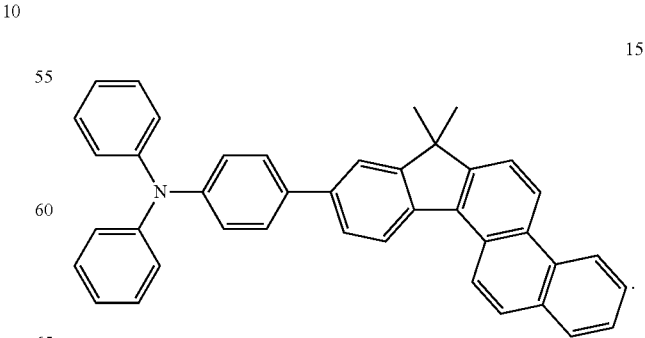

16. An organic light-emitting diode (OLED) comprising:
a first electrode;
a second electrode; and
an organic layer between the first electrode and the second electrode, the organic layer comprising an emission layer and at least one amine-based compound of claim 1.

17. The OLED of claim 16, wherein:
the first electrode is an anode,
the second electrode is a cathode, and
the organic layer comprises:
    a hole transporting region between the first electrode and the emission layer, the hole transporting region comprising at least one of a hole injection layer, a hole transport layer, or an electron blocking layer; and
    an electron transporting region between the emission layer and the second electrode, the electron transporting region comprising at least one of a hole blocking layer, an electron transport layer, or an electron injection layer.

18. The OLED of claim 16, wherein the amine-based compound is in the emission layer.

19. The OLED of claim 18, wherein:
the emission layer further comprises an anthracene-based compound,
the anthracene-based compound is a host; and
the amine-based compound is a dopant.

20. The OLED of claim 17, wherein the hole transporting region comprises at least one of a compound represented by Formula 300 and a compound represented by Formula 301:

Formula 300

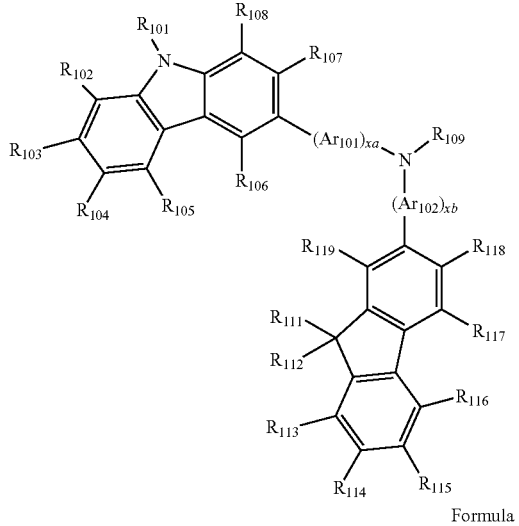

Formula 301

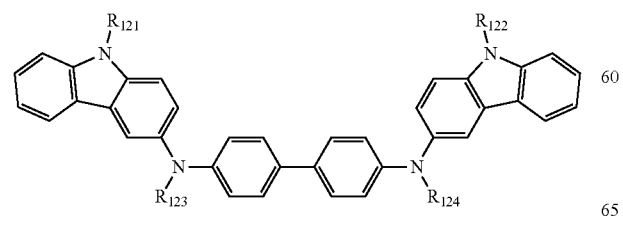

wherein, in Formula 300:
$Ar_{101}$ and $Ar_{102}$ are each independently selected from:
    a phenylene group, a pentalenylene group, an indenylene group, a naphthalene group, an azulenylene group, a heptalenylene group, an acenaphthalene group, a fluorenylene group, a phenarenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group; and
    a phenylene group, a pentalenylene group, an indenylene group, a naphthalene group, an azulenylene group, a heptalenylene group, an acenaphthalene group, a fluorenylene group, a phenarenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_1$-$C_{60}$ heteroaryl group;
in Formula 300, xa and xb are each independently an integer of 0, 1, or 2,
in Formulae 300 and 301, $R_{101}$ through $R_{108}$, $R_{111}$ through $R_{119}$, and $R_{121}$ through $R_{124}$ are each independently selected from:
    a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group; and
    a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, and a phosphoric acid group or a salt thereof; and
    a phenyl group, a naphthyl group, an anthracenyl group, a fluorenyl group, and a pyrenyl group; and
    a phenyl group, a naphthyl group, an anthracenyl group, a fluorenyl group, and a pyrenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group,
in Formula 300, $R_{109}$ is selected from
    a phenyl group, a naphthyl group, an anthracenyl group, a biphenyl group, and a pyridinyl group; and
    a phenyl group, a naphthyl group, an anthracenyl group, a biphenyl group and a pyridinyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group.

* * * * *